US012606857B2

(12) United States Patent
Ahn et al.

(10) Patent No.: US 12,606,857 B2
(45) Date of Patent: Apr. 21, 2026

(54) PROGRAMMED DNA-DRIVEN SELF-ASSEMBLED RNA HYDROGEL

(71) Applicant: Progeneer, Inc., Seoul (KR)

(72) Inventors: So Yeon Ahn, Seoul (KR); Srivithya Vellampatti Krishnamoorthy, Cheon Cheong-dong (KR); Soong Ho Um, Seoul (KR); Sung Oh, Seoul (KR); Seung Won Shin, Gyeonggi-do (KR)

(73) Assignee: Progeneer, Inc., Seoul (KR)

( * ) Notice: Subject to any disclaimer, the term of this patent is extended or adjusted under 35 U.S.C. 154(b) by 249 days.

(21) Appl. No.: 18/483,386

(22) Filed: Oct. 9, 2023

(65) Prior Publication Data

US 2024/0150806 A1     May 9, 2024

Related U.S. Application Data

(63) Continuation-in-part of application No. 17/084,432, filed on Oct. 29, 2020, now Pat. No. 11,814,662.

(30) Foreign Application Priority Data

Oct. 30, 2019     (KR) ........................ 10-2019-0136416
Jun. 24, 2020     (KR) ........................ 10-2020-0077146

(51) Int. Cl.
| | |
|---|---|
| *C12P 21/00* | (2006.01) |
| *C12N 9/12* | (2006.01) |
| *C12N 15/10* | (2006.01) |
| *C12P 19/34* | (2006.01) |

(52) U.S. Cl.
CPC ............ *C12P 21/00* (2013.01); *C12N 9/1276* (2013.01); *C12N 15/1096* (2013.01); *C12P 19/34* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 8,715,732 | B2 | 5/2014 | Luo et al. |
| 11,814,662 | B2 | 11/2023 | Ahn et al. |
| 2015/0050698 | A1 | 2/2015 | Um et al. |

FOREIGN PATENT DOCUMENTS

| | | |
|---|---|---|
| CN | 110423743 A | 11/2019 |
| CN | 110564812 A | 12/2019 |
| WO | 2016152936 A1 | 9/2016 |
| WO | 2019030155 A1 | 2/2019 |

OTHER PUBLICATIONS

Huang et al. ("A Pure DNA Hydrogel With Stable Catalytic Ability Produced by One-step Rolling Circle Amplification", Chemical Communications, vol. 53, No. 21, 2017, pp. 3038-3041) (Year: 2017).*
U.S. Appl. No. 17/084,432, "Corrected Notice of Allowability", Aug. 10, 2023, 8 pages.
U.S. Appl. No. 17/084,432, "Corrected Notice of Allowability", Sep. 15, 2023, 8 pages.
U.S. Appl. No. 17/084,432, "Notice of Allowance", Jul. 10, 2023, 10 pages.
Ali et al., "Rolling Circle Amplification: A Versatile Tool for Chemical Biology, Materials Science and Medicine", Chemical Society Reviews, vol. 43, No. 10, Mar. 2014, pp. 3324-3341.
Boho et al., "Gene-Activated Hydrogels in Regenerative Medicine", Available online at: https://cyberleninka.ru/article/n/gen-aktivirovannye-gidrogeli-v-regenerativnoy-meditsine, 2019, pp. 16-21 -.
CA3,154,593 "Office Action", May 4, 2023, 5 pages.
Conde et al., "Self-assembled RNA-Triple-Helix Hydrogel Scaffold for MicroRNA Modulation in the Tumour Microenvironment", Nature Materials, vol. 15, Dec. 7, 2015, 13 pages.
Endoh et al., "Conformational Dynamics of the RNA G-Quadruplex and its Effect on Translation Efficiency", Molecules, vol. 24, No. 8, Apr. 24, 2019, 14 pages.
Endoh et al., "Mechanical Insights Into Ribosomal Progression Overcoming RNA G-quadruplex From Periodical Translation Suppression in Cells", Scientific Reports, vol. 6, No. 1, Mar. 2016, 8 pages.
Endoh et al., "Suppression of Gene Expression by G-Quadruplexes in Open Reading Frames Depends on G- Quadruplex Stability", Angewandte Chemie International Edition, vol. 52, May 17, 2013, pp. 5522-5526.
Hansen et al., "Cell-Like Nanostructured Environments Alter Diffusion and Reaction Kinetics in Cell-Free Gene Expression", ChemBioChem, Available Online at:, Feb. 2, 2016, pp. 228-232.
Huang et al., "An RNA Aptamer Capable of Forming Hydrogel by Self-Assembly", Biomacromolecules, vol. 18, No. 7, Jun. 13, 2017, 31 pages.
Jain et al., "RNA Phase Transitions in Repeat Expansion Disorders", Nature, vol. 546, No. 7657, Jun. 8, 2017, 29 pages.

(Continued)

*Primary Examiner* — Manjunath N Rao
*Assistant Examiner* — Jae W Lee
(74) *Attorney, Agent, or Firm* — Kilpatrick Townsend & Stockton LLP

(57) ABSTRACT

This application provides methods and compositions related to constructing nucleic acid hydrogels (e.g., RNA hydrogels) having repetitive monomer units, each monomer unit includes one or more G-quadruplex sequences. These G-quadruplex sequences cross-link the nucleic acid concatemer such that it self-assembles into a hydrogel under appropriate conditions. In some embodiments, each monomeric unit of the nucleic acid concatemer comprises a coding sequence for polypeptide of interest; and the nucleic acid hydrogel formed by the nucleic acid concatemer can be used for expressing the polypeptide in high quantities. In some embodiments, at least two RNA concatemers comprising G-quadruplex sequences are produced, one further comprising a spacer and the other further comprising a sequence encoding a polypeptide of interest. These two RNA concatemers are combined and self assembled to form a single, wideband RNA hydrogel.

18 Claims, 45 Drawing Sheets

Specification includes a Sequence Listing.

(56)     References Cited

OTHER PUBLICATIONS

Jp2022-525268, "Office Action", Jun. 6, 2023, 7 pages.
Kahn et al., "DNA Microgels as a Platform for Cell-free Protein Expression and Display", Biomacromolecules, vol. 17, No. 16, Apr. 25, 2016, pp. 2019-2026.
Lee et al., "A Mechanical Metamaterial made from a DNA Hydrogel", Nature Nanotechnology, vol. 7, Dec. 2, 2012, pp. 816-820.
Li et al., "Fabrication and Biomedical Applications of "Polymer-Like" Nucleic Acids Enzymatically Produced by Rolling Circle Amplification", American Chemical Society Applied Bio Materials, vol. 2, No. 10, Sep. 4, 2019, pp. 4106-4120.
Park et al., "A Cell-free Protein-producing Gel", Nature Materials, vol. 8, Mar. 29, 2009, pp. 432-437.
PCT/IB2020/060181, "International Preliminary Report on Patentability", May 12, 2022, 8 pages.
PCT/IB2020/060181, "International Search Report and Written Opinion", Feb. 3, 2021, 12 pages.
Ru2022114124, "Office Action", Jun. 14, 2023, 17 pages.
Teng et al., "C-Rich Sequence in a Non-Template DNA Strand Regulates Structure Change of G-Quadruplex in a Template Strand during Transcription", Bulletin of the Chemical Society of Japan, vol. 92, 2019, pp. 572-577.
Um et al., "Enzyme-catalysed Assembly of DNA Hydrogel", Nature Materials, vol. 5, No. 10, Sep. 24, 2006, pp. 797-801.
Whitfield et al., "Cell-free Protein Synthesis in Hydrogel Materials", ChemComm, vol. 56, No. 52, Jul. 4, 2020, pp. 7108-7111.
Wu et al., "Formation of DNA:RNA Hybrid G-Quadruplex in Bacterial Cells and Its Dominance over the Intramolecular DNA G-Quadruplex in Mediating Transcription Termination", Angewandte Chemie International Edition, vol. 54, Feb. 16, 2015, pp. 2447-2451.
Zheng et al., "Co-transcriptional Formation of Dna:rna Hybrid G-quadruplex and Potential Function as Constitutional Cis Element for Transcription Control", Nucleic Acids Research, vol. 41, No. 10, Apr. 2013, pp. 5533-5541.
ZHU , "Part:BBa_K3060009", Registry of Standard Biological Parts, Oct. 16, 2019, 3 pages.

* cited by examiner

RG4 Hydrogel

G4

Transcription

—— T7 promoter
—— G4 motif
—— Spacer

RG4

RGx

10 μM ThT

RNA scaffold

Lysate

Ribosome

Protein

Cutting out

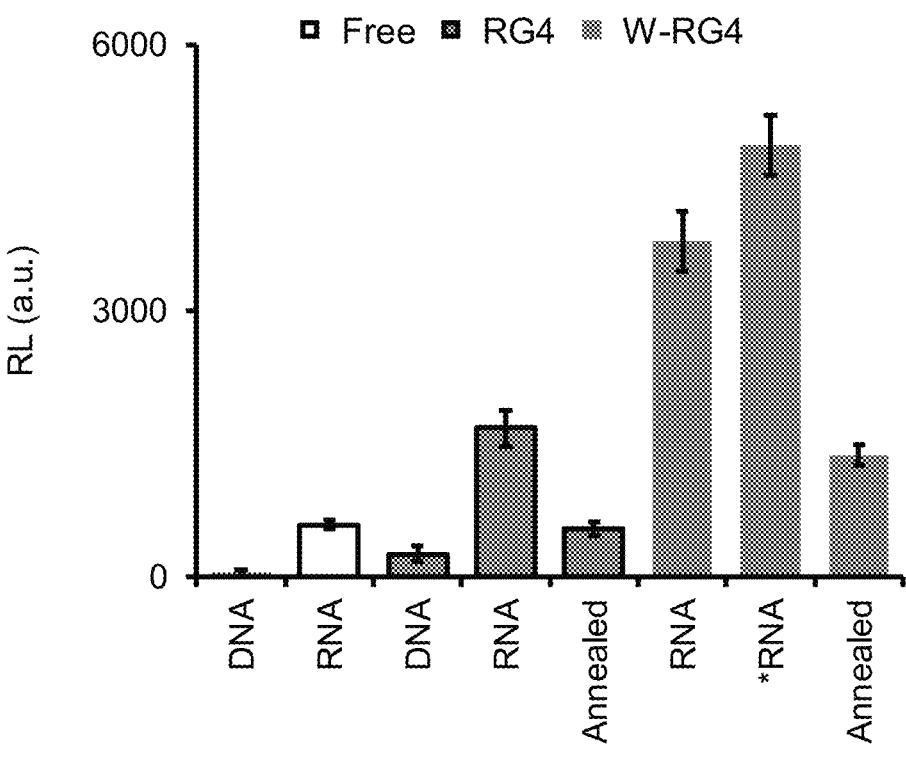
FIG. 5B
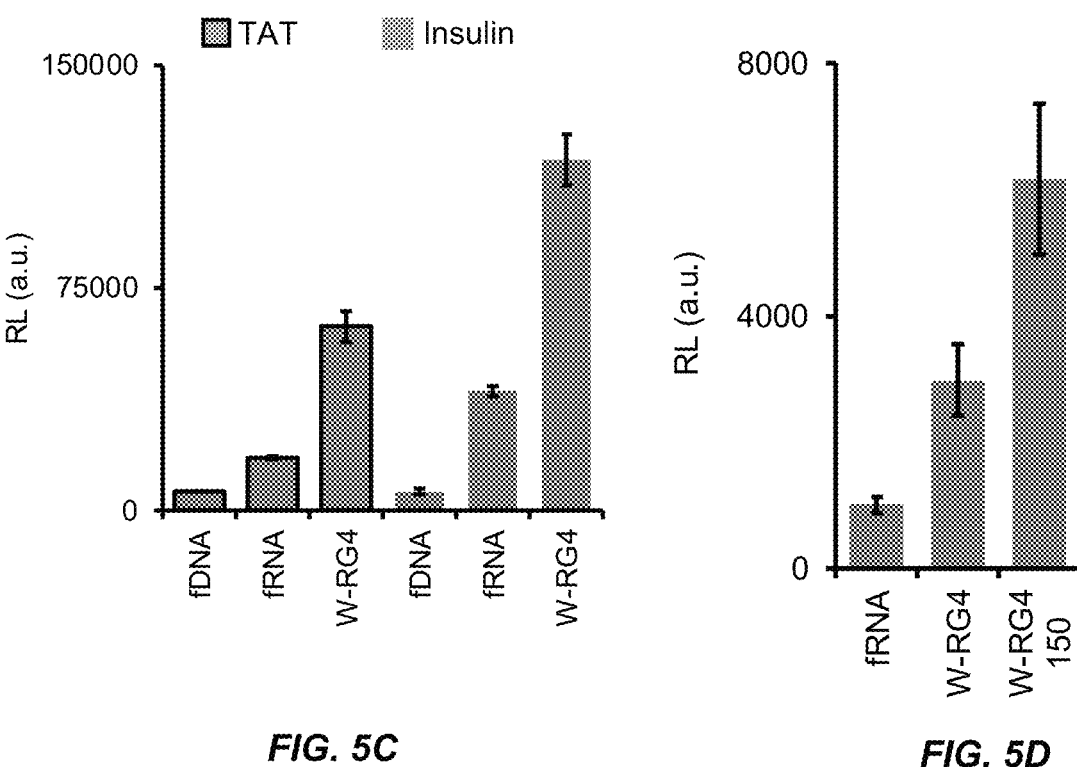
FIG. 5C
FIG. 5D

*Negative control: 30T RG4
*Raw gel: 75% HiBiT 150T W-RG4
*L-gel: lysate embedding gel expressed with no additional lysate
*L-L-gel: lysate embedding 75% HiBiT 150T W-RG4 expressed with additional lysate Original  4 °C  25 °C  37 °C
Annealed

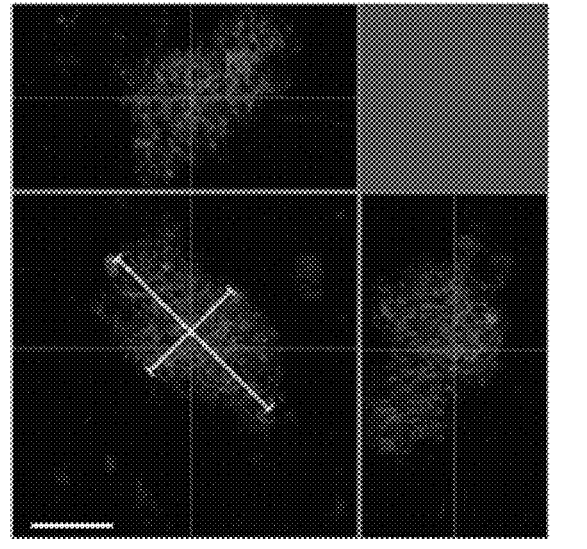
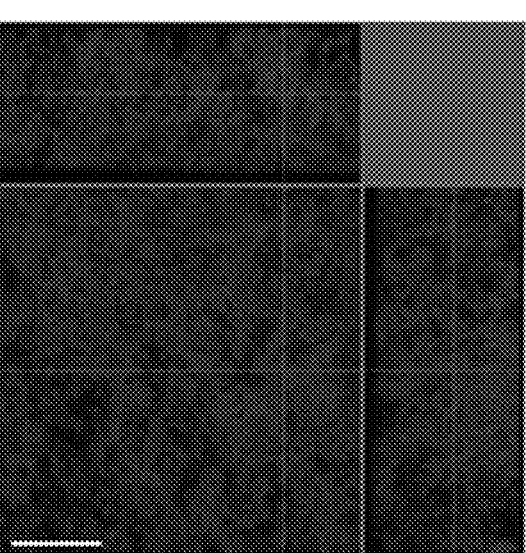
*FIG. 9A*                                        *FIG. 9B*
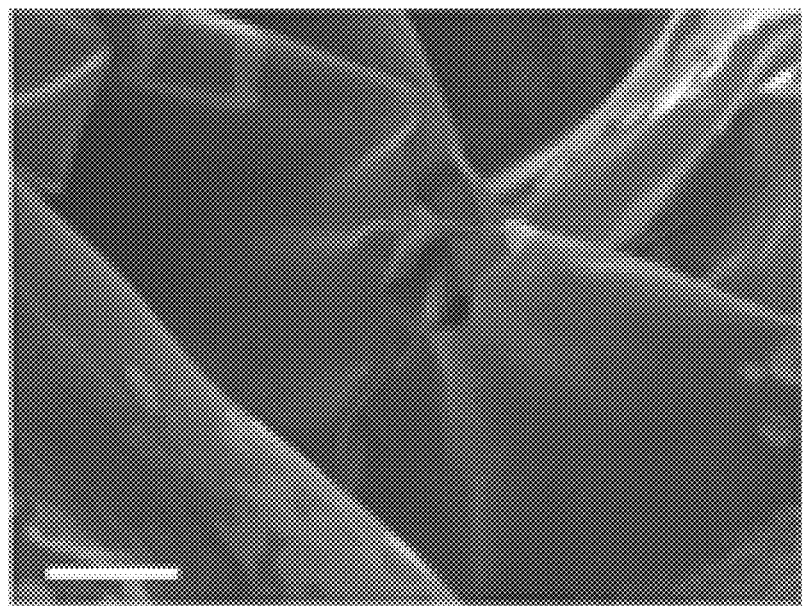
*FIG. 10*

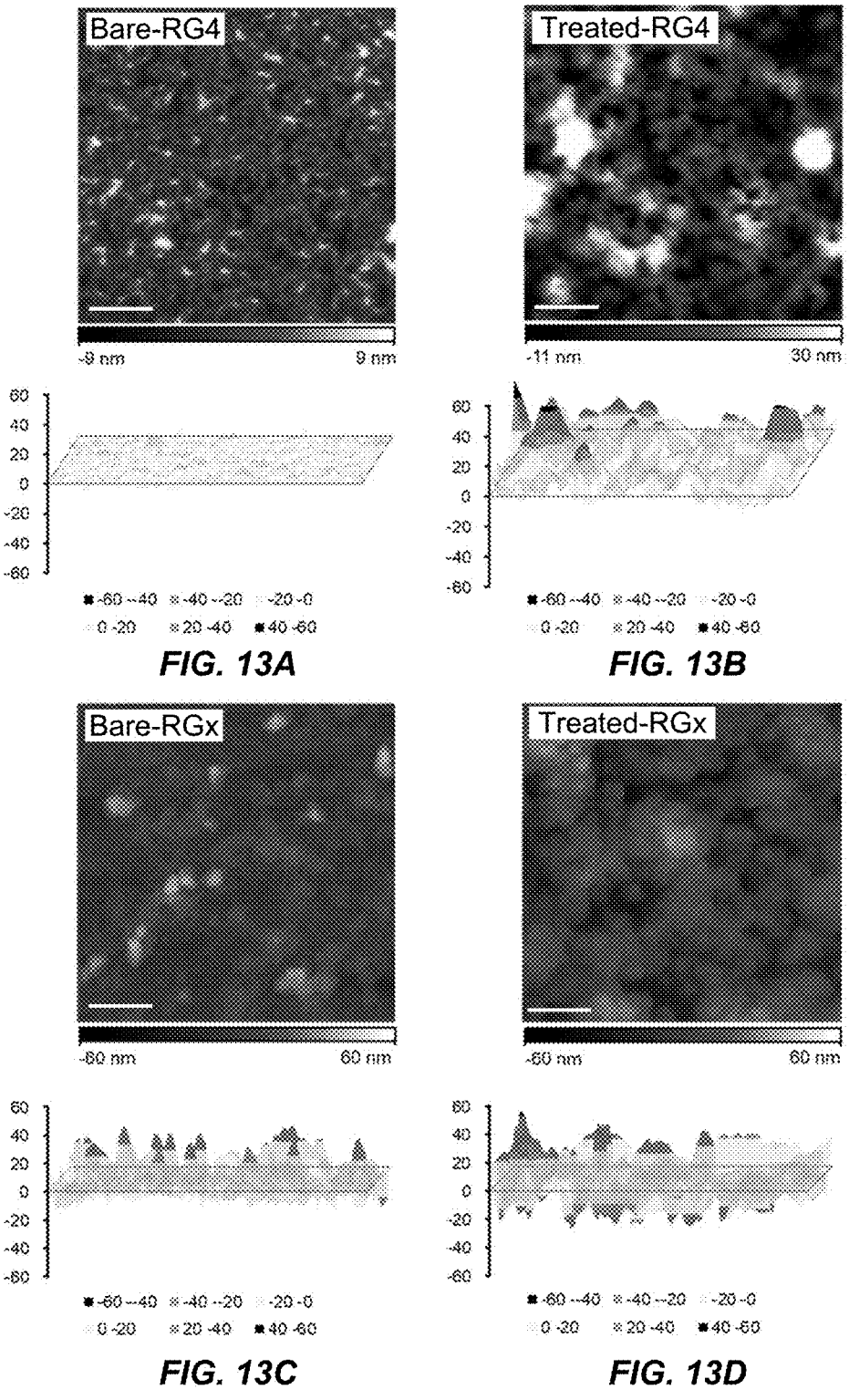
FIG. 13A                    FIG. 13B
FIG. 13C                    FIG. 13D

| Total RNA concentration | 3520.89 ng/μL |
| Molecular weight of a cycle | 19957.2 g/mole |
| G-quadruplex concentration | $1.062×10^{-4}$ unit/nm³ |
| Distance between G-quadruplex units | 21.11 nm |

RG4

RGx

Reaction time (h)

RGx

Wideband protein-encoding RG4 hydrogel

Transcription

T7 promoter
G4 motif
30 T
Protein

SEQUENCE LISTING

Sequence total quantity: 61
SEQ ID NO: 1            moltype = DNA   length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 1
accctaaccc ta                                                     12

-continued

```
SEQ ID NO: 2              moltype = RNA  length = 12
FEATURE                   Location/Qualifiers
misc_feature              1..12
                          note = Description of Artificial Sequence: Synthetic
                          oligonucleotide
source                    1..12
                          mol_type = other RNA
                          organism = synthetic construct
SEQUENCE: 2
tagggttagg gt                                                     12

SEQ ID NO: 3              moltype = DNA  length = 28
FEATURE                   Location/Qualifiers
misc_feature              1..28
                          note = Description of Artificial Sequence: Synthetic
                          oligonucleotide
source                    1..28
                          mol_type = other DNA
                          organism = synthetic construct
SEQUENCE: 3
atagtgagtc gtattaaccc taacccta                                    28

SEQ ID NO: 4              moltype = DNA  length = 37
FEATURE                   Location/Qualifiers
misc_feature              1..37
                          note = Description of Artificial Sequence: Synthetic
                          oligonucleotide
source                    1..37
                          mol_type = other DNA
                          organism = synthetic construct
SEQUENCE: 4
atagtgagtc gtattaaccc taaccctatt tatccct                          37

SEQ ID NO: 5              moltype = DNA  length = 44
FEATURE                   Location/Qualifiers
misc_feature              1..44
                          note = Description of Artificial Sequence: Synthetic
                          oligonucleotide
source                    1..44
                          mol_type = other DNA
                          organism = synthetic construct
SEQUENCE: 5
atagtgagtc gtattaaccc taaccctatt ttttttttat ccct                  44

SEQ ID NO: 6              moltype = DNA  length = 64
FEATURE                   Location/Qualifiers
misc_feature              1..64
                          note = Description of Artificial Sequence: Synthetic
                          oligonucleotide
source                    1..64
                          mol_type = other DNA
                          organism = synthetic construct
SEQUENCE: 6
atagtgagtc gtattaaccc taaccctatt tttttttttt tttttttttt tttttttat  60
ccct                                                              64

SEQ ID NO: 7              moltype = DNA  length = 94
FEATURE                   Location/Qualifiers
misc_feature              1..94
                          note = Description of Artificial Sequence: Synthetic
                          oligonucleotide
source                    1..94
                          mol_type = other DNA
                          organism = synthetic construct
SEQUENCE: 7
atagtgagtc gtattaaccc taaccctatt tttttttttt tttttttttt tttttttttt  60
tttttttttt tttttttttt tttttttat ccct                              94

SEQ ID NO: 8              moltype = DNA  length = 124
FEATURE                   Location/Qualifiers
misc_feature              1..124
                          note = Description of Artificial Sequence: Synthetic
                          polynucleotide
source                    1..124
                          mol_type = other DNA
                          organism = synthetic construct
SEQUENCE: 8
atagtgagtc gtattaaccc taaccctatt tttttttttt tttttttttt tttttttttt  60
```

-continued

```
tttttttttt tttttttttt tttttttttt tttttttttt tttttttttt tttttttttat   120
ccct                                                                  124

SEQ ID NO: 9              moltype = DNA   length = 154
FEATURE                   Location/Qualifiers
misc_feature              1..154
                          note = Description of Artificial Sequence: Synthetic
                          polynucleotide
source                    1..154
                          mol_type = other DNA
                          organism = synthetic construct
SEQUENCE: 9
atagtgagtc gtattaaccc taaccctatt tttttttttt tttttttttt tttttttttt      60
tttttttttt tttttttttt tttttttttt tttttttttt tttttttttt tttttttttt     120
tttttttttt tttttttttt tttttttttat ccct                                154

SEQ ID NO: 10             moltype = DNA   length = 64
FEATURE                   Location/Qualifiers
misc_feature              1..64
                          note = Description of Artificial Sequence: Synthetic
                          oligonucleotide
source                    1..64
                          mol_type = other DNA
                          organism = synthetic construct
SEQUENCE: 10
atagtgagtc gtattaacag taacagtatt tttttttttt tttttttttt tttttttttat      60
ccct                                                                   64

SEQ ID NO: 11             moltype = DNA   length = 184
FEATURE                   Location/Qualifiers
misc_feature              1..184
                          note = Description of Artificial Sequence: Synthetic
                          polynucleotide
source                    1..184
                          mol_type = other DNA
                          organism = synthetic construct
SEQUENCE: 11
atagtgagtc gtattaaccc taaccctatt tttttttttt tttttttttt tttttttttt      60
tttttttttt tttttttttt tttttttttt tttttttttt tttttttttt tttttttttt     120
tttttttttt tttttttttt tttttttttt tttttttttt tttttttttt tttttttttat     180
ccct                                                                  184

SEQ ID NO: 12             moltype = DNA   length = 22
FEATURE                   Location/Qualifiers
misc_feature              1..22
                          note = Description of Artificial Sequence: Synthetic primer
source                    1..22
                          mol_type = other DNA
                          organism = synthetic construct
SEQUENCE: 12
taatacgact cactataggg at                                               22

SEQ ID NO: 13             moltype = RNA   length = 12
FEATURE                   Location/Qualifiers
misc_feature              1..12
                          note = Description of Artificial Sequence: Synthetic
                          oligonucleotide
source                    1..12
                          mol_type = other RNA
                          organism = synthetic construct
SEQUENCE: 13
tactgttact gt                                                          12

SEQ ID NO: 14             moltype = DNA   length = 94
FEATURE                   Location/Qualifiers
misc_feature              1..94
                          note = Description of Artificial Sequence: Synthetic
                          oligonucleotide
source                    1..94
                          mol_type = other DNA
                          organism = synthetic construct
SEQUENCE: 14
atagtgagtc gtattaaccc taaccctatt agctaatctt cttgaacagc cgccagccgc      60
tcaccatatt ttttcctcct tatacttaat ccct                                 94

SEQ ID NO: 15             moltype = DNA   length = 95
FEATURE                   Location/Qualifiers
misc_feature              1..95
                          note = Description of Artificial Sequence: Synthetic
```

-continued

```
                          oligonucleotide
source                    1..95
                          mol_type = other DNA
                          organism = synthetic construct
SEQUENCE: 15
acagtaacag tattagctaa tcttcttgaa cagccgccag ccgctcacca tattttttcc   60
tccttatact taatcccctta tagtgagtcg tatta                             95

SEQ ID NO: 16             moltype = DNA  length = 124
FEATURE                   Location/Qualifiers
misc_feature              1..124
                          note = Description of Artificial Sequence: Synthetic
                           polynucleotide
source                    1..124
                          mol_type = other DNA
                          organism = synthetic construct
SEQUENCE: 16
atagtgagtc gtattaaccc taaccctatt agctaatctt cttgaacagc cgccagccgc   60
tcactcttcg tcgctgtctc cgcttcttcc tgcccatatt ttttcctcct tatacttaat  120
ccct                                                              124

SEQ ID NO: 17             moltype = DNA  length = 124
FEATURE                   Location/Qualifiers
misc_feature              1..124
                          note = Description of Artificial Sequence: Synthetic
                           polynucleotide
source                    1..124
                          mol_type = other DNA
                          organism = synthetic construct
SEQUENCE: 17
acagtaacag tattagctaa tcttcttgaa cagccgccag ccgctcactc ttcgtcgctg   60
tctccgcttc ttcctgccca tattttttcc tccttatact taatccctat agtgagtcgt  120
atta                                                              124

SEQ ID NO: 18             moltype = DNA  length = 184
FEATURE                   Location/Qualifiers
misc_feature              1..184
                          note = Description of Artificial Sequence: Synthetic
                           polynucleotide
source                    1..184
                          mol_type = other DNA
                          organism = synthetic construct
SEQUENCE: 18
atagtgagtc gtattaaccc taaccctatt agctaatctt cttgaacagc cgccagccgc   60
tcacggtgtt gggtgtgtag aagaagcctc gttccccgca cactaggtag agagcttcca  120
ccaggtgtga gccgcacagg tgttggttca caaacatatt ttttcctcct tatacttaat  180
ccct                                                              184

SEQ ID NO: 19             moltype = DNA  length = 184
FEATURE                   Location/Qualifiers
misc_feature              1..184
                          note = Description of Artificial Sequence: Synthetic
                           polynucleotide
source                    1..184
                          mol_type = other DNA
                          organism = synthetic construct
SEQUENCE: 19
acagtaacag tattagctaa tcttcttgaa cagccgccag ccgctcacgg tgttgggtgt   60
gtagaagaag cctcgttccc cgcacactag gtagagagct tccaccaggt gtgagccgca  120
caggtgttgg ttcacaaaca tattttttcc tccttatact taatccctat agtgagtcgt  180
atta                                                              184

SEQ ID NO: 20             moltype = DNA  length = 12
FEATURE                   Location/Qualifiers
misc_feature              1..12
                          note = Description of Artificial Sequence: Synthetic
                           oligonucleotide
source                    1..12
                          mol_type = other DNA
                          organism = synthetic construct
SEQUENCE: 20
tagggttagg gt                                                       12

SEQ ID NO: 21             moltype = DNA  length = 36
FEATURE                   Location/Qualifiers
misc_feature              1..36
                          note = Description of Artificial Sequence: Synthetic
                           oligonucleotide
source                    1..36
```

```
                              mol_type = other DNA
                              organism = synthetic construct
SEQUENCE: 21
ttagctaatc ttcttgaaca gccgccagcc gctcac                                          36

SEQ ID NO: 22               moltype = RNA   length = 10
FEATURE                     Location/Qualifiers
misc_feature                1..10
                            note = Description of Artificial Sequence: Synthetic
                             oligonucleotide
source                      1..10
                            mol_type = other RNA
                            organism = synthetic construct
SEQUENCE: 22
gggttagggt                                                                       10

SEQ ID NO: 23               moltype = AA   length = 30
FEATURE                     Location/Qualifiers
source                      1..30
                            mol_type = protein
                            organism = Homo sapiens
SEQUENCE: 23
FVNQHLCGSH LVEALYLVCG ERGFFYTPNT                                                 30

SEQ ID NO: 24               moltype = AA   length = 10
FEATURE                     Location/Qualifiers
source                      1..10
                            mol_type = protein
                            note = Human immunodeficiency virus
                            organism = unidentified
SEQUENCE: 24
GRKKRRQRRR                                                                       10

SEQ ID NO: 25               moltype = AA   length = 11
FEATURE                     Location/Qualifiers
REGION                      1..11
                            note = Description of Artificial Sequence: Synthetic peptide
source                      1..11
                            mol_type = protein
                            organism = synthetic construct
SEQUENCE: 25
VSGWRLFKKI S                                                                     11

SEQ ID NO: 26               moltype = DNA   length = 420
FEATURE                     Location/Qualifiers
misc_feature                1..420
                            note = Description of Artificial Sequence: Synthetic
                             polynucleotide
source                      1..420
                            mol_type = other DNA
                            organism = synthetic construct
SEQUENCE: 26
catatgatgg aggtacagtt actggagagt gggggcgggt tggtccaacc aggtgggtcc  60
ctgcgtttgt cctgtgccgc atctgggttc acattcaact gggaattgat gggctgggca  120
cgccaagcac ccggcaaggg acttgagtgg gtctcgggaa ttgaagggcc ggggggatgtc  180
acctattatg cagattcagt aaagggccgg ttcacaattt cgcgtgacaa ttcgaaaaac  240
actctttact tgcagatgaa ctcacttcgg gcggaagaca cagctgtgta ttactgcgta  300
aaggtcggta aggacgccaa gtcggattac agaggccaag gaacgcttgt gacagtatca  360
agtgcctcaa cgtatccata tgacgtaccc gattatgcat gatagggtta gggtgtcgac  420

SEQ ID NO: 27               moltype = AA   length = 121
FEATURE                     Location/Qualifiers
REGION                      1..121
                            note = Description of Artificial Sequence: Synthetic
                             polypeptide
source                      1..121
                            mol_type = protein
                            organism = synthetic construct
SEQUENCE: 27
EVQLLESGGG LVQPGGSLRL SCAASGFTFN WELMGWARQA PGKGLEWVSG IEGPGDVTYY  60
ADSVKGRFTI SRDNSKNTLY LQMNSLRAED TAVYYCVKVG KDAKSDYRGQ GTLVTVSSAS  120
T                                                                    121

SEQ ID NO: 28               moltype = DNA   length = 36
FEATURE                     Location/Qualifiers
misc_feature                1..36
                            note = Description of Artificial Sequence: Synthetic
                             oligonucleotide
source                      1..36
```

```
                        mol_type = other DNA
                        organism = synthetic construct
SEQUENCE: 28
gtgagcggct ggcggctgtt caagaagatt agctaa                            36

SEQ ID NO: 29          moltype = RNA   length = 10
FEATURE                Location/Qualifiers
misc_feature           1..10
                       note = Description of Artificial Sequence: Synthetic
                        oligonucleotide
source                 1..10
                       mol_type = other RNA
                       organism = synthetic construct
SEQUENCE: 29
ggtgagcggc                                                         10

SEQ ID NO: 30          moltype = RNA   length = 10
FEATURE                Location/Qualifiers
misc_feature           1..10
                       note = Description of Artificial Sequence: Synthetic
                        oligonucleotide
source                 1..10
                       mol_type = other RNA
                       organism = synthetic construct
SEQUENCE: 30
gccgctcacc                                                         10

SEQ ID NO: 31          moltype = RNA   length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 31
ctaataggtt agggt                                                   15

SEQ ID NO: 32          moltype = DNA   length = 120
FEATURE                Location/Qualifiers
misc_feature           1..120
                       note = Description of Artificial Sequence: Synthetic
                        polynucleotide
misc_feature           1..120
                       note = This sequence may encompass 30-120 nucleotides
source                 1..120
                       mol_type = other DNA
                       organism = synthetic construct
SEQUENCE: 32
tttttttttt tttttttttt tttttttttt tttttttttt tttttttttt tttttttttt  60
tttttttttt tttttttttt tttttttttt tttttttttt tttttttttt tttttttttt  120

SEQ ID NO: 33          moltype = DNA   length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 33
tttttttttt tttttttttt tttttttttt                                   30

SEQ ID NO: 34          moltype = DNA   length = 60
FEATURE                Location/Qualifiers
misc_feature           1..60
                       note = Description of Artificial Sequence: Synthetic
                        oligonucleotide
source                 1..60
                       mol_type = other DNA
                       organism = synthetic construct
SEQUENCE: 34
tttttttttt tttttttttt tttttttttt tttttttttt tttttttttt tttttttttt  60

SEQ ID NO: 35          moltype = DNA   length = 90
FEATURE                Location/Qualifiers
misc_feature           1..90
                       note = Description of Artificial Sequence: Synthetic
                        oligonucleotide
```

-continued

```
source                    1..90
                          mol_type = other DNA
                          organism = synthetic construct
SEQUENCE: 35
tttttttttt tttttttttt tttttttttt tttttttttt tttttttttt tttttttttt   60
tttttttttt tttttttttt tttttttttt                                     90

SEQ ID NO: 36             moltype = DNA  length = 120
FEATURE                   Location/Qualifiers
misc_feature              1..120
                          note = Description of Artificial Sequence: Synthetic
                          polynucleotide
source                    1..120
                          mol_type = other DNA
                          organism = synthetic construct
SEQUENCE: 36
tttttttttt tttttttttt tttttttttt tttttttttt tttttttttt tttttttttt   60
tttttttttt tttttttttt tttttttttt tttttttttt tttttttttt tttttttttt   120

SEQ ID NO: 37             moltype = DNA  length = 150
FEATURE                   Location/Qualifiers
misc_feature              1..150
                          note = Description of Artificial Sequence: Synthetic
                          polynucleotide
source                    1..150
                          mol_type = other DNA
                          organism = synthetic construct
SEQUENCE: 37
tttttttttt tttttttttt tttttttttt tttttttttt tttttttttt tttttttttt   60
tttttttttt tttttttttt tttttttttt tttttttttt tttttttttt tttttttttt   120
tttttttttt tttttttttt tttttttttt                                     150

SEQ ID NO: 38             moltype = DNA  length = 10
FEATURE                   Location/Qualifiers
misc_feature              1..10
                          note = Description of Artificial Sequence: Synthetic
                          oligonucleotide
source                    1..10
                          mol_type = other DNA
                          organism = synthetic construct
SEQUENCE: 38
tttttttttt                                                            10

SEQ ID NO: 39             moltype = DNA  length = 10
FEATURE                   Location/Qualifiers
misc_feature              1..10
                          note = Description of Artificial Sequence: Synthetic
                          oligonucleotide
misc_feature              1..10
                          note = See specification as filed for detailed description
                          of substitutions and preferred embodiments
source                    1..10
                          mol_type = other DNA
                          organism = synthetic construct
SEQUENCE: 39
tttttttttt                                                            10

SEQ ID NO: 40             moltype = DNA  length = 12
FEATURE                   Location/Qualifiers
misc_feature              1..12
                          note = Description of Artificial Sequence: Synthetic
                          oligonucleotide
misc_feature              1..12
                          note = See specification as filed for detailed description
                          of substitutions and preferred embodiments
source                    1..12
                          mol_type = other DNA
                          organism = synthetic construct
SEQUENCE: 40
tttttttttt tt                                                         12

SEQ ID NO: 41             moltype = DNA  length = 13
FEATURE                   Location/Qualifiers
misc_feature              1..13
                          note = Description of Artificial Sequence: Synthetic
                          oligonucleotide
misc_feature              1..13
                          note = See specification as filed for detailed description
                          of substitutions and preferred embodiments
```

-continued

```
source                    1..13
                          mol_type = other DNA
                          organism = synthetic construct
SEQUENCE: 41
tttttttttt ttt                                                          13

SEQ ID NO: 42             moltype = DNA   length = 14
FEATURE                   Location/Qualifiers
misc_feature              1..14
                          note = Description of Artificial Sequence: Synthetic
                          oligonucleotide
misc_feature              1..14
                          note = See specification as filed for detailed description
                          of substitutions and preferred embodiments
source                    1..14
                          mol_type = other DNA
                          organism = synthetic construct
SEQUENCE: 42
tttttttttt tttt                                                         14

SEQ ID NO: 43             moltype = DNA   length = 15
FEATURE                   Location/Qualifiers
misc_feature              1..15
                          note = Description of Artificial Sequence: Synthetic
                          oligonucleotide
misc_feature              1..15
                          note = See specification as filed for detailed description
                          of substitutions and preferred embodiments
source                    1..15
                          mol_type = other DNA
                          organism = synthetic construct
SEQUENCE: 43
tttttttttt ttttt                                                        15

SEQ ID NO: 44             moltype = DNA   length = 16
FEATURE                   Location/Qualifiers
misc_feature              1..16
                          note = Description of Artificial Sequence: Synthetic
                          oligonucleotide
misc_feature              1..16
                          note = See specification as filed for detailed description
                          of substitutions and preferred embodiments
source                    1..16
                          mol_type = other DNA
                          organism = synthetic construct
SEQUENCE: 44
tttttttttt tttttt                                                       16

SEQ ID NO: 45             moltype = DNA   length = 20
FEATURE                   Location/Qualifiers
misc_feature              1..20
                          note = Description of Artificial Sequence: Synthetic
                          oligonucleotide
misc_feature              1..20
                          note = See specification as filed for detailed description
                          of substitutions and preferred embodiments
source                    1..20
                          mol_type = other DNA
                          organism = synthetic construct
SEQUENCE: 45
tttttttttt tttttttttt                                                   20

SEQ ID NO: 46             moltype = DNA   length = 15
FEATURE                   Location/Qualifiers
source                    1..15
                          mol_type = other DNA
                          organism = synthetic construct
misc_difference           3
                          note = The nucleotide base g can be repeated one or more
                          times
misc_difference           7
                          note = The nucleotide base g can be repeated one or more
                          times
misc_difference           11
                          note = The nucleotide base g can be repeated one or more
                          times
misc_difference           15
                          note = The nucleotide base g can be repeated one or more
                          times
```

-continued

```
misc_difference       4
                      note = n can be a,t,g or c and upto 6 nucleotide bases may
                       be added; wherein each nucleotide base may or may not be
                       different
misc_difference       8
                      note = n can be a,t,g or c and upto 6 nucleotide bases may
                       be added; wherein each nucleotide base may or may not be
                       different
misc_difference       12
                      note = n can be a,t,g or c and upto 6 nucleotide bases may
                       be added; wherein each nucleotide base may or may not be
                       different
SEQUENCE: 46
gggngggngg gnggg                                                          15

SEQ ID NO: 47         moltype = DNA   length = 12
FEATURE               Location/Qualifiers
source                1..12
                      mol_type = other DNA
                      organism = synthetic construct
SEQUENCE: 47
agggtaaggg ta                                                            12

SEQ ID NO: 48         moltype = DNA   length = 24
FEATURE               Location/Qualifiers
source                1..24
                      mol_type = other DNA
                      organism = synthetic construct
SEQUENCE: 48
agggtaaggg taagggtaag ggta                                               24

SEQ ID NO: 49         moltype = DNA   length = 24
FEATURE               Location/Qualifiers
source                1..24
                      mol_type = other DNA
                      organism = synthetic construct
SEQUENCE: 49
agggttaggg ttagggttag ggtt                                               24

SEQ ID NO: 50         moltype = RNA   length = 19
FEATURE               Location/Qualifiers
source                1..19
                      mol_type = other RNA
                      organism = synthetic construct
SEQUENCE: 50
ggtcatggga aagggcagg                                                     19

SEQ ID NO: 51         moltype = DNA   length = 11
FEATURE               Location/Qualifiers
source                1..11
                      mol_type = other DNA
                      organism = synthetic construct
SEQUENCE: 51
ggaggaggag g                                                            11

SEQ ID NO: 52         moltype = DNA   length = 23
FEATURE               Location/Qualifiers
source                1..23
                      mol_type = other DNA
                      organism = synthetic construct
SEQUENCE: 52
gggggggcg ggggaggccg ggg                                                 23

SEQ ID NO: 53         moltype = DNA   length = 11
FEATURE               Location/Qualifiers
source                1..11
                      mol_type = other DNA
                      organism = synthetic construct
SEQUENCE: 53
ggtggtggtg g                                                            11

SEQ ID NO: 54         moltype = RNA   length = 26
FEATURE               Location/Qualifiers
source                1..26
                      mol_type = other RNA
                      organism = synthetic construct
SEQUENCE: 54
gggacgaggg gttgttggga cgtggg                                             26
```

-continued

```
SEQ ID NO: 55           moltype = DNA   length = 11
FEATURE                 Location/Qualifiers
source                  1..11
                        mol_type = other DNA
                        organism = synthetic construct
SEQUENCE: 55
ggtggtgggg g                                                    11

SEQ ID NO: 56           moltype = DNA   length = 15
FEATURE                 Location/Qualifiers
source                  1..15
                        mol_type = other DNA
                        organism = synthetic construct
SEQUENCE: 56
ggttgggtag ggtgg                                                15

SEQ ID NO: 57           moltype = RNA   length = 11
FEATURE                 Location/Qualifiers
source                  1..11
                        mol_type = other RNA
                        organism = synthetic construct
SEQUENCE: 57
ggcggtggtg g                                                    11

SEQ ID NO: 58           moltype = RNA   length = 18
FEATURE                 Location/Qualifiers
source                  1..18
                        mol_type = other RNA
                        organism = synthetic construct
SEQUENCE: 58
ggggcgggtg gggagggg                                             18

SEQ ID NO: 59           moltype = DNA   length = 28
FEATURE                 Location/Qualifiers
source                  1..28
                        mol_type = other DNA
                        organism = synthetic construct
SEQUENCE: 59
ggatcctggg aaacaggcag aacttcgg                                  28

SEQ ID NO: 60           moltype = RNA   length = 30
FEATURE                 Location/Qualifiers
source                  1..30
                        mol_type = other RNA
                        organism = synthetic construct
SEQUENCE: 60
gggcaaatat tggcaattag ttggcagtgg                                30

SEQ ID NO: 61           moltype = RNA   length = 17
FEATURE                 Location/Qualifiers
source                  1..17
                        mol_type = other RNA
                        organism = synthetic construct
SEQUENCE: 61
ggttgggatt ggtgggg                                              17
```

PROGRAMMED DNA-DRIVEN SELF-ASSEMBLED RNA HYDROGEL

CROSS-REFERENCE TO RELATED APPLICATIONS

This application is a continuation-in-part of U.S. application Ser. No. 17/084,432, filed on Oct. 29, 2020, which claims priority to Korean Application No. 10-2019-0136416, filed Oct. 30, 2019, and Korean Application No. 10-2020-0077146, filed Jun. 24, 2020. Each of these applications is incorporated by reference in its entirety for all purposes.

REFERENCE TO A "SEQUENCE LISTING" SUBMITTED AS XML FILE VIA PATENT CENTER

The instant application contains a Sequence Listing which has been submitted electronically via Patent Center and is hereby incorporated by reference in its entirety. Said .xml copy, created on Jan. 25, 2024, is named 106739-1410652-000130US and is 82,187 bytes in size.

FIELD

The present invention relates to production of nucleic acids or polypeptides in a cell free system.

BACKGROUND

RNA is currently used in therapeutic applications that redirect mutated targets from proteins to RNA in the genome through the use of RNA interference. The unique ability of RNA moieties to serve both as a genetic source code and the catalytic repertoire makes them excellent drug targets beyond their use as a behavior blueprint for regulatory protein production. However, the practical applications of RNAs have been considerably limited due to its intrinsic chemical instability and low yield of production facilities.

Hydrogels are supra molecular assemblies hosting aqueous media, possessing both solute transport properties of a liquid and mechanical properties of a solid. Hydrogels are useful especially for biomedical applications because of their high water content, favorable structural features, and biocompatibility. Although nucleic acid hydrogels are generally known, the conventional methods for producing nucleic acid hydrogels typically require complicated procedures such as covalent crosslinking. As a result, these techniques were unable to produce RNA hydrogels with sufficient yield that is required for commercial production. The stability, mechanical performance, and functional properties of the current RNA hydrogels are also inadequate.

BRIEF SUMMARY

In some embodiments, disclosed herein a circular DNA template comprising (i) a promoter sequence and (ii) a sequence complementary to a first G-quadruplex motif.

In some embodiments, the promoter sequence is hybridized to a complementary nucleic acid sequence to form a first partially double-stranded DNA molecule; the first partially double-stranded DNA molecule comprises a double-stranded region and a single-stranded region; the double-stranded region comprises the first promoter sequence hybridized to the complementary nucleic acid sequence; and the single-stranded region comprises the sequence complementary to the first G-quadruplex motif.

In some embodiments, the circular DNA template further comprises a spacer, wherein the spacer comprises poly thymines (i.e., two or more thymines). In some embodiments, the first circular DNA template comprises a coding sequence of a polypeptide of interest. In some embodiments, the sequence complementary to the first G-quadruplex motif comprises a sequence of ACCCTAACCCTA (SEQ ID NO: 1). In some embodiments, the first promoter sequence is selected from the group consisting of a T7 promoter, a T3 promoter, a Lac promoter, an araBad promoter, a Trp promoter, a Tac promoter, and an SP6 promoter.

Also provided herein is a nucleic acid concatemer comprising a plurality of monomers, wherein each monomer comprises (i) a G-quadruplex motif, and (ii) a spacer comprising poly thymines or a coding sequence for a polypeptide of interest. In some embodiments, the nucleic acid concatemer is an RNA concatemer, wherein the G-quadruplex motif comprises UAGGGUUAGGGU (SEQ ID NO: 2). In some embodiments, the G-quadruplex motif comprises TAGGGTTAGGGT (SEQ ID NO: 20).

Also provided herein is a nucleic acid hydrogel comprising the nucleic acid concatemer of any of the embodiments above.

Also provided herein is a protein expression system comprising the nucleic acid hydrogel disclosed above, a ribosome, and/or a mixture of amino acids.

Also provided herein is a composition comprising a first circular DNA template and a second circular DNA template, wherein the first circular DNA template comprises (i) a first promoter sequence, (ii) a sequence complementary to a first G-quadruplex motif, and (iii) a spacer comprising poly thymines, wherein the second circular DNA template comprises (i) a second promoter sequence, (ii) a sequence complementary to a second G-quadruplex motif, and (iii) a coding sequence of a polypeptide of interest; and wherein the molar fraction of the first circular DNA template relative to the total amount of first and second circular DNA templates ranges from 25% to 75%.

In some embodiments, the first promoter sequence is hybridized to a complementary nucleic acid sequence to form a first partially double-stranded DNA molecule. The first partially double-stranded DNA molecule comprises a double-stranded region and a single-stranded region. The double-stranded region of the first partially double-stranded DNA molecule comprises the first promoter sequence hybridized to the complementary nucleic acid sequence, and the single-stranded region of the first partially double-stranded DNA molecule comprises the sequence complementary to the first G-quadruplex motif.

In some embodiments, the second promoter sequence is hybridized to a complementary nucleic acid sequence to form a second partially double-stranded DNA molecule. The second partially double-stranded DNA molecule comprises a double-stranded region and a single-stranded region. The double-stranded region of the second partially double-stranded DNA molecule comprises the second promoter sequence hybridized to the complementary nucleic acid sequence, and the single-stranded region of the second partially double-stranded DNA molecule comprises the sequence complementary to the second G-quadruplex motif.

In some embodiments, the first G-quadruplex motif and the second G-quadruplex motif comprise the same nucleotide sequence. The first promoter sequence and the second promoter sequence may comprise the same or different nucleotide sequence. In some embodiments, the spacer comprises 30-120 thymines (SEQ ID NO: 32). In some embodiments, the coding sequence has a length that is within a range from 20 to 300 nucleotides. In some embodiments, the length ratio of the coding sequence to the spacer is within a range from 1:0.2 to 1:2. In some embodiments, the polypeptide of interest is selected from the group consisting of insulin, Trans-activating transcriptional activator (TAT), HiBiT, and a single domain antibody.

The composition of any of the embodiments described above may further comprise one or more RNA polymerases, a mixture of ribonucleotides, and/or a buffer. In some embodiments, the composition further comprises a DNA polymerase having a strand replacement activity and thus is capable of performing a rolling circle amplification.

Also provided herein is a composition comprising a circular DNA template and a double-stranded DNA construct, and the circular DNA template comprises (i) a first promoter sequence, (ii) a sequence complementary to a first G-quadruplex motif, and (iii) a spacer comprising poly thymines. The double-stranded DNA construct comprises (i) a second promoter sequence, (ii) a sequence complementary to a second G-quadruplex motif, and (iii) a coding sequence of a polypeptide of interest.

Also provided herein is a nucleic acid hydrogel comprising a first nucleic acid concatemer and a second nucleic acid concatemer. The first nucleic acid concatemer is produced by rolling circle transcription or amplification of the first circular DNA template provided in this disclosure, and the second nucleic acid concatemer is produced by rolling circle transcription or amplification of the second circular DNA template provided in this disclosure.

Also provided herein is a nucleic acid hydrogel comprising a first RNA molecule and a second RNA molecule, wherein the first RNA molecule comprises (i) a first G-quadruplex motif, and (ii) a spacer comprising poly adenines (i.e., two or more adenines), and wherein the second RNA molecule comprises (i) a second G-quadruplex motif, and (ii) a coding sequence for a polypeptide of interest.

In some embodiments, the first RNA molecule is an RNA concatemer comprising a plurality of monomers and wherein each monomer comprising the first G-quadruplex motif, and the spacer comprising poly adenines or a coding sequence for a polypeptide of interest.

Also disclosed herein is a protein expression system comprising any nucleic acid hydrogel disclosed herein, a ribosome, and/or a mixture of amino acids.

Also disclosed herein is a kit for expressing a polypeptide of interest, and the kit comprises (1) a first DNA molecule capable of forming a first circular DNA template by hybridizing to a first splint oligonucleotide, wherein the first circular DNA template comprises (i) a first promoter sequence, (ii) a sequence complementary to a first G-quadruplex motif, and (iii) a spacer comprising poly thymines, (2) the first splint oligonucleotide that is complementary to the first promoter sequence, wherein the first DNA template can hybridize to first splint oligonucleotide and be circularized to form a first circular DNA template, and/or (3) a second DNA molecule capable of forming a second circular DNA template by hybridizing to a second splint oligonucleotide, wherein the second circular DNA template comprises (i) a second promoter sequence, (ii) a sequence complementary to a second G-quadruplex motif, and (iii) a coding sequence of the polypeptide of interest, and (4) the second splint oligonucleotide that is complementary to the second promoter sequence, wherein the second DNA template can hybridize to the second splint oligonucleotide and be circularized to form a second circular DNA template.

In some embodiments, the kit comprises any composition comprising a first circular DNA template and second circular DNA template as disclosed herein. In some embodiments, the first G-quadruplex motif and the second G-quadruplex motif have the same or different sequence. In some embodiments, the first promoter sequence and the second promoter sequence are the same or different. In some embodiments, the spacer comprises 30-120 thymines (SEQ ID NO: 32). In some embodiments, the coding sequence has a length that ranges from 20 to 300 nucleotides. In some embodiments, the length ratio of the coding sequence to the spacer is within a range from 1:0.2 to 1:2. In some embodiments, the polypeptide of interest is selected from the group consisting of insulin, HiBiT, a Trans-activating transcriptional activator (TAT), and a single domain antibody. In some embodiments, the kit further comprises one or more DNA ligases, RNA polymerases, a mixture of ribonucleotides, and/or one or more buffers. In some embodiments, the kit further comprises a DNA polymerase having a strand replacement activity and thus is capable of performing a rolling circle amplification.

Also disclosed herein is a method of preparing a nucleic acid hydrogel comprising: (1) providing a first circular DNA template comprising (i) a first promoter sequence, and (ii) a sequence complementary to a first G-quadruplex motif; and (2) performing a rolling circle transcription or amplification on the first circular template to produce a first nucleic acid concatemer, wherein the first nucleic acid concatemer forms a nucleic acid hydrogel.

In some embodiments, the first circular DNA template further comprises a spacer comprising poly thymines, wherein the step (1) further comprises providing a second circular DNA template comprising (i) a second promoter sequence, (ii) a second G-quadruplex motif, and (iii) a coding sequence of a polypeptide of interest, and wherein the step (2) further comprises performing a rolling circle transcription or amplification of the second circular DNA template to produce a second nucleic acid concatemer, wherein the first and second nucleic acid concatemers form the nucleic acid hydrogel.

Also disclosed herein is a method for producing a protein in a cell-free synthesis system, and the method comprises combining any of the nucleic acid hydrogels disclosed herein with a cell-free synthesis system under conditions permitting translation of the polypeptide of interest. In some embodiments, the cell-free synthesis system comprises a ribosome and/or a mixture of amino acids.

BRIEF DESCRIPTION OF THE DRAWINGS

FIG. 1A shows the schematic framework of the self-assembly process by which RNA moieties formed RG4s through RCT. A circular DNA comprising a sequence complementary to a G-quadruplex ("G4") motif and functional sequences suitable for user-prescribed applications was used as a template for the RCT. The relative positions and sequences of the crosslinker region and the functional sequences may vary. Tandemly repeated long single-stranded RNAs (RNA concatemers) synthesized from the RCT with repeated G-quadruplex motifs serve as an ideal scaffold for 3-D hydrogel assemblies. FIG. 1B is a pictorial representation of the RCT products with respect to gelation time (0, 48 hours for RGx concatemer and 0, 3, 6, 9, 12, 24, 48 hours for RG4 concatemer from left to right). White arrows denote the location of the RCT products (gel phase in RG4 hydrogel and solution phase in RGx solution). FIG. 1C shows RG4 hydrogels patterned in various polygonal molds; scale bar indicates 10 mm. FIG. 1D shows a side view of the RG4 hydrogel fabricated in a 3-D cylindrical mold; scale bar indicates 5 mm. FIG. 1E shows a confocal microscopic image of the RG4 hydrogel (scale bar: 60 μm) stained with SYBR green II to show the pores and repetitive micro structures. FIG. 1F shows FE-SEM images of freeze-dried RG4 hydrogel with scale bar of 100 μm. FIG. 1G is the zoomed-in view of a portion of FIG. 1F, where the scale bar indicates 20 μm.

FIG. 2A shows a circular dichroic (CD) analysis of sG4s and sGxs containing a half-unit of the G4 and scrambled G4 motif (non-G4) as an RCT product under various salt conditions. Distinct positive peak at 262 nm and a trench at 240 nm for sG4 when subjected to a condition of 100 mM KCl and NaCl demonstrate alteration in the secondary structure, a phenomenon known associated with formation of hydrogel, where no changes were observed for the sGx, 'no-salt' and 100 mM MgCl₂. FIG. 2B shows fluorescence spectrum of thioflavin T (ThT) upon interaction with sG4 and sGx where significant enhancement in fluorescent intensity was observed exemplifying specific binding of ThT probe to the RG4s (inset graphic). sG4 had 7.1-fold enhancement when compared with sGx displaying poor selectivity for ThT, with a statistical P value of 0.001 in a t-test. FIG. 2C shows the comparison of enzymatic activities facilitated by RG4 and RGx for the oxidation of $ABTS^{2-}$ to $ABTS^{-}$ (figure inset) when complexed with hemin at pH 5.4. Both the RG4 and the RGx increased the peroxidase activity of heme, possibly due to interaction between hemin and the self-enclosed conserved modules of RG4 and RGx. however, the peroxidase activity of Hemin complexed with RG4 gels increased more rapidly.

FIG. 3A shows stress-versus-strain curves of the RG4 gel and RGx, which were subjected to compression test on a universal tensile machine. FIG. 3B shows the storage modulus for the RG4 gel and RGx with respect to fabrication time, analyzed rheologically at the rotation angular frequency of 50.12 rad/s. FIG. 3C shows the water retention and absorption capacity of freshly prepared and rehydrated RG4 hydrogels, respectively. FIG. 3D shows the experimental and theoretical evaluation of ThT diffusion into the hydrogel. The six images from left to right or the confocal microscopic images at 260 s interval. Theoretical assumptions 1 and 2 (also referred to as theoretical estimations 1 and 2 in this disclosure) about ThT and ribosomes were validated to estimate their diffusion velocities. FIG. 3E shows microscopic image from the AFM analysis to estimate the pore size of the RG4. FIG. 3F is the magnified AFM image which clearly represents the porous nature. The scale bars in the main and magnified figure indicates 200 nm and 50 nm, respectively.

FIG. 4A shows a pictorial representation of RCT products in serum for stability study. Quantitative estimation of RNA quantity in the RG4 network (from the bottom) and in the supernatant (dissociation product of the RG4 hydrogel). Exposure time-based degradation of the post-annealed transcription products in FBS was analyzed from the band intensities of the gel images for RG4 supernatant (FIG. 4B) and RG4 (FIG. 4C) at different times. The arrow indicates the start of RG4 degradation. RNA degradation was observed for RG4 supernatant indicated by diminished RNA quantity at 48 hour (FIG. 4D). FIG. 4E shows the half-life of the RNA molecules attributable to the serum was estimated using the band intensities, where RGx had a faster degradation than RG4. FIG. 4F shows a time-based quantitative gel electrophoresis evaluation of the RG4 hydrogel and RGx. G4 formation in the RG4 was expected to elongate the RNA synthesis time and the total amount of synthesized RNA.

FIG. 5A-5D show a pictorial representation of the protein expression system and the translation yield for the proteins expressed. FIG. 5A shows a sketch of the protein expression process from the RG4 hydrogel template. The cut-out RG4 hydrogel was added to the cell-free protein expression lysate mix with ribosome. FIG. 5B shows the relative quantity of HiBiT peptide expressed from the DNA and RNA templates, which are characterized by the generated relative luminescence (RL) signals. *RNA indicates the cut-out W-RG4 hydrogel. The annealed RG4 expressed a lower yield because it lost its hydrogelation. FIG. 5C shows the relative quantity of TAT and insulin expressed using various templates, as characterized by the RL of cut-out and urea-treated translation products. FIG. 5D shows the comparison of the uncoupled translation using wheat germ cell-free expression system for HiBiT expressed proteins with fRNA and W-RG4 hydrogel. W-RG4 150 represents the volume of the translation reaction mixture was 150 μl, where 8-fold increase in yield was observed.

FIG. 5E. discloses "60 T" as SEQ ID NO: 34.

FIG. 5I compares the HiBiT expression from various lysate-embedded W-RG4s with lysate-free W-RG4s under different template preparation conditions. A W-RG4 hydrogel produced using a HiBiT template combined with a spacer template for 150T W-RG4 in the presence of embedded lysate showed the highest protein expression after a 3-hour transcription reaction (gel formation) followed by a 2-hour translation. The expression level was higher than that of lysate-free W-RG4. FIG. 5I discloses "30T" as SEQ ID NO: 33, "90T" as SEQ ID NO: 35, and "150T" as SEQ ID NO: 37. FIG. 5J shows the results of HiBiT expression from lysate-free W-RG4 hydrogel and lysate-embedded W-RG4 hydrogels. Lysate-embedded hydrogel (L-gel) successfully expressed HiBiT without further addition of lysate components to the translation reaction mixture. Additional lysate added to the translation reaction mixture further boosted the HiBiT expression of the lysate-embedded hydrogel (L-L-gel).

FIG. 6A is a schematic illustration of the fabrication of the DNA rolling circle transcription (RCT) template followed by the transcription of the RNA product. The precursor template, containing a complementary strand for the T7 promoter primer, a G-quadruplex crosslinking sequence, and the poly T spacer, was annealed to form a partial double strand in the T7 promoter region. The successfully ligated templates could participate in the transcription of long and repetitive RNA strands with G-quadruplexes (RG4) initiated by the T7 promoter. FIG. 6B shows the PAGE analysis of bare, annealed, and ligated precursor templates for 30T RG4, 30T RGx, and various thymine spacers (3T, 10T (SEQ ID NO: 38), 30T (SEQ ID NO: 33), 60T (SEQ ID NO: 34), 90T (SEQ ID NO: 35), and 120T (SEQ ID NO: 36)). As a huge network, the RG4 gel did not migrate, whereas the non-gelating RGx product migrated marginally. The difference in band migration ensured successful formation of templates with different spacers at each step of fabrication. Filled-in rhombi (♦) indicate successful fabrication of the samples. Spacer lengths of 3T and 10T (SEQ ID NO: 38) failed to synthesize the circular DNA template, as indicated by vacant rhombi (◇), whereas spacer lengths of 30T (SEQ ID NO: 33) and above displayed a significant difference in band migration. 3T was far from the rest of the bands, which could indicate a long linear DNA template, and its RNA product was only mildly gelated. FIG. 6C shows the gelation of RG4s with spacer of various lengths, which was evaluated through vial inversion tests. RG4s with spacer lengths of 3T and 10T (SEQ ID NO: 38) were non-gelating (denoted by downward arrow) because the steric length was inadequate to allow linear DNA to circularize, whereas spacer lengths of 30T (SEQ ID NO: 33) and above were long enough to allow circular templates to form and gelation (denoted by upward arrows). FIG. 6D shows the concentration of total RNA during transcription derived from templates with various spacer lengths. Though circular DNA templates were not fabricated for 3T and 10T (SEQ ID NO: 38), the RNA transcription yield for 3T was as large as that from circular templates. FIG. 6A-6D disclose "10T" as SEQ ID NO: 38, "30T" as SEQ ID NO: 33, "60T" as SEQ ID NO: 34, "90T" as SEQ ID NO: 35, and "120T" as SEQ ID NO: 36.

FIG. 8A shows the schematic of the AFM tip scanning the surface of RG4 gels fabricated on a mica substrate to obtain topological images in an intermittent contact mode. A small tip held at the end of a cantilever scans the surface of interest, causing attenuation of the oscillation amplitude and thereby producing a topographical image. FIGS. 8B, 8C, 8D, and 8E shows the AFM images of RNA molecules with varying spacer lengths of 30T (SEQ ID NO: 33), 60T (SEQ ID NO: 34), 90T (SEQ ID NO: 35), and 120T (SEQ ID NO: 36), respectively were self-assembled during the RCT process and displaying morphological differences in the pore size. The gels became more flexible as spacer length increased, and pore size also increased with spacer length. The scale bar indicates 200 nm. FIGS. 8F, 8G, and 8H show the histograms signifying the pore size (area) distribution of RG4 gels with 30T (SEQ ID NO: 33), 60T (SEQ ID NO: 34), and 120T (SEQ ID NO: 36), respectively were analyzed using ImageJ software and the AFM images.

FIGS. 9A and 9B show the confocal microscope images of the RG4 gel. FIG. 9A shows the confocal microscope images of an RG4 gel loaded with SYBR green II. The samples were fabricated on the micrometer-scale, as indicated by the arrows (the short and long widths mentioned in the figure are 69.1 and 128.4 μm, respectively). FIG. 9B shows the 3-D confocal microscopic image of the RG4 gel fabricated on the centimeter-scale. A periodic interconnected porous structure is evident, indicating the formation of hydrogel. The scale bars indicate 50 μm.

FIG. 10 shows the Field-Emission Scanning Electron Microscope (FE-SEM) image of the RGx. The RGx possessed a flat, impeccable morphology without pores and could not form a hydrogel. The scale bar indicates 100 μm.

FIGS. 13A, 13B, 13C, and 13D show results of the investigation for self-biotinylation of the RCT products during peroxidase activity through AFM images. G-quadruplexes catalyzed by hemin in the presence of $H_2O_2$ and biotin tyramide were investigated for self-biotinylation (45). To identify the biotinylated sites in the RG4 and RGx, streptavidin was added because it selectively binds to self-biotinylated sites in the G4 regions. AFM images were captured before and after treatment with the catalytic reagents, and their sectioned heights were assessed. Sectioned height differences due to streptavidin binding (identified as bright spots) on bare and treated RCT products were measured to confirm the binding of streptavidin to the biotinylated sites. The average step height variations for bare and treated RG4s were 6.6 nm and 22.9 nm, respectively. Although streptavidin binding was not uniform, the presence of streptavidin at the G4 precincts was confirmed from the morphology. The surface morphology of RGx exhibited no pores and a height variation of 30-40 nm for bare and treated samples. This confirmed the absence of G-quadruplexes because no self-biotinylation or streptavidin binding occurred. The scale bar indicates 200 nm.

FIG. 14A shows the force curve obtained using the AFM indentation method, which measures the indentation depth on the nanometer scale. The elastic modulus was obtained using the Hertz fitting model at its best fit region. FIG. 14B shows the Young's modulus of the RCT products was obtained from force mode with respect to gelation time. At 0, 3, and 6 hours, the modulus was close to zero, which indicates that, although gelation did not begin after 6 hours, the modulus increased shadowing the gel characteristics. Time-dependent resistance to the force applied was noticed. The modulus for the RGx products remained zero over all the time intervals tested. FIG. 14C and FIG. 14D show the storage modulus, which describes the elastic portion of the material and solid-state behavior, and the loss modulus, which characterizes the viscosity of a sample and liquid-state behavior, respectively (46). The RG4 gel exhibited non-Newtonian, nonlinear behavior, with concave patterns in both storage and loss moduli with various fabrication times and a wide range of angular frequencies. The RG4 gel exhibited a large storage modulus and low loss modulus, indicating a solid-like nature. A gradual increase in both moduli was observed, and the response was reduced greatly beginning 12 hours after fabrication. The moduli for RGx were close to zero, indicating its viscosity.

FIG. 16A shows the reaction time-based stability of the post-annealed transcription products in the FBS environment was evaluated quantitatively by agarose gel electrophoresis. RNA degradation was observed in both RG4 and RGx, as indicated by diminished RNA quantity at 48 h. An abundance of RNA molecules in the RG4 and lability in the RGx was observed. FIG. 16B shows the extended exposure of RGx towards serum which degraded for a period of 48 h. The arrow indicates the start of RGx degradation.

FIG. 17A shows the comparison of the HiBiT-encoding RG4 (H-RG4) and RGx (H-RGx) products fabricated in a glass vial, which was inverted to confirm hydrogelation. In contrast to the RNA concatemer transcribed from the DNA template comprising the 30T spacer (SEQ ID NO: 33) and the sequence complementary to the G-quadruplex motif, which hydrogelates to form the 30T RG4 hydrogel, the HiBiT-encoding RCT products did not show macroscopic evidence of hydrogelation and stuck to the bottom of the vial. An upward arrow indicates a formed gel, and a downward arrow indicates a liquid that failed to gelate. FIG. 17B shows the PAGE analysis of circular template formation for the HiBiT-G4 and HiBiT-Gx templates. Different migration positions are visible depending on fabrication step, although hydrogelation was unsuccessful. Successfully fabricated templates from each process are indicated with filled-in rhombi (◆). FIG. 17C shows the expected secondary structures in H-RG4 that are thought to hinder hydrogel formation. The failure of hydrogelation might have occurred as a result of complex secondary structure formation among the H-RG4s that hampered the interactions with the G4 motifs. The probabilities of structure 1 and 2 formation were estimated by oxDNA to be 96.48% and 25.39%, respectively. The G-quadruplex moiety is labeled in gray. FIG. 17C discloses SEQ ID NOS 29-31, respectively, in order of appearance. FIG. 17D shows the protein expression efficiency of various HiBiT-encoding RNA templates was characterized by relative luminescence (RL) from the HiBiT peptide. The H-RG4 product seems to be non-hydrogelating and exhibited no difference in protein expression efficiency from the H-RGx. The protein expression yield of H-RG4 tend to decline more when annealed than the H-RGx, possibly due to G4 formations. The occurrence probabilities of structures 1 and 2 were estimated through the oxDNA coarse-grained, molecular dynamic simulation model using the operating conditions given in Table 1 below. Partial complementary bonds upon one cycle of RCT production are suspected to hinder hydrogelation of RG4 due to steric hindrance from rigid, unspecific secondary structures. This hindrance was suppressed by incorporating the supportive RG4, which behaved as a wide band.

TABLE 1

| Simulation Conditions | |
| --- | --- |
| Simulation type | Molecular dynamics (MD) |
| Backend | CUDA |
| Interaction type | DNA2 |
| Salt concentration | 1M |
| Temperature | 37° C. |
| Time interval (dT) | 0.001 oxDNA time unit |
| Simulation data print out interval (step) | $1.00 \times 10^4$ |

TABLE 1-continued

| Simulation Conditions | |
| --- | --- |
| Simulation type | Molecular dynamics (MD) |
| Total simulation steps | $1.00 \times 10^9$ |
| Used sequence dependent file | oxDNA2_sequence_ dependent_parameters.txt |
| External force (mutual trap) | Off |

Figure 18A:
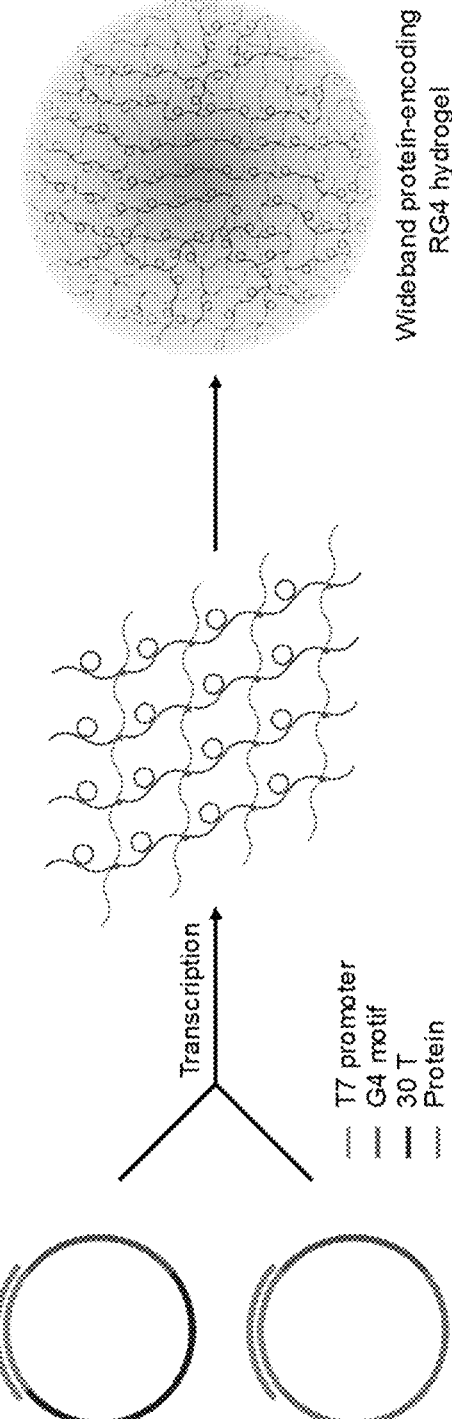
Figure 18C:
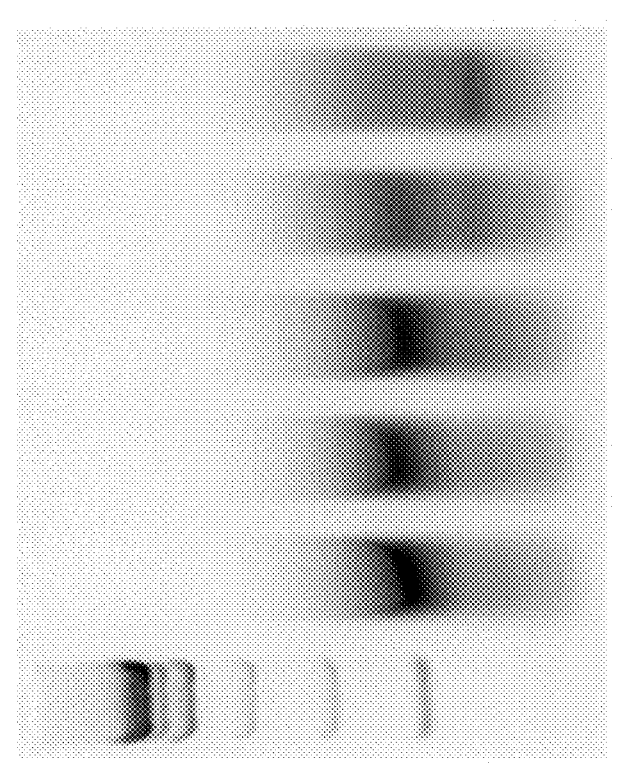
Figure 18B:
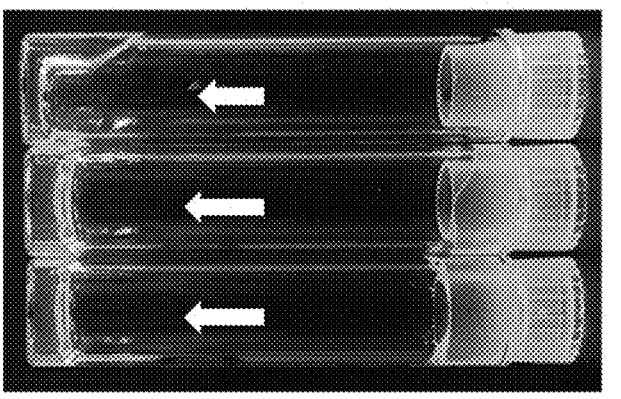
Figure 18E:
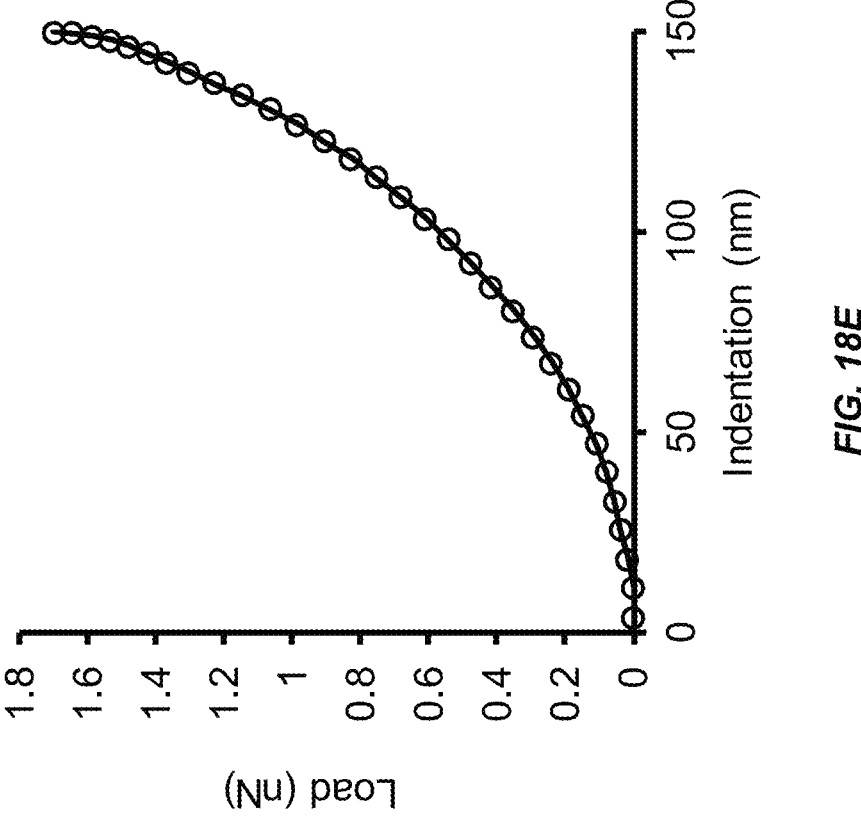
Figure 18D:
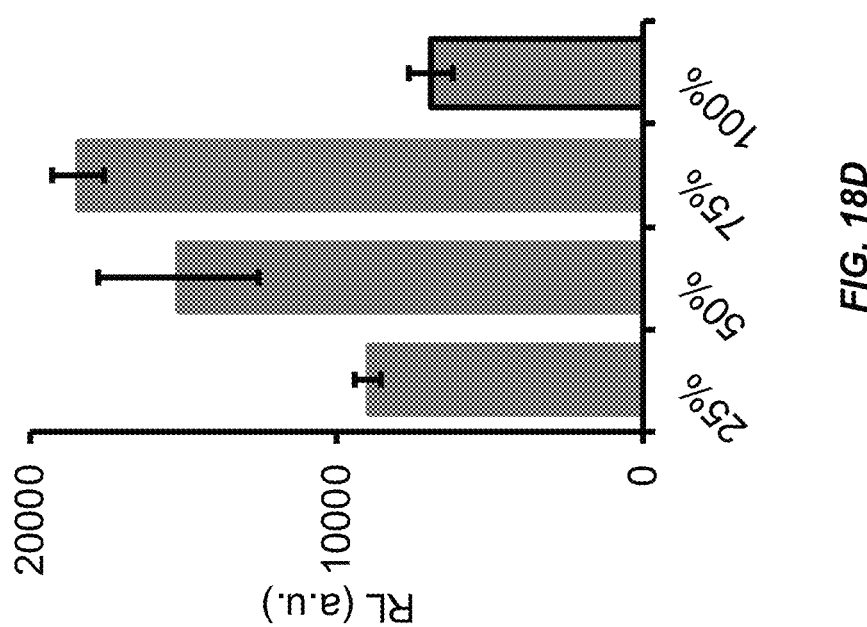

FIG. 18A-18E illustrate a wideband system that can be used to hydrogelate RCT products. FIG. 18A is a schematic representation of the wideband RG4 hydrogel (W-RG4) fabrication. To maximize the advantages of the pro-grammed, self-assembled RG4 hydrogel for protein expres-sion, we designed a method that enables hydrogelation of previously non-hydrogelating RCT products through a hydrogelated RG4 component. Those products were shown to form a stable hydrogel (W-RG4) similar to the 30T RG4 hydrogel (a hydrogel formed by an RNA concatemer pro-duced from rolling circle transcription of a DNA template have the sequence of SEQ ID NO: 6). FIG. 18A discloses "30T" as SEQ ID NO: 33. FIG. 18B shows the formation of W-RG4s with different molar fractions of 30T RG4 was checked for hydrogelation by vial inversion and transcribed simultaneously. The indicated molar fraction (25%, 50%, and 75%) refer to the molar fraction of the spacer template, 30T RG4. Although the protein-encoding RG4 templates (H-RG4) appeared to be non-hydrogelating, the embedded G-quadruplex interacted with the moieties in the supporting RG4 products to produce a successful hydrogel. As expected, the rigidity of the hydrogel decreased when the molar fraction of H-RG4 increased and the molar fraction of 30T RG4 decreased. FIG. 18C shows an agarose gel elec-trophoresis analysis of the wideband-RNA hydrogel after annealing. The HiBiT-encoding RG4 hydrogel showed a rapid and improved expression pattern from the transcription stage, and the RNA disappeared when the molar fraction of the G-quadruplex-forming entity decreased. The hydroge-lating RG4s migrated to a lesser extent than the non-hydrogelating 100% H-RG4 due to the cross-linked G4s. FIG. 18D shows the protein expression efficiency of the W-RG4 hydrogel was characterized using the relative lumi-nescence (RL) signal from the expressed HiBiT. The hydrogelated W-RG4 displayed increased efficiency com-pared with 25% and 100% H-RG4. The protein production yield was maximized at the molar fraction of 75%. FIG. 18E shows the force curve obtained from the nano-indentation measurement of the 75% W-RG4 using AFM. Young's modulus was estimated to be 9.71 kPa in the best fit region.

Figure 19:
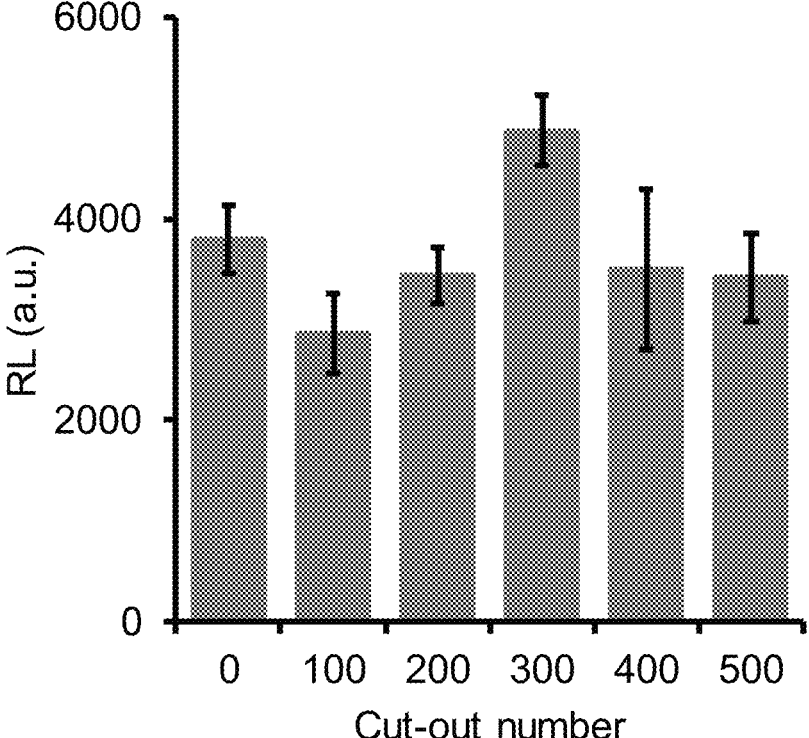

FIG. 19 shows protein expression efficiency of the W-RG4 having different cut-out numbers. Optimization of protein expression from the W-RG4 was performed by cutting the hydrogel to improve the approachability of the translation components. The efficiency was maximized when the number of cuts was 300, which significantly enhanced protein efficiency in contrast to the uncut samples by mimicking a thin hydrogel pad (33) to facilitate diffusion of enzymes and substrates involved in protein expression.

Figure 20:
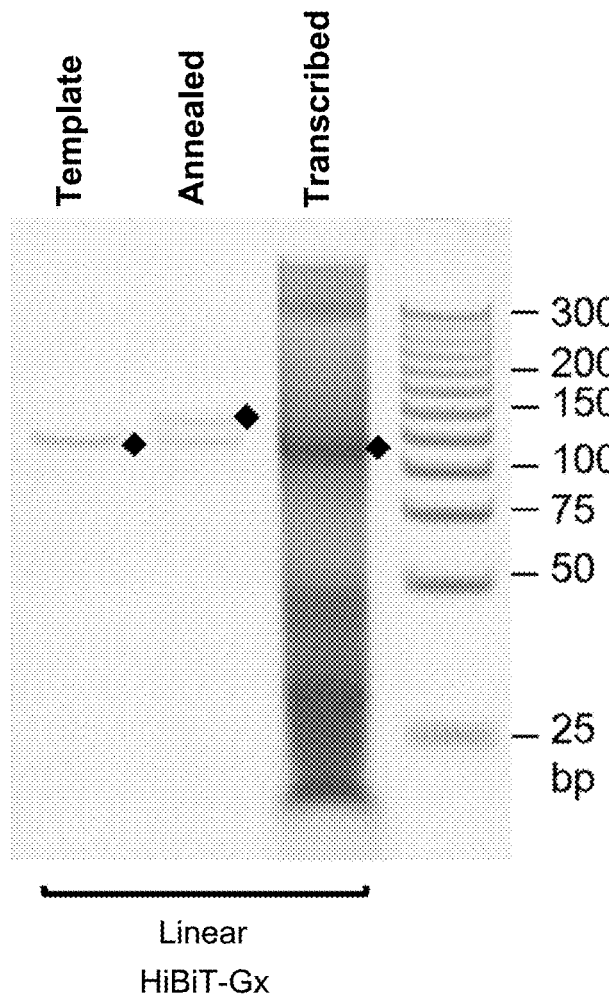
Figure 21A:
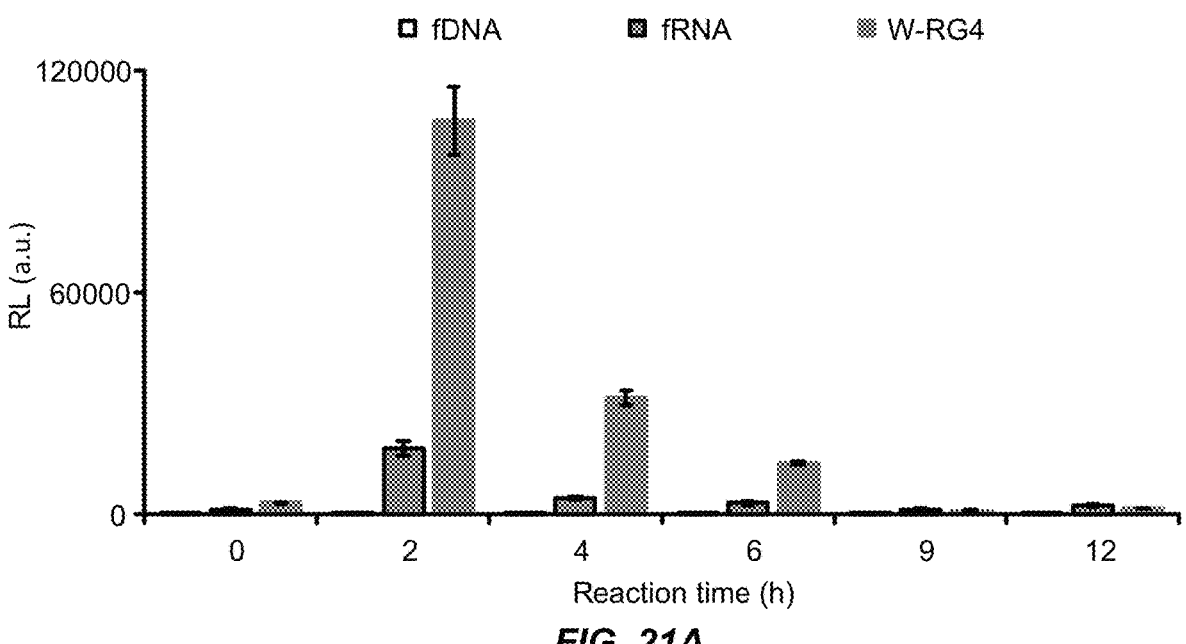
Figure 21B:
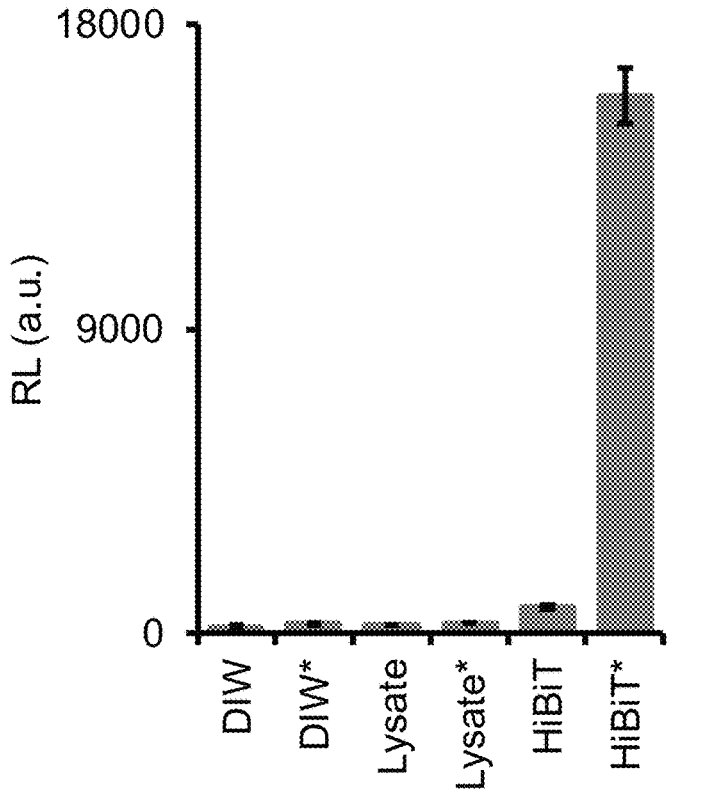
Figure 21C:
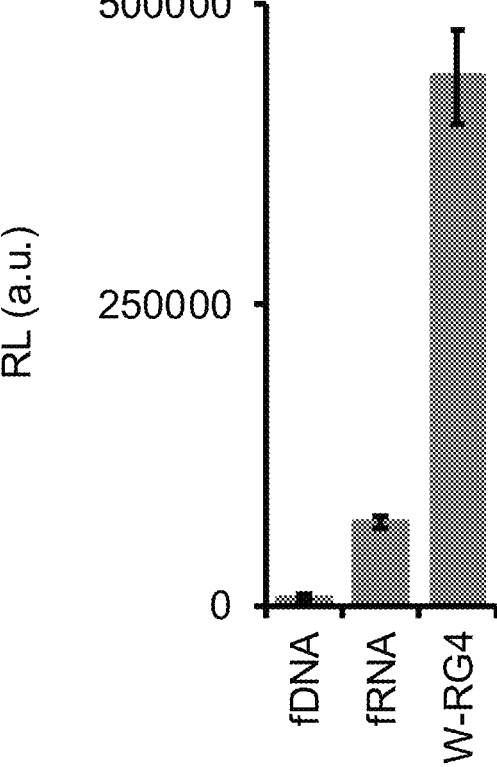
Figure 21D:
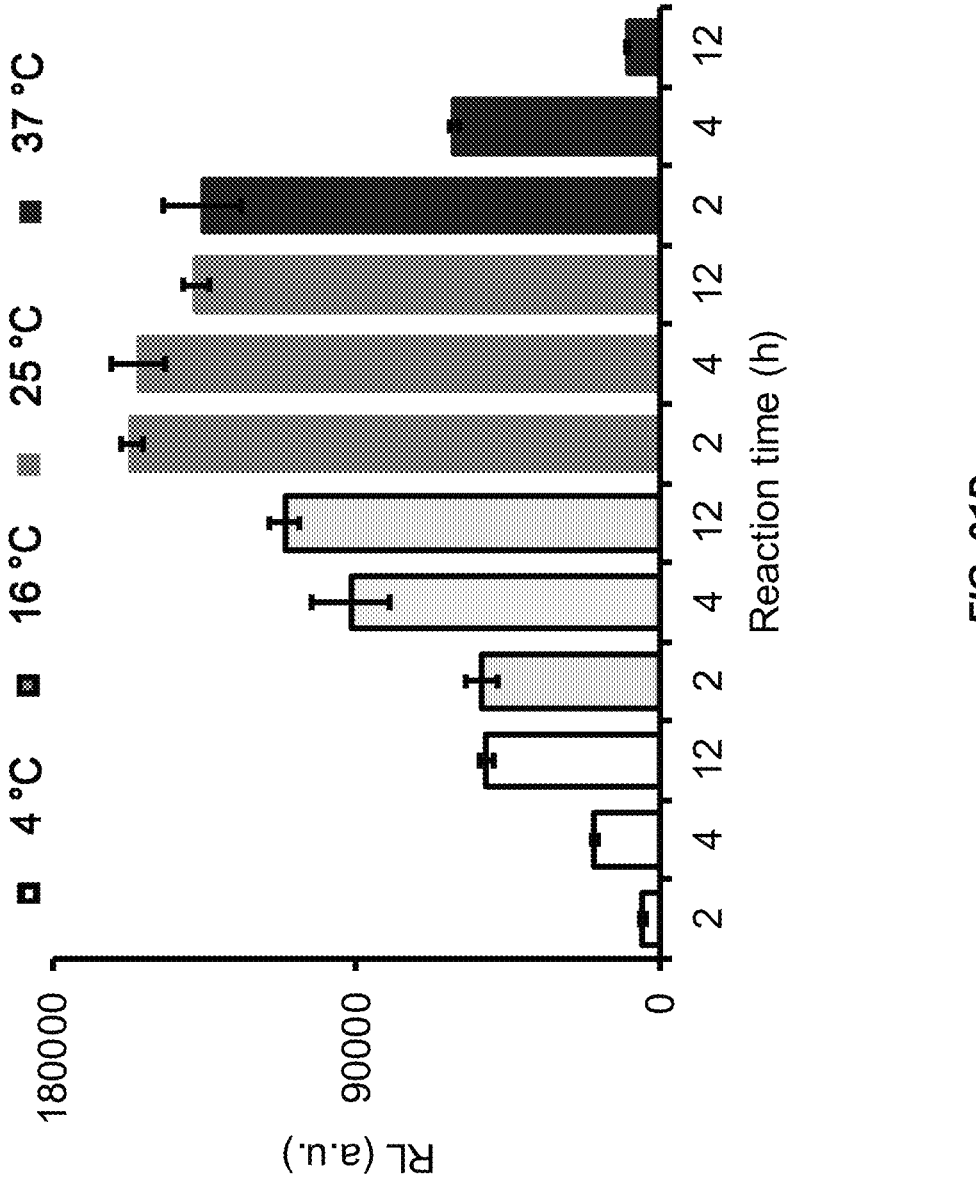
Figure 21E:
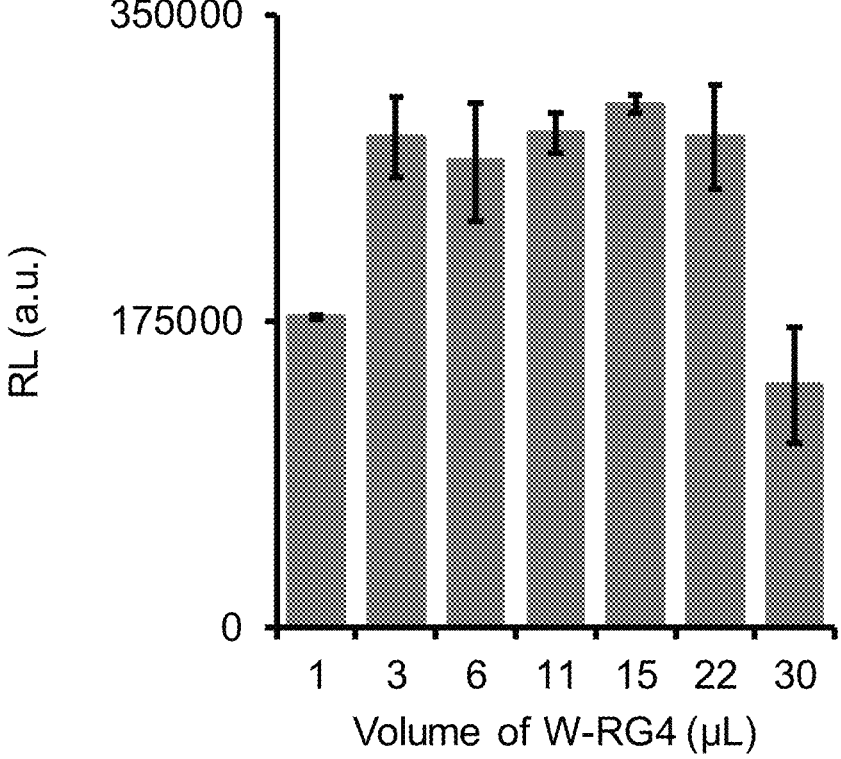

FIG. 20 shows the PAGE analysis for stepwise fabrication of a linear HiBiT-Gx template and transcribed RNA. Dis-tinguishable differences in band positions of the templates were witnessed for the linear HiBiT template before and after annealing with the T7 promoter. The linear HiBiT-Gx RNA was transcribed from the annealed linear HiBiT-Gx template, which displayed a distinct band at the location of the DNA template. Residual bands are also visible due to instant degradation of transcribed RNA. The filled-in rhombi (◆) indicate successfully fabricated templates or transcribed RNA in each step.

FIG. 21A-21E show optimization of reaction parameters for enhanced protein expression: reaction time, chaotropic treatment, reaction temperature, and template quantity. (FIG. 21A) Comparison of the relative luminescence ("RL") for free DNA (fDNA) and RNA (fRNA) with the W-RG4 with respect to reaction time. Although the performance of the W-RG4 was superior to that of the other templates, decreasing RL, which corresponds to a decreasing amount of soluble HiBiT, was observed as the translation reaction time exceeded 2 hours. Interference of inclusion bodies among the expressed HiBiT peptides was suspected. (FIG. 21B) The RL of the HiBiT-translated products before and after urea treatment for solubilization of aggregated pep-tides. DIW, lysate, and HiBiT correspond to distilled water, translation mix without any template, and HiBiT-translated mixture, respectively. DIW*, Lysate*, and HiBiT* indicate urea-treated samples. A significant increase in RL was observed after the urea treatment for the translation product. (FIG. 21C) The relative quantity of expressed HiBiT peptide from various templates as characterized by RL after urea treatment of the translation products. (FIG. 21D) Tempera-ture-dependent expression yield of HiBiT with respect to RL. The time-dependent decrease in RL caused by the inclusion bodies was not observed below 37° C., and opti-mal expression was achieved at 25° C. (FIG. 21E) Influence of various RNA template volumes with respect to protein efficiency yield. Consistent yield was observed when using 3 to 22 µl of the RCT products for the translation.

Figure 22A:
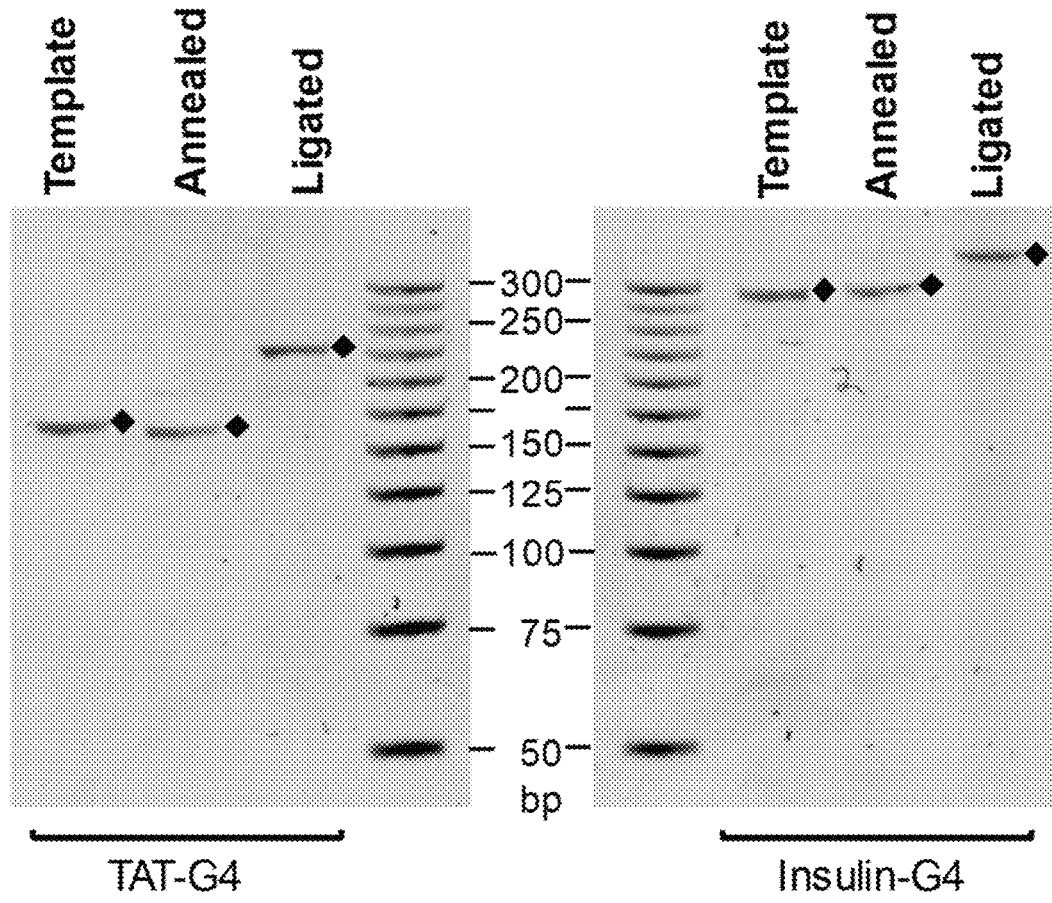
Figure 22B:
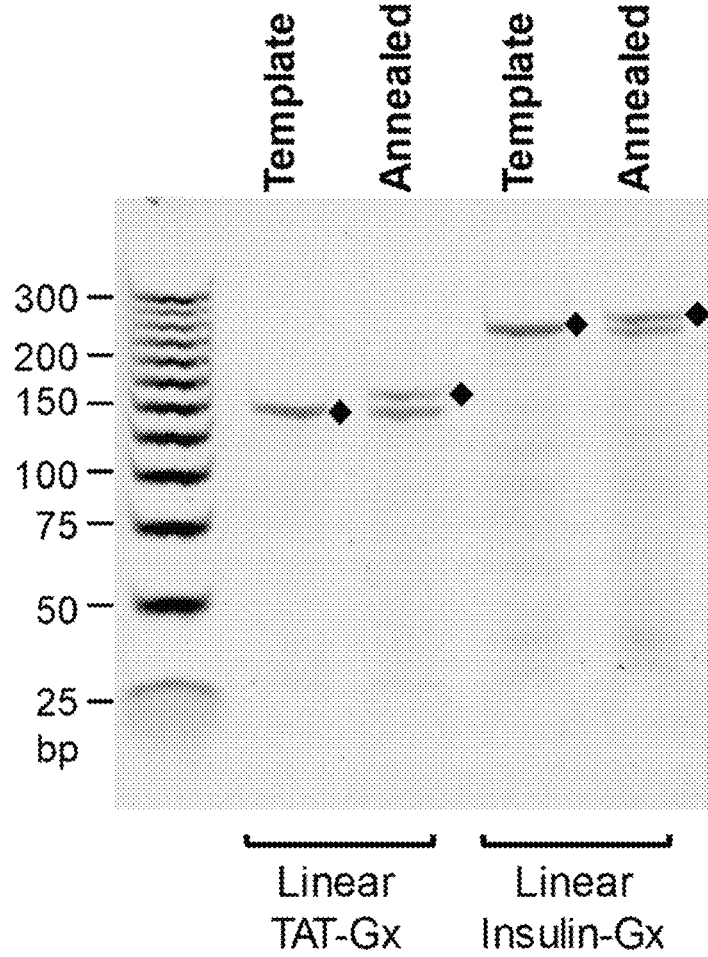

FIG. 22A-22B show the PAGE analysis of HiBiT-tagged TAT and insulin G-quadruplex templates. FIG. 22A shows the fabrication of the HiBiT-tagged TAT and insulin G-qua-druplex encoding circular templates. A distinguishable dif-ference in band migration for the sequential process was observed, indicating successful circularization and ligation of the templates. FIG. 22B shows the linear HiBiT-tagged TAT and insulin scrambled G-quadruplex templates dis-played an apparent difference in the band migration before and after annealing. All filled-in rhombi (◆) indicate suc-cessfully fabricated templates in each step.

Figure 23:
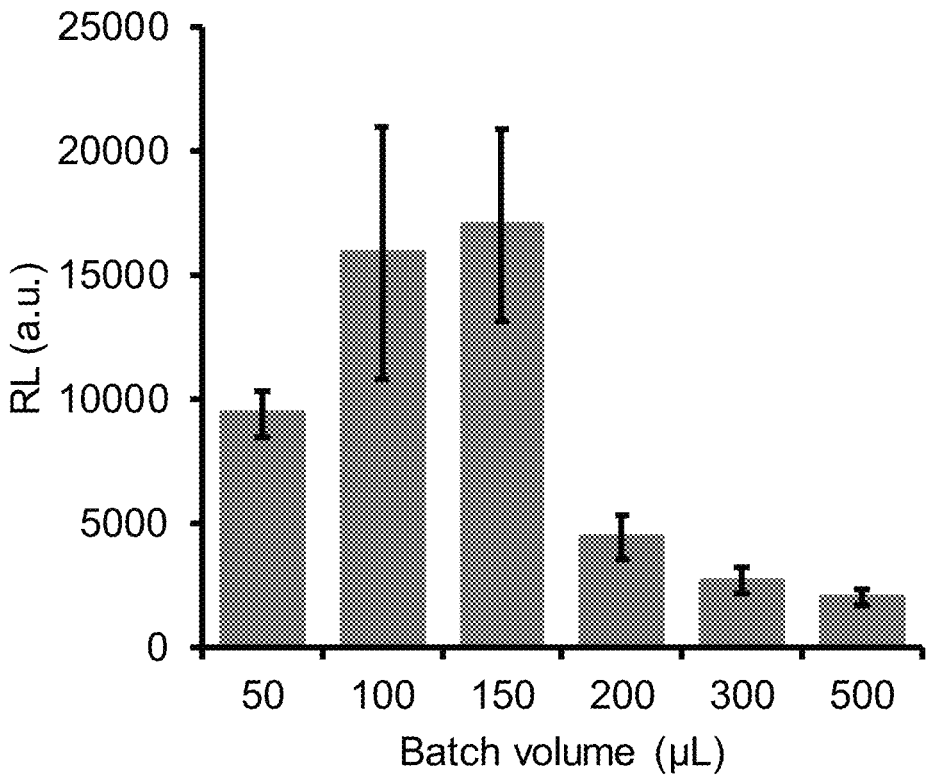

FIG. 23 shows the influence of batch volume variation in the cell-free translation mixture reflecting yield. The volume of the translation mixture was increased by adding deionized water to overcome the spatial hindrance and enhance protein production by providing enough search space for the prod-ucts to move. The yield increased until 150 µL, enabling the diffusion of expressed proteins outside the hydrogel, and the hydrogel scaffold provided confined space suitable for better turnover rates during the translation process. Upon further increasing the volume with DIW, the yield declined because the lysate was insufficient or diluted.

DETAILED DESCRIPTION

Overview

This application provides methods and compositions related to constructing nucleic acid hydrogels (e.g., RNA hydrogels) from nucleic acid concatemers having repetitive monomer units. Each monomer unit includes one or more G-quadruplex sequences. These G-quadruplex sequences cross-link the nucleic acid concatemer, such that the con-catemer self-assembles (i.e., without the need for any exter-nal crosslinkers) into a hydrogel. The nuclei acid concatemer can be produced by rolling circle amplification or rolling circle transcription of a circular DNA template. In some
embodiments, each monomeric unit of the nucleic acid
concatemer comprises a coding sequence for a polypeptide
of interest. The nucleic acid hydrogel formed by the nucleic
acid concatemer can be used for expressing the polypeptide
in high quantities. In some embodiments, at least two RNA
concatemers comprising G-quadruplex sequences are pro-
duced, one further comprising a spacer and the other further
comprising a sequence encoding a polypeptide of interest.
These two RNA concatemers are combined and self
assembled to form a single RNA hydrogel, referred to as a
wideband RNA hydrogel in this disclosure.

The nucleic acid hydrogels (e.g., RNA hydrogels) can be
molded in different dimensions and shapes, and these
nucleic acid hydrogels exhibit good, soft mechanical prop-
erties and excellent physicochemical stability. The nucleic
acid hydrogels disclosed herein can serve as a platform for
a wide range of biological applications (e.g., catalysis,
protein expression). The RNA hydrogel protein production
system closely resembles an intracellular environment, in
which RNAs are produced from a bundle of DNA and
proteins expressed abruptly within a limited space in cyto-
plasm surrounded by cytoskeletons (42). The gel matrix in
the hydrogel mimics the role of a cytoskeleton that provides
mechanical support to the cell. The nucleic acid hydrogel
has sufficient aqueous space, which is beneficial for enzy-
matic reactions (e.g., during protein expression). The nucleic
acid hydrogels have the useful features of porosity and close
vicinity of the protein-encoding sequences, which allow the
free-access of ribosomes to the RNA template in the nucleic
acid hydrogels. These features allow the nucleic acid hydro-
gels disclosed herein to serve as ideal cell-free protein
production platforms.

Producing proteins using the nucleic acid hydrogels dis-
closed herein is a straightforward and streamlined procedure
that is easy to follow. The nucleic acid hydrogel protein
production system can also be configured to produce pro-
teins in a continuous mode in a longer reaction period to
improve protein production efficiency and versatility further.
With multifarious engineered functionalities, the nucleic
acid hydrogels could expand the scope of state-of-the-art
applications in several fields, such as multiplex real-time
pathogen detection; bio-fuel cells for non-toxic, non-flam-
mable, eco-friendly energy sources; and bio-implants and
antibody-drug conjugates.

Terminology

As used in herein, the singular forms "a", "an" and "the"
include plural referents unless the content clearly dictates
otherwise. Thus, for example, reference to "an antibody"
optionally includes a combination of two or more such
molecules, and the like.

The term "about" as used herein refers to the usual error
range for the respective value readily known to the skilled
person in this technical field, for example ±20%, ±10%, or
±5%, are within the intended meaning of the recited value.

As used herein, the term "comprising" or "comprise" is
open-ended. When used in connection with a subject nucleic
acid (or amino acid sequence), it refers to a nucleic acid
sequence (or an amino acid sequence) that includes the
subject sequence as a part or as its entire sequence.

The terms "nucleic acid" and "polynucleotide" are used
interchangeably and as used herein refer to both sense and
anti-sense strands of RNA, cDNA, genomic DNA, and
synthetic forms and mixed polymers of the above. In par-
ticular embodiments, a nucleotide refers to a ribonucleotide, deoxynucleotide or a modified form of either type of nucleo-
tide, and combinations thereof. The terms also include, but
is not limited to, single- and double-stranded forms of DNA.
In addition, a polynucleotide disclosed herein, e.g., a circu-
lar DNA template, a nucleic acid concatemer disclosed
herein, may include either or both naturally occurring and
modified nucleotides linked together by naturally occurring
and/or non-naturally occurring nucleotide linkages. The
nucleic acid molecules may be modified chemically or
biochemically or may contain non-natural or derivatized
nucleotide bases, as will be readily appreciated by those of
skill in the art. Such modifications include, for example,
labels, methylation, substitution of one or more of the
naturally occurring nucleotides with an analogue, inter-
nucleotide modifications such as uncharged linkages (e.g.,
methyl phosphonates, phosphotriesters, phosphoramidates,
carbamates, and the like), charged linkages (e.g., phospho-
rothioates, phosphorodithioates, and the like), pendent moi-
eties (e.g., polypeptides), intercalators (e.g., acridine, pso-
ralen, and the like), chelators, alkylators, and modified
linkages (e.g., alpha anomeric nucleic acids, and the like).
The above term is also intended to include any topological
conformation, including single-stranded, double-stranded,
partially duplexed, triplex, hairpinned, circular and pad-
locked conformations. A reference to a nucleic acid
sequence encompasses its complement unless otherwise
specified. Thus, a reference to a nucleic acid molecule
having a particular sequence should be understood to
encompass its complementary strand, with its complemen-
tary sequence. The term also includes codon-optimized
nucleic acids that encode the same polypeptide sequence.

As used herein, the term "concatemer," refers to a nucleic
acid molecule comprising tandem repeats of a nucleic acid
sequence. Nucleic acid concatemer can be produced by
nucleic acid synthesis, or by, for example, a rolling circle
amplification or rolling circle transcription of a circular
DNA template.

As used herein, the term "cell-free synthesis," refers to the
in vitro synthesis of nucleic acids, polypeptides, small
molecules and/or viral particles in a reaction mix comprising
biological extracts and/or defined reagents. The reaction mix
will comprise a template for production of the macromol-
ecule, e.g., DNA, mRNA, and the like; monomers for the
macromolecule to be synthesized, e.g., amino acids, nucleo-
tides, and the like; and co-factors, enzymes and other
reagents that are necessary for the synthesis, e.g., ribosomes,
uncharged tRNAs, tRNAs charged with natural and/or
unnatural amino acids, polymerases, transcriptional factors,
tRNA synthetases, and the like The term "lysate" is any cell derived preparation com-
prising the components required for protein synthesis
machinery, wherein such cellular components are capable of
expressing a nucleic acid encoding a desired protein where
a majority of the biological components are present in
concentrations resulting from the lysis of the cells rather
than having been reconstituted. A lysate may be further
altered such that the lysate is supplemented with additional
cellular components, e.g., amino acids, nucleic acids,
enzymes, and the like. The lysate may also be altered such
that additional cellular components are removed or degraded
following lysis.

As used herein the term "RGx," refers to a non-G qua-
druplex structure formed by an RNA concatemer.

As used herein, the term "RGx concatemer," used inter-
changeably with "sGx," refers to the RNA concatemer that
forms the RGx. In one embodiment, the RGx concatemer
comprises multiple copies of SEQ ID NO: 13.

As used herein, the term "RGx solution," refers to the viscous solution formed by the RGx.

As used herein the term "RG4," refers to an RNA G-quadruplex formed by an RNA concatemer. In some embodiments, the RNA concatemer is produced by rolling circle transcription.

As used herein the term "RG4 concatemer," used interchangeably with "sG4," refers to the RNA concatemer that forms the RG4.

As used herein, the term "RG4 hydrogel," used interchangeably with "RG4 gel," refers to the hydrogel resulted from gelation of the RG4.

As used herein, the term "H-RG4 hydrogel" or "H-RG4 gel" refers to a hydrogel formed by an RNA concatemer produced from rolling circle transcription of a DNA template comprising the sequence of SEQ ID NO: 14.

As used herein, the term "W-RG4 hydrogel," or "wideband RG4 hydrogel," refers to a hydrogel formed by two different RNA molecules, at least one of which is an RG4 concatemer. In one embodiment, both RNA molecules are RG4 concatemers, one comprising poly adenines and the other encoding a polypeptide of interest. In one embodiment, one of the two RNA molecules is an RG4 concatemer comprising poly adenines and the other is an RNA molecule that encodes a polypeptide of interest.

As used herein, the term "nT RG4," refers to an RNA concatemer produced from rolling circle transcription of a DNA template comprising n thymines. For example, the term "30T RG4," "60T RG4," "90T RG4," "120T RG4," or "150T RG4," refers to an RNA concatemer produced from rolling circle transcription of a DNA template comprising 30 (SEQ ID NO: 33), 60 (SEQ ID NO: 34), 90 (SEQ ID NO: 35), 120 (SEQ ID NO: 36), or 150 thymines (SEQ ID NO: 37). N can be any integer. In some embodiments, n is in a range from 3 to 400, for example, from 10 to 300, from 20 to 200, from 25 to 180, or from 30 to 150. A DNA template that is transcribed to produce an nT RG4 is referred to as a spacer template for the nT RG4. In one example, a spacer template for 30T RG4 comprises the sequence of SEQ ID NO: 6.

Throughout the disclosure, the term "gel" and the term "hydrogel" are used interchangeably.

As used herein, the term "coding sequence," "protein encoding sequence," "protein coding sequence," refers to a DNA sequence, which can be transcribed to form a RNA transcript, and said RNA transcript can be translated to produce a polypeptide of interest. Depending on the context, a coding sequence for a protein of interest or a coding sequence encoding a protein of interest, referred to herein, may be the sequence of the sense strand that encodes a protein of interest (e.g., SEQ ID NO: 26), or the sequence of the anti-sense strand (e.g., SEQ ID NO: 21). A coding sequence used herein is also referred to as a target sequence.

As used herein, the term "non-coding sequence," refers to a genomic sequence that can be transcribed but cannot be translated.

As used herein, the term "molar fraction," refers to the percentage of the molar number of a reagent in a mixture. For example, a molar fraction of 75% of the spacer template in a mixture containing both the spacer template and coding template molecules refers to that the percentage of the molar number of spacer template molecules is 75% and the percentage of the molar number of the coding template molecules is 25%.

G Quaduplex Motif

A G-quadruplex motif disclosed herein comprises at least two, at least three, or at least four consecutive guanines (Gs).

In some cases, at least 20%, at least 30%, at least 40%, or at least 50% of the nucleotides in the G quadruplex motif are guanines. Nonlimiting examples of G-quadruplex motifs are disclosed in Phan, FEBS J. 277, 1107-1117 (2010) and Platella et al., Biochimica et Biophysica Acta 1861 (2017) 1429-1447, the entire disclosures of which are herein incorporated by reference. In some embodiments, the G-quadruplex motif comprises a sequence of $G3+N_{1-7}G3+Ni-7G3+N_{1-7}G_{3+}$ (SEQ ID NO: 46) where "G" represents Guanine, "N" represents any other nucleotide, and the number next to "G" or "N" (in subscript) represents the consecutive count of each nucleotide. In some embodiments, the G-quadruplex motif comprises a sequence selected from the group consisting of SEQ ID NOs: 47-49. Other exemplary G-quadruplex motifs include those comprising a sequence selected from the group consisting of SEQ ID NOs: 50-61.

In some embodiments, the G-quadruplex motif is an RNA sequence (RNA G-quadruplex motif). Nonlimiting examples of RNA G-quadruplex motifs include UAGG-GUUAGGGU (SEQ ID NO: 2) and GGGUUAGGGU (SEQ ID NO: 22). In some embodiments, the G-quadruplex motif is a DNA sequence (DNA G-quadruplex motif). Nonlimiting examples of DNA G-quadruplex motifs include TAGGGT-TAGGGT (SEQ ID NO: 20).

Also encompassed in this disclosure are RNA G-quadruplex motifs that can be derived from corresponding DNA G-quadruplex motifs disclosed herein or incorporated by reference. For example, an RNA G-quadruplex motifs can be derived from a DNA G-quadruplex motif by, e.g., replacing deoxyribonucleotides in the DNA G-quadruplex motif with respective corresponding ribonucleotides and replacing the nitrogenous base thymines with uracils. By way of an example, UAGGGUUAGGGU (SEQ ID NO: 2) can be derived from TAGGGTTAGGGT (SEQ ID NO: 20) using the above approach. Conversely, DNA G-quadruplex motifs can also be derived from any of the RNA G-quadruplex motifs disclosed herein or incorporated by reference by, e.g., replacing the ribonucleotides with respective corresponding deoxyribonucleotides and replacing the nitrogenous base uracil with thymine. These DNA G-quadruplex motifs are also encompassed in this disclosure.

Production of RNA Concatemers with G-quadruplex Motifs

In some embodiments, methods and compositions in this disclosure can be used to produce RNA concatemers by rolling circle transcription.

Circular DNA Template

A circular DNA template used in the rolling circle transcription may be produced from a single-stranded linear DNA and said linear DNA comprising the sequence that is complementary to the desired RNA sequence. The single-stranded linear DNA may be prepared by any method known to those of skill in the art, including chemical synthesis isolation from a nucleic acid library, or by recombinant technology.

Figures 1A, 1B, 1C, 1D, 1E, 1F, 1G:
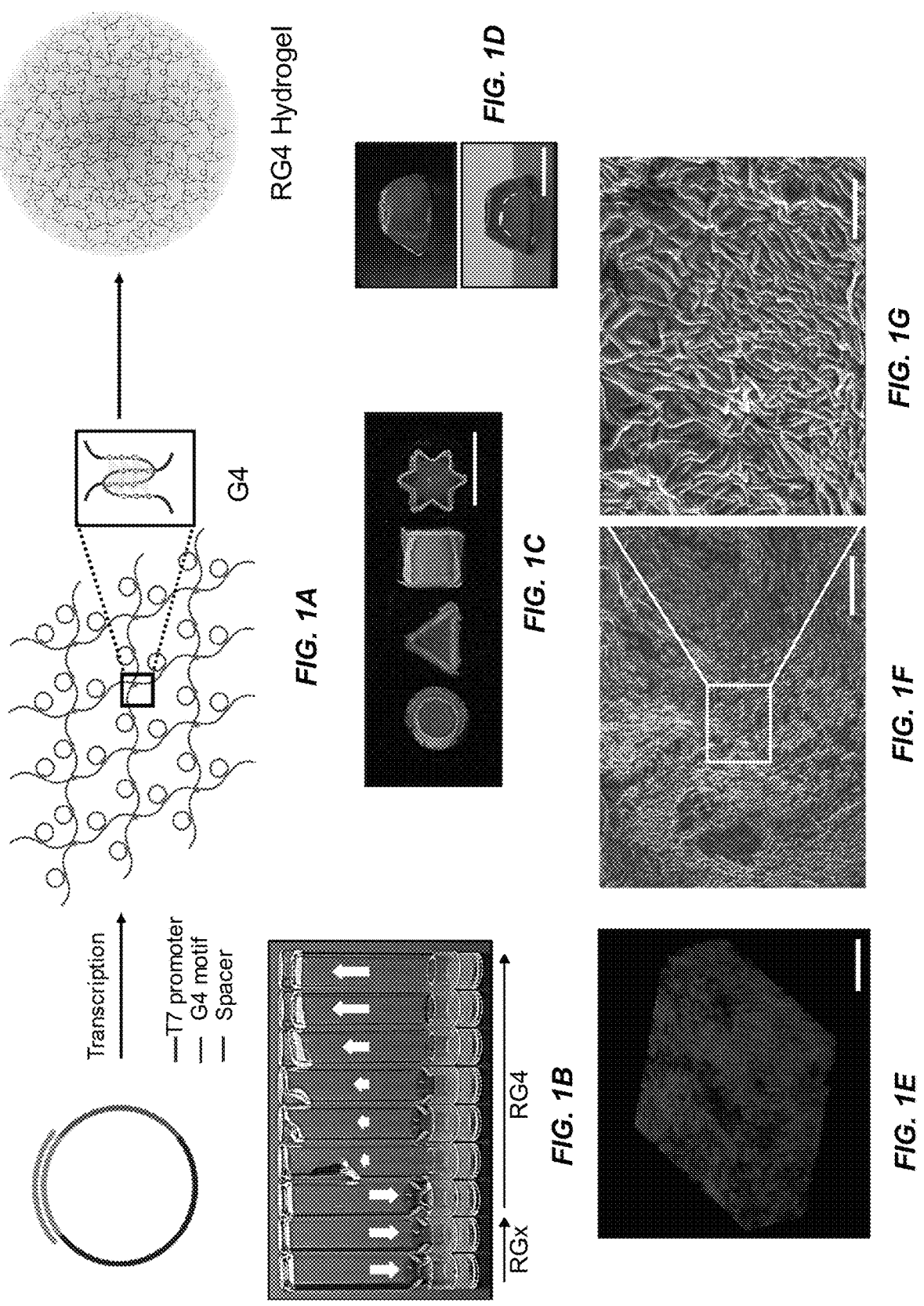
FIG. 1A-1G show the self-assembled rolling circle transcription ("RCT") products form RNA G-quadruplex (RG4) gel with inherent functionality.

The single-stranded linear DNA can be circularized to form a circular DNA template by a DNA ligase with the help of a splint oligonucleotide. The splint oligonucleotide comprises a first sequence that is complementary to one end of the DNA and a second sequence that is complementary to the other end of the linear DNA molecule. The splint oligonucleotide brings the two ends of the single-stranded linear DNA into proximity by hybridizing to the sequences at the two ends. A DNA ligase is then used to join the two ends of the DNA molecule to form a circular single-stranded DNA template. The splint oligonucleotide can then serve as the primer to initiate the rolling circle amplification to form a DNA concatemer, or to initiate the rolling circle transcription to form an RNA concatemer. One illustrative embodiment is shown in FIG. 1A, in which the splint oligonucleotide has a sequence complementary to the T7 promoter sequence in the circular template. By way of a non-limiting example, a single-stranded DNA molecule have the sequence of SEQ ID NO: 6, was annealed to the splint oligonucleotide having the sequence of SEQ ID NO: 12, the two ends of the DNA molecule will come together and hybridize to the splint oligonucleotide. In the presence of a DNA ligase, the two ends will join to form a circular DNA template.

The circular single-stranded DNA template comprises at least one promoter sequence that is operably linked to a spacer or a coding sequence of interest. In some embodiments, the splint oligonucleotide is complementary to the promoter sequence in the circular DNA template. In one embodiment, the split oligonucleotide has a sequence of SEQ ID NO: 12. The promoter sequence used herein can derive from a wide range of promoters. The promoter may be a mutant promoter, a truncated promoter, or a hybrid promoter. The promoter may be a constitutive or an inducible promoter. Nonlimiting examples of suitable promoters include a T7 promoter, a T3 promoter, a Lac promoter, an araBad promoter, a Trp promoter, a Tac promoter, or an SP6 promoter.

The circular single-stranded DNA template may further one or more other regulatory sequences, including without limitation, repressors, activators, transcription and translation enhancers, DNA-binding proteins, and the like The circular DNA template such may also comprise one or more functional sequences for example, a coding sequence of a polypeptide of interest or a spacer sequence, as further described below.

Spacer

A spacer is located between the promoter sequence and the G4 quadruplex motif in the circular DNA template. Typically the spacer is a non-coding sequence. The spacer may comprise multiple thymines. In some embodiments, the spacer comprises 15-220, e.g., 20-200, 25-150, or 30-120 nucleotides. In some embodiments, at least 50%, at least 60%, at least 90%, at least 95% of the nucleotides in the spacer are thymines (T). In some embodiments, the spacer comprises at least 10 (SEQ ID NO: 39), at least 12 (SEQ ID NO: 40), at least 13 (SEQ ID NO: 41), at least 14 (SEQ ID NO: 42), at least 15 (SEQ ID NO: 43), at least 16 (SEQ ID NO: 44), at least 20 consecutive thymines (SEQ ID NO: 45). In some embodiments all the nucleotides in the spacer are thymines. In some embodiments, the spacer comprises 3T, 10T (SEQ ID NO: 38), 30T (SEQ ID NO: 33), 60T (SEQ ID NO: 34), 90T (SEQ ID NO: 35), 120T (SEQ ID NO: 36), or 150T (SEQ ID NO: 37). In some embodiments, the spacer consists of 3T, 10T (SEQ ID NO: 38), 30T (SEQ ID NO: 33), 60T (SEQ ID NO: 34), 90T (SEQ ID NO: 35), 120T (SEQ ID NO: 36), or 150T (SEQ ID NO: 37). In some embodiments, the circular DNA template comprises a spacer, and said spacer comprises a sequence selected from the group consisting of SEQ ID NOs: 6-9, and 11.

Coding Sequence

The coding sequence encodes a polypeptide of interest. In some embodiments, the length of the coding sequence may be in a range from 20 to 300 nucleotides, e.g., from 25 to 200 nucleotides, or from 30 to 166 nucleotides. In terms of the lower limits, the coding sequence has a length of at least 20 nucleotides, at least 30 nucleotides, at least 50 nucleotides, or at least 100 nucleotides. In terms of the upper limits, the coding sequence has a length of no longer than 300, no longer than 200, or no longer than 166 nucleotides.

Nonlimiting examples of polypeptides of interest include an antibody, such as a single domain antibody, a single chain antibody, a fragment of an antibody (e.g., an scFv or a Fab fragment), a growth hormone (e.g., insulin), a receptor for hormones or growth factors; a CD protein such as CD-3, CD4, CD8, and CD-19; an interleukin; an interferon; a T-cell receptor; an enzyme; a viral antigen; a transport protein; a homing receptors; an addressin; a regulatory proteins (e.g., a TAT protein); and a fragment of any of the above-listed polypeptides. In some embodiments, the polypeptide of interest is a single-domain antibody, comprising a single monomeric variable antibody domain, e.g., a single VHH domain. In some embodiments, the single-domain antibody is anti CD40 ligand ("anti CD40L") single-domain antibody. In some embodiments, the single-domain antibody is Letolizumab.

In some embodiments, the coding sequence encodes an amino acid sequence that is selected from the group consisting of SEQ ID NO: 23, 24, 25 and 27.

In some embodiments, the coding sequence is located between the promoter sequence and the G4 quadruplex motif in the circular DNA template. In some embodiments, the coding sequence is in an expression construct. In some embodiments, the coding sequence has a sequence that is selected from the group consisting of SEQ ID NO: 14, 16, 18, and 26, A polypeptide of interest produced by the invention can be used for one or more of the following purposes or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component (s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, the ability to bind antigens or complement); and the ability to act as an antigen in vaccine composition to raise an immune response against such protein or another material or entity which is cross-reactive with such protein.

The polypeptides produced by the invention can be used for any purpose known to one of skill in the art. Preferred uses include medical uses, including diagnostic uses, prophylactic and therapeutic uses. For example, the proteins can be prepared for topical or other type of administration. Another preferred medical use is for the preparation of vaccines. Accordingly, the proteins produced by the invention are solubilized or suspended in pharmacologically acceptable solutions to form pharmaceutical compositions for administration to a subject. Appropriate buffers for medical purposes and methods of administration of the pharmaceutical compositions are further set forth below. It will be understood by a person of skill in the art that medical compositions can also be administered to subjects other than humans, such as for veterinary purposes.

RNA Polymerase

An RNA polymerase in this disclosure can be any RNA polymerase that can recognize the promoter in the DNA template as described above. Non-limiting examples of RNA polymerases include a T7 RNA polymerase, an SP6 RNA polymerase, or a T3 RNA RNA polymerase.

Transcription

The rolling circle transcription can be performed in a reaction mixture comprising one or more of the following components: the circular DNA template as described above, an RNA polymerase that recognize the promoter to which gene of interest is operatively linked (e.g., T7 polymerase), and optionally one or more transcription factors directed to optional regulatory sequence to which the template is operatively linked, ribonucleotide triphosphates (rNTPs), a buffer, and optionally other transcription factors and cofactors.

The rolling circle transcription may be performed at a suitable temperature, for example, 25° C.-40° C., or about 37° C. The transcription reaction may last for a period of time that lasts from one hour to overnight.

Optionally, at the end of the rolling circle transcription, RNA transcripts are purified from the reaction mixture using methods well known in the art. In one embodiment, the RNAs may be purified from the transcription mixture using a tubular PAGE column, for example Prepcell 491, available from Bio-Rad (Hercules, CA).

Production of DNA Concatemers with G-quadruplex Motifs

In some embodiments, DNA concatemers having G-quadruplex motifs can be produced by rolling circle amplification using a circular DNA template as disclosed above. These DNA concatemers can form DNA hydrogels.

A rolling circle amplification can be performed using a DNA polymerase that has strand displacement activity, i.e., being able to displace downstream DNA encountered during synthesis. A DNA polymerase having strand displacement activity is able to generate a DNA concatemer having multiple copies of a sequence that is complementary to the circular DNA template. Suitable DNA polymerases that can be used to perform rolling circle amplification include but are not limited to, a Phi29 polymerase, a Bst DNA Polymerase, Large Fragment, and a Deep-VentR DNA polymerase, all available from New England BioLabs (Ipswich, MA).

G-quadruplex

The nucleic acid concatemers produced as described above can form G-quadruplexes. FIG. 1A shows a schematic framework in which the G-quadruplex motifs in the nucleic acid concatemers are assembled to form an RNA G-quadruplex (shown as "G4" in FIG. 1A). An RNA G-quadruplex comprising a HiBiT-encoding sequence is referred to as H-RG4. As illustrated in FIG. 1A, a G-quadruplex typically include a four-stranded helical nucleic acid structure comprising multiple stacked G-tetrads, each of which consists of four guanine bases that associate in a cyclical manner through Hoogsteen hydrogen bonds. These G-tetrads may be further stabilized through coordination to a cation (e.g., a $K^+$ or $Na^+$) in the center. The body of stacked G-tetrads, comprising a total of 2 or more layers, is collectively referred to as the G-tetrad core. Each of the four guanine columns constituting the G-tetrad core can arise from a single (continuous column) or two (discontinuous column) separate guanine stretches. Properties of G-quadruplexes are discussed in Phan, FEBS J. 277, 1107-1117 (2010), the entire disclosure is herein incorporated by reference.

Figures 2A, 2B, 2C:
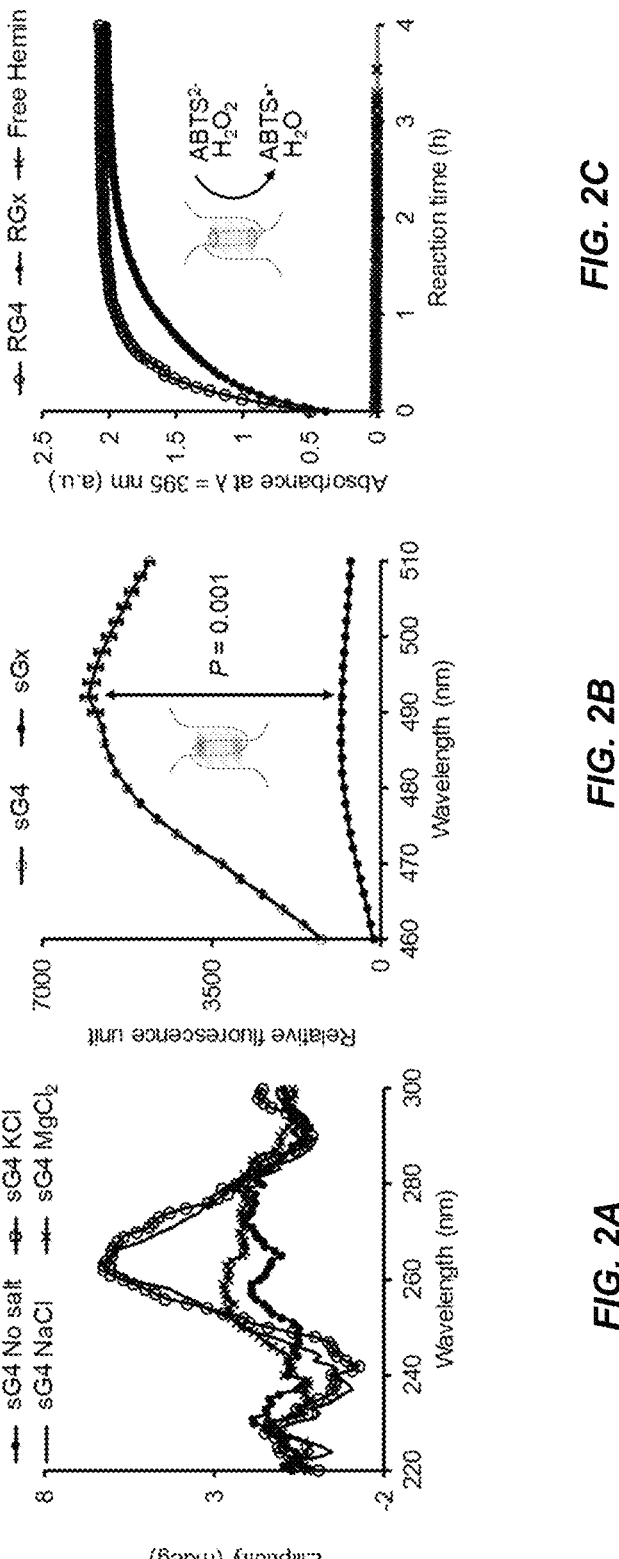
FIG. 2A-2C show spectroscopic validation and identification of RG4.

G quadruplexes can be detected by binding assays that are well known. In some embodiments, they can be detected by assays involving a fluorescent turn-on ligand, thioflavin T (ThT). Umar et al. (2019) and Mohanty et al., 2013. A binding of G quadruplex to ThT would significant enhance the fluorescence intensity, a detection of significant enhancement in fluorescence intensity would indicate the presence of G quadruplex. The RNA transcripts produced by the rolling circle transcription are able to produce G quadruplexes. One illustrative example is shown in FIG. 2B, where a significant enhancement in fluorescence intensity was observed at 488 nm using the ThT detection method, indicating the presence of the G-quadruplexes.

In some embodiments, a G quadruplex can also be visualized by detecting signal associated with self-biotinylation when it is complexed with hemin, as disclosed in Li et al. (2019). In one illustrative embodiment, G-quadruplexes is mixed with hemin in the presence of $H_2O_2$ and biotin tyramide. A proper formed G-quadruplexes would self-biotinylates and the biotin groups added to the G-quadruplexes will be able to bind the streptavidin and produce a bright signal. As shown in FIG. 13, the RG4 concatemer, comprising copies of the short G quadruplex RNA UAGG-GUUAGGGU (SEQ ID NO: 2) produced bright spots which demonstrates that it was capable of forming RG4 quadruplex. In contrast, the RGx concatemer, comprising copies of short scrambled RNA: UACUGUUACUGU (SEQ ID NO: 13), was not able to form quadruplexes, as indicated by the lack of such spots.

Wideband Hydrogel

In some embodiments, two nucleic acid concatemers are combined to form a single hydrogel, which is referred to as a wideband hydrogel. Each of the two nucleic acid concatemers can be produced by rolling circle transcription or rolling circle amplification from a circular DNA template, and each comprises a promoter and a G4 quadruplex motif. One of the two circular DNA templates further comprises a spacer, and the other further comprises a coding sequence for a polypeptide of interest. Any of the spacer and coding sequences described above can be used in the circular DNA templates disclosed herein to produce a wideband hydrogel.

In some embodiments, both nucleic acid concatemers are DNA concatemers. In some embodiments, both nucleic acid concatemers are RNA concatemers. The wideband hydrogel formed by the two RNA concatemers are referred to as W-RG4. FIG. 18A illustrates the formation of an exemplary wideband hydrogel from the rolling circle transcription of two circular DNA templates.

The promoters used in the two circular DNA templates can be the same or be different. Similarly, the G quadruplex motifs in the two circular DNA templates may or may not be the same. Any of the promoters and G quadruple motifs disclosed in this application can be used to form a wideband hydrogel disclosed in this application.

Ratios of the Two Templates

The inventors have discovered surprisingly using the two DNA circular templates at appropriate proportions can improve translation efficiency. The first circular DNA comprises (i) a first promoter sequence, (ii) a sequence complementary to a first G-quadruplex motif, and (iii) a spacer comprising poly thymines. The second circular DNA template comprises (i) a second promoter sequence, (ii) a sequence complementary to a second G-quadruplex motif, and (iii) a coding sequence of the polypeptide of interest. The circle DNA template comprising the spacer is also referred to as "the spacer template," and the circular DNA template comprising the coding sequence is also referred to as "the coding template." In some embodiments, the molar fraction of the spacer template in the mixture of both the spacer and the coding templates ranges from 25% to 75%. As shown in FIG. 18B-18D, a mixture comprising the spacer template at a molar fraction ranging from 25% to 75% all produced a sufficient high amount of a polypeptide of interest (the HiBiT polypeptide in FIG. 18). A molar fraction of 75% of the spacer template exhibited the highest yield.

In some embodiments, the spacer template comprising a sequence selected from the group consisting of SEQ ID NO: 6-9, and the coding template comprise a sequence selected from the group consisting of SEQ ID NOs: 14, 16, and 18.

In some embodiments, the ratio of the length of the coding sequence to the length of the spacer sequence is in a range from 1:0.2 to 1:2, or about 1:1.

Plasmid Wideband Hydrogel

In some embodiments, the wideband hydrogel is formed by gelation of 1) an RNA concatamer produced from RCT of a circular template comprising a spacer ("a spacer template") and a G quadruplex motif and 2) an mRNA transcribed from an expression construct comprising a coding sequence for a polypeptide of interest, as described above. In some embodiments, the peptide of interest encoded by the coding sequence in the expression construct consists of at least 20 amino acid residues, at least 30 amino acid residues, at least 40 amino acid residues, at least 60 amino acid residues. In one embodiment, the coding sequence encodes a single domain antibody. In one embodiment, the coding sequence encodes an anti CD40L single-domain antibody (SEQ ID NO: 26). In some embodiments, the expression construct comprises a sequence of SEQ ID NO: 27. In one embodiment, the W-RG4 hydrogel is formed by gelation of 1) a RNA concatemer produced from RCT of a circular DNA template comprising SEQ ID NO: 7 and 2) an mRNA transcribed from a plasmid comprising SEQ ID NO: 26.

In some embodiments, the molar ratio of the expression construct and the spacer template may be in a range from 1:2 to 1:400, e.g., from 1:5 to 1:200, from 1:10 to 1:120, or from 1:12 to 1:102.

Non-limiting examples of expression constructs (e.g., vectors) that can be used include pK7, pIVEX, pET, pTXB, pUC, and pF3K. In some embodiments, the molar ratio of the spacer template to the vector used in the transcription mixture is within a range from 1:1 to 1000:1, e.g., from 10:1 to 200:1.

Gelation

The G-quadruplexes (e.g., RG4) formed by the nucleic acid concatemer (or the two nucleic acid concatemers as in the wideband system) can self-assemble into a hydrogel. The formation is facilitated by the non-covalent interactions between the guanines among the G-quadruplex motifs. The G-quadruplex hydrogels can be instantly prepared by the addition of various fluids, such as serum, artificial tear, or cell culture media, or phosphate buffered saline to the nucleic acid at ambient temperatures (e.g., 20° C.-40° C.). In some embodiments, gelation may takes 0-100 hours, e.g., from 3-60 hours, or from 3-48 hours. In some embodiments, the gelation may take, e.g., 3, 6, 9, 12, 24, or 48 hours.

Gelation can be detected by various methods. One of the common diagnostic tests of gelation is the vial inversion test. The vial inversion test is performed by placing a vial containing a sample upside down and observing whether the sample flows under its own weight. If a sample does not flow under its own weight, it is a gel.

As shown in FIG. 1A-1G, an exemplary RG4, comprising copies of the sequence of SEQ ID NO: 2, formed a hydrogel (an RG4 hydrogel). The formation of the hydrogel was instantly visible, and the hydrogel volume grew during a period of 0-48 hours. The gelation of RG4 formed a single chunk material that exhibits strong elasticity with opposing gravitational force when tested using the vial inversion test. In contrast, the RGx, comprising copies of the sequence of SEQ ID NO: 13, did not form a hydrogel; instead, it produced a viscous, non-gel solution that slid instantly to the bottom of the container.

Hydrogel Characterization

Structure

The hydrogels (RG4 or W-RG hydrogels) formed as disclosed above can be molded into different shapes when placed in various polygonal molds. For example, the hydrogels disclosed herein may be molded into circular, triangular, rectangular, and star shapes (FIG. 1C) and a 3-D cylindrical shape (FIG. 1D). The hydrogels disclosed herein all possess interconnected porous structure, which can be detected by an imaging analysis, e.g., a confocal imaging analysis. Illustrative imaging results are shown in FIG. 9 and FIG. 1E, which indicate the presence of a periodic interconnected porous structure in the RG4 hydrogel.

Viscoelastic and Mechanical Properties

The RG4 gels disclosed herein have excellent viscoelastic and mechanical properties, rendering them ideal platforms for a variety of biological applications. Various methods can be used to assess these properties. In some embodiments, the hydrogel's viscoelastic properties of can be tested using methods well known in the art, for example, rotational assays, oscillational assays, and vertical assays, as described in www.rheologytestingservices.com/, the entire content of which is herein incorporated by reference. In some embodiments, a temperature sweep rheology test is used to measure the viscosity change over increasing and decreasing temperature ramps. In some embodiments, the hydrogel's viscoelastic properties can be examined by using a rotational rheometer, e.g., ARES-G2 (TA Instruments, New Castle, DE).

In some embodiments, the hydrogel's the stiffness can be evaluated using a Young's modulus test. Young's modulus test defines the relationship between stress (force per unit area) and strain (proportional deformation) in a material in the linear elasticity regime of uniaxial deformation. In one embodiment, the Young's modulus was determined through a compression test on the centimeter scale obtained from the slope of the curve, as described in Hermann et al. (2001). The Young's modulus determined through a compression test on the centimeter scale of the RG4 gel disclosed herein is typically in the range of 12 kPa-100 kPa, e.g., 20 kPa-58 kPa, or about 38.4 kPa. As shown FIG. 3A, the modulus of the RG4 gel produced herein were in the range of 6-50 kPa, which were comparable to previously reported soft gels (23, 24, 25).

Figures 14A, 14B, 14C, 14D:
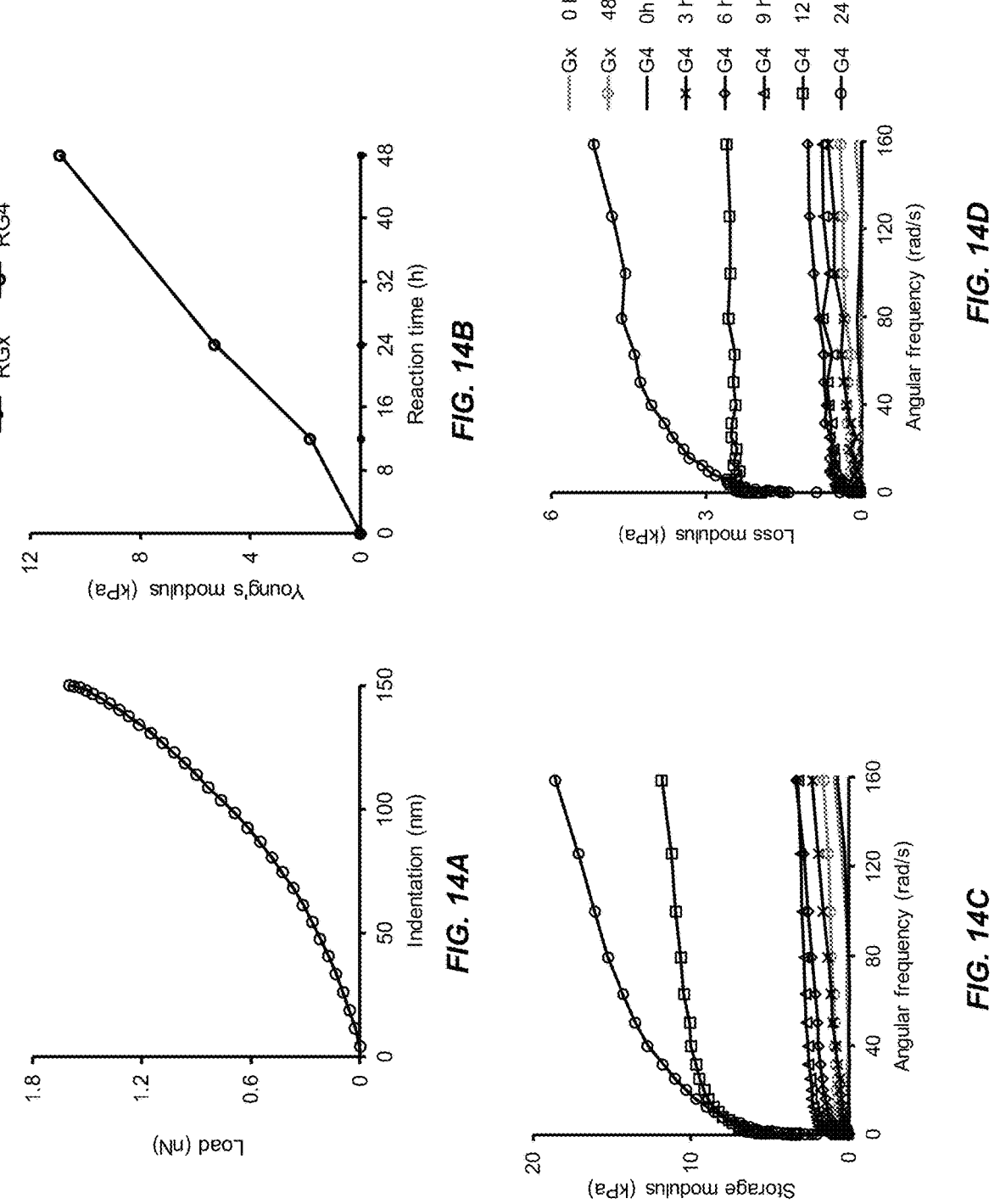
FIG. 14A-14D show the results of the modulus measurement of the RG4 gel and RGx products.

In one embodiment, an Atomic Force Microscopy (AFM)-based indentation test method on the nanometer scale is used. The AFM-based test is typically used to analyze the elastic modulus of soft and hydrated samples using force curves. Methods for using AFM-based indentation test is well known and as described in (26, 27). The RG4 gel disclosed herein exhibits an excellent time-dependent increase in modulus, and the time-dependent increase in modulus is surprisingly significantly higher than that is reported for DNA-based gels. In one embodiment, the time-dependent increase in modulua in the range of 5 to 20 kPa (e.g., about 10.93 kPa) at 48 hours. One illustrative example is shown in FIG. 14A and FIG. 14B.

In some embodiments, storage modulus of the hydrogel can be determined using dynamic mechanical analysis methods. See, Encyclopedia of Polymer Science and Technology, DOI: 10.1002/0471440264.pst102.pub2. In general, these approaches analyze viscoelastic properties of polymeric materials by taking forced oscillatory measurements. In one embodiment, storage modulus of the hydrogels can be measured using a Dynamic Frequency Scan. The RG4 gel disclosed herein has a dominant solid-like structure as indicated by a storage modulus that is higher than the loss modulus at 24 h (FIGS. 14C and 14D). In addition, the RG4 gel shows high storage modulus, more than ten fold higher than that of the RGx solution, see FIG. 3B.

Water retention and absorption capacity of the hydrogels can be analyzed using methods generally described in (31). In one embodiment, the water retention and absorption capacity is determined by measuring the volumetric dehydration and rehydration ratio of the gel, Specifically, the mass of the freshly prepared hydrogel required for the initial mass and the mass of dried hydrogel required for the rehydrated mass were measured to assess the water-retaining and absorbing nature of the RG4 hydrogel. Water retention and absorption capacity can be calculated using Equation 1 below.

$$Q = 1 + \rho_2 \cdot \left( \frac{m_{sw}}{m_d \cdot \rho_2} - \frac{1}{\rho_1} \right)$$

Equation (1)

Q: swelling degree, the volume ratio of swollen hydrogel with respect to the volume of dried gel (pure gel material without the media) expressing the volumetric increase of the hydrogel when swollen $\rho\_1$: density of swelling medium (DI water)

$\rho\_2$: density of polymer (gel components excluding the swelling medium)

m_sw: mass of swollen gel m_d: mass of dried gel

Figure 3A:
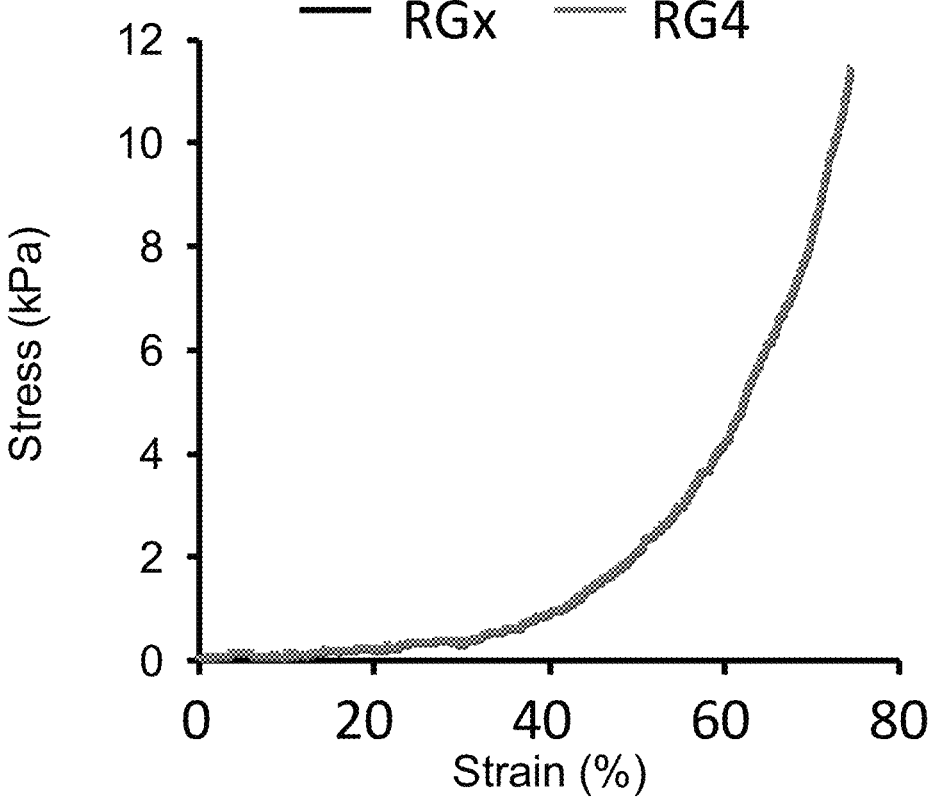
FIG. 3A-3F show the analysis of physical properties of the RG4 gel.
Figure 3B:
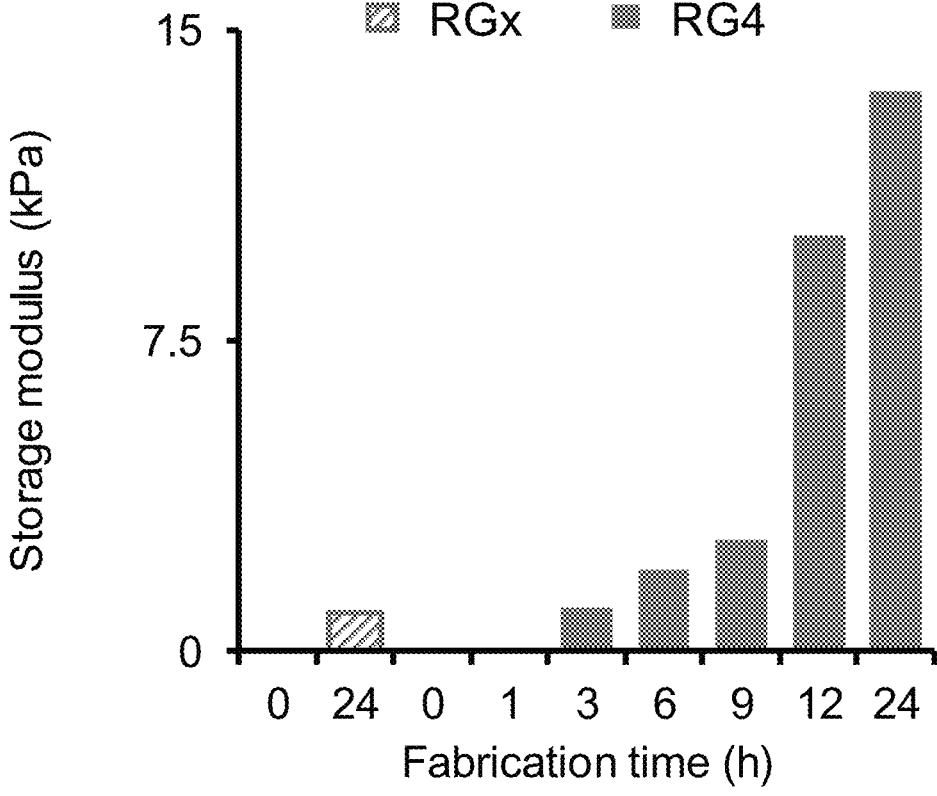
Figure 3C:
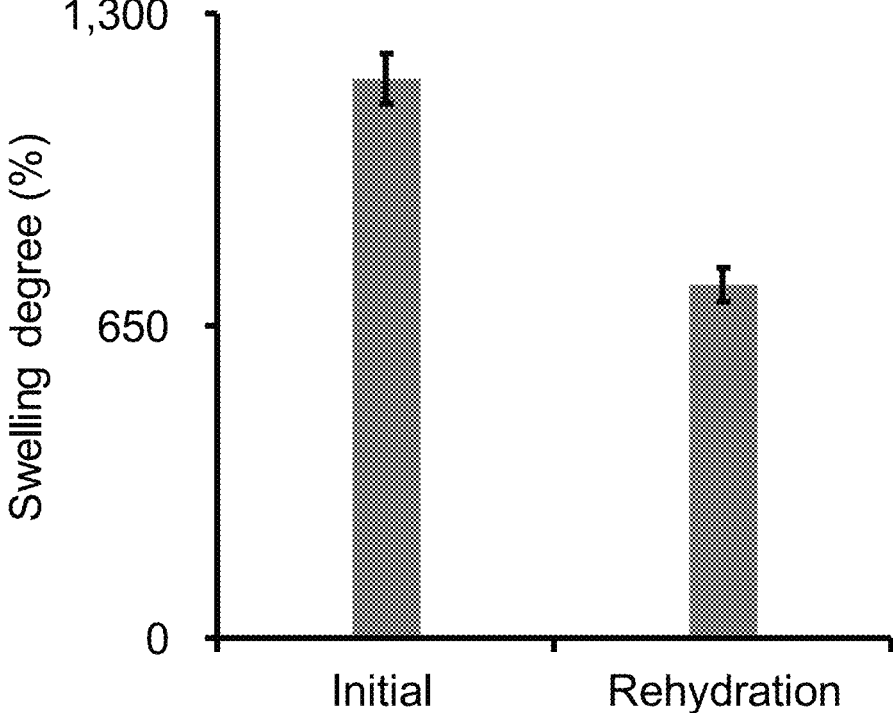

The RG4 gel disclosed in this application has excellent water retention and absorption capacity. The RG4 hydrogel as disclosed herein typically has a swelling degree of 500% to 5000%. One illustrative example is shown in FIG. 3C, where the swelling degree was 1164.1%.

Additionally, the RG4 hydrogel is capable of undergoing swelling-rehydration cycles, exhibiting a re-swelling degree of at least 400%, at least 500%. In one illustrative embodiment, the RG4 hydrogel showed a re-swelling degree (or a rehydration degree) of 734.2% (FIG. 3C, "Rehydration"). A re-swelling degree is the degree of swelling when a dehydrated gel is contacted with water or an aqueous solution and becomes rehydrated. In one embodiment, a re-swelling degree is represented by a volume ratio of the rehydrated hydrogel (after contacting with water or an aqueous solution) to the dehydrated hydrogel. Thus, the RG4 hydrogels are able to maintain a high water content environment in which translation can occur with high efficiency.

A RG4 gel disclosed herein has high diffusivity. It allows reaction components and products (e.g., ribosomes) to diffuse freely and also permits their ingress and egress through the pores of the hydrogel. These features allows the further enhancement in translation efficiency. The diffusivity of the hydrogel can be assessed by measuring the diffusion velocity of an agent (for example, ThT or a ribosome) across the hydrogel. The diffusion velocity can be determined by the distance traveled by the agent captured on confocal microscope and the time required for the diffusion. In one illustrative embodiment, a theoretical calculation of diffusion velocity of into G4-RNA hydrogel can be calculated using the Equations below (32).

$$\frac{D_e}{D_0} = \left[ 1 + \left( \frac{r_s^2}{k} \right)^{\frac{1}{2}} + \frac{1}{3} \frac{r_s^2}{k} \right]^{-1}$$

Equation (2)

$r_s$: Radius of the solute, 0.7 nm for Thioflavin T (47), 5 nm for a large subunit of the prokaryotic ribosome e (48). k: Hydraulic permeability of the medium.

Diffusivity at infinite dilution ($D_0$), porosity of the hydrogel not considered, is given as below by the Stokes-Einstein Law for diffusion in solution (49):

$$D_0 = \frac{K_b T}{6 \pi \eta r_S}$$

Equation (3)

Kb: Boltzmann coefficient, $1.38065 \times 10^{-23}$ JK$^{-1}$ $\eta$: Dynamic viscosity of the media solvent, 1.0016 mPa·s at 20° C., 0.696 mPa·s at 37° C. (50)

Hydraulic permeability of the medium is given as below (51):

$$k = 0.31 r_f^2 \varphi^{-1.17}$$

Equation (4)

Figure 15:
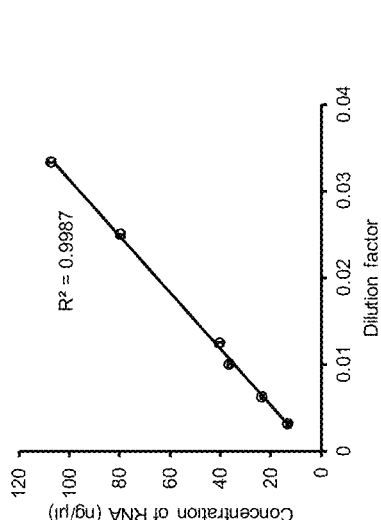
FIG. 15. shows the quantification and density calculation of the G-quadruplexes in the RG4 hydrogel. The concentration of total RNA was measured using an RNA-specific fluorescent dye provided in the Qubit™ RNA BR Assay Kit. The concentration of one unit of the RCT cycle was calculated based on the concentrations of total RNA and the G-quadruplexes. To calculate the diffusivity, the average distance between G-quadruplex structures was calculated based on the RNA quantity in the RG4 hydrogel. The estimated distance between the G-quadruplexes was 21.11 nm in the 3-dimensional distribution.

$r_f$: Radius of the pore of the hydrogel, 5.65 nm estimated by AFM image (FIG. 3E) and 13.1 nm estimate d by quantified RNA (FIG. 15).

$\varphi$: Volume fraction of polymer in the gel, estimated by the mass of dried hydrogel, 0.0852

Molar diffusion flux of the diffusing solute (J) given as below by the Fick's first law (52):

$$J = -D_e \frac{dC}{dx}$$

Equation (5)

C: Molar concentration of the solute, 10 µM for ThT, 2.4 µM for ribosome x: Travel distance of the diffusing solute, 573.4 µm for ThT, 10 µm for hydrogel pad Diffusion velocity of the solute transported into the porous hydrogel (v) is given as below (53):

$$v = \frac{J}{C}$$

Equation (6)

In one example the time required for a ribosome to completely diffuse into a 20-µm deep hydrogel (33) were in the range from 4.5 to 5.5 µm/s. In some cases, the ribosome diffuse 10 µm on one side of the hydrogel in about 1.8 seconds and 2.2 seconds. See FIG. 3D.

Figure 3D:
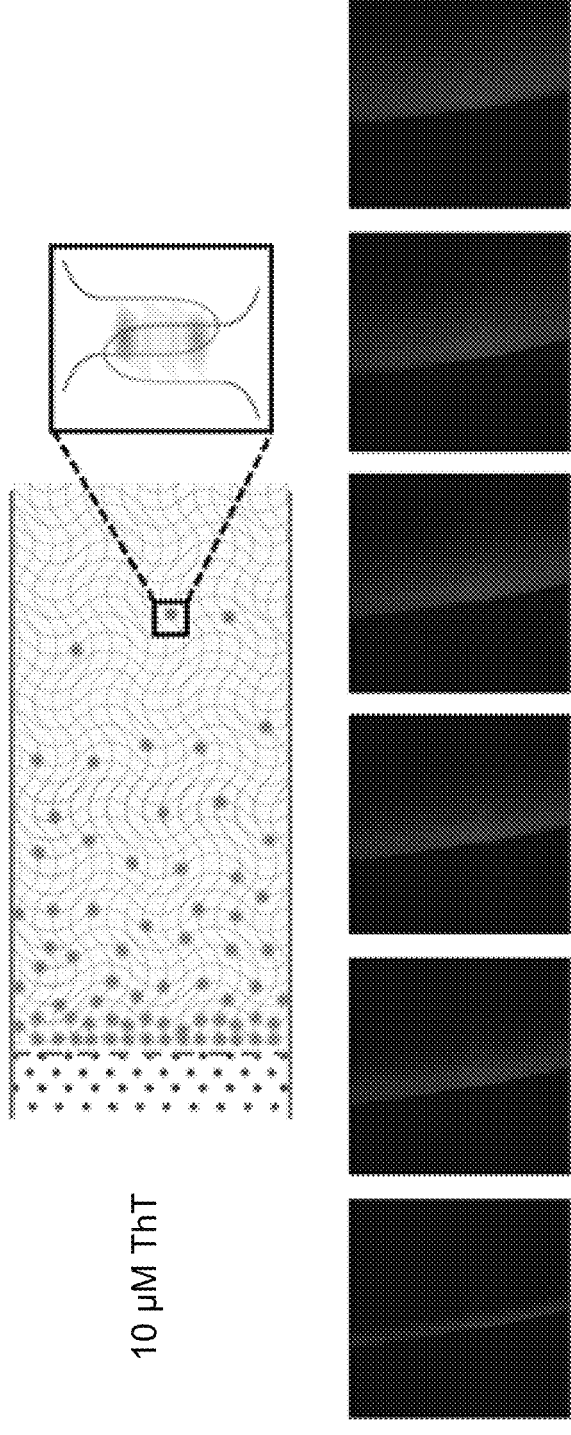
Figure 3E:
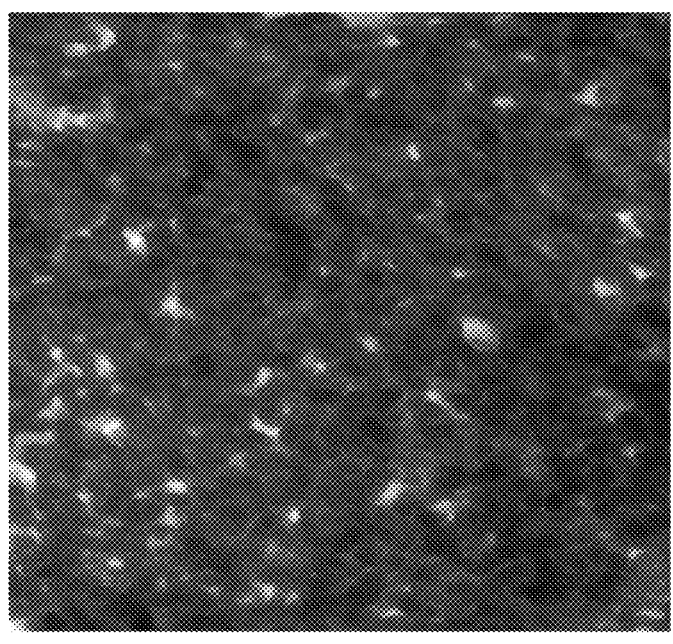
Figure 3F:
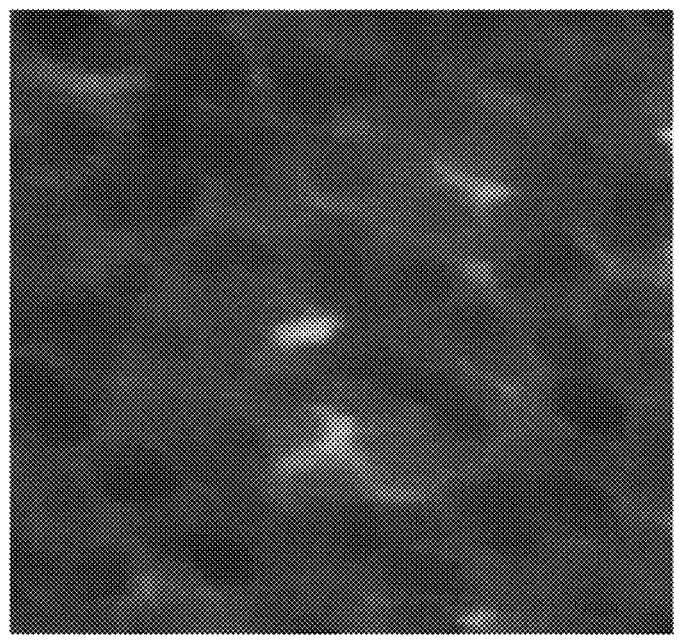

Various ways can be used to measure the pore size of a hydrogel. In one embodiment, the pore size is estimated to be the average distance calculated between the G4 structures in the RG4 hydrogel and/or based on the pore size estimation from the AFM image (FIG. 3E and FIG. 15). In some embodiments, the RG4 hydrogel has a pore size in a range of 1-30 nm, e.g., 2-25 nm, 3-10 nm, or about 5.65 nm, when using the average distance between the G4 structures in the hydrogel determined from atomic force microscopy (AFM) images as the pore size.

Function:

An RG4 hydrogel disclosed herein can not only serve as a scaffold for various applications but also enhance the activities of a bioactive agent (e.g., an enzyme) with which it forms a complex. In some embodiments, the RG4 can boost the activity of a peroxidase (e.g., a hemin) when it forms a complex with the enzyme. The enhancement can be detected using a colormetric reaction involving the substrate of the enzyme, e.g., a colorimetric change of 2,2'-azino-bis-3-ethylbenzothiazoline-6-sulfonic acid (ABTS). See FIG. 2C. The improved peroxidase activity (reflected by an increase in absorbance of $A_{395\ nm}$) was detected across a wide pH range (for example pH 4.9-pH 7.9). See FIG. 12. This indicated that the G4 crosslinking in the gel promotes the enzymatic activity, in addition to serving as a scaffold.

Thus in some embodiments, this disclosure provides an RG4 hydrogel disclosed above that is complexed with a bioactive agent, and optionally the RG4 enhances the activity of the bioactive agent. The enhancement may be at least 20%, at least 30%, at least 40%, at least 50%, or at least 60% relative to the activity of the bioactive agent that is not complexed with the RG4 hydrogel.

Suitable bioactive agents include but are not limited to a biological or chemical compound, such as a polypeptide, an enzyme (e.g., a peroxidase), an antibody, a growth factor, an antigen, liposome, small interfering RNA, or a polynucleotide, therapeutic agent (e.g., drugs, toxins, immune modulators, chelators, antibodies, antibody-drug conjugates, photoactive agents or dyes, and radioisotopes), or a chemoattractant. The bioactive agent may be naturally-occurring or artificially synthesized.

Stability

The RG4 hydrogels disclosed herein are stable, with a half-life of at least 30 hours, at least 35 hours, or at least 40 hours. The term "half-life," when used in connection with a nucleic acid hydrogel, refers to the time required for the nucleic acid content in the gel to reduce to 50% of its initial amount. The half-life of the RG4 hydrogel is significantly longer than the RGx solution (FIG. 4E). As shown in Example 6, FIG. 4A, an exemplary RG4 was able to maintain at least 53.4% of its initial RNA content during 48.9 hours; while the RGx only kept 21.6% of its initial RNA content after 38.3 hours. The RG4 gel degraded slower than the RGx under the same conditions, which is likely due to the fact that RG4 has a highly integrated nature.

Yield

Not only the RNA in the RG4 degrades slower, but the formation of G quadruplex in RG4 prolongs RNA synthesis time during the transcription stage. As shown in FIG. 4F, in contrast to RGx, the amount of RNA in the RG4 continued to increase after 4 hours from the initiation of transcription reaction. This elongated transcription time and the high stability of the RG4 gel enables producing a high amount of RNA during the RCT. In one illustrative example shown in FIG. 4F, the RNA yield from RG4 hydrogel was at least three fold higher than that of the RGx solution. This high RNA yield would contribute to the high protein production in the downstream translation process.

Cell-free Protein Production

A RG4 hydrogel produced as described herein can be used for cell-free protein synthesis. In some embodiments, the translation is uncoupled with the transcription so that the RG4 hydrogel forms before the initiation of translation. A cell-free protein synthesis translation mixture may include, but are not limited to, one or more cell extracts/lysates, ATP or energy source (e.g., pyruvate, glucose, and glutamate), co-factors, enzymes and other reagents that are necessary for polypeptide services, e.g., ribosomes, tRNA, polyamines polymerase transcriptional factors, aminoacyl synthetases, chaperones, elongation factors, initiation factors, and the like. Other components that may be useful in a cell-free protein synthesis system are described in methods for cell-free synthesis are described in Spirin & Swartz (2008) Cell-free Protein Synthesis, Wiley-VCH, Weinheim, Germany.

In some embodiments, cell lysates (also referred to as lysates) used in the translation reaction may be prepared by lysing cells under conditions to preserve the transcription and/or the translationary machinery. Nonlimiting examples of the cell types that can be used to prepare cell lysates from include, E. coli cells, insect cells, yeast cells, Chinese hamster ovary cells, rabbit reticulocytes, wheat germ cells, and Hela cells. In some embodiments, cell lysates include components that are required for translation. Such components include a ribosome, amino acids, tRNA, tRNA synthetase, energy sources (Creatine phosphate), Creatine kinases, and/or any combinations thereof. Cell lysates and methods for their production are also disclosed in, Kuruma and Ueda Nature Protocols 10, 1328-1344 (2015) and Gregorio et al., Methods. Protoc. 2019 March; 2 (1): 24, the entire disclosures of which are herein incorporated by reference. Cell-free protein synthesis reagents are commercially available, for example, from New England Biolabs (Ipswich, MA).

If the hydrogel is a DNA hydrogel, it can be first transcribed into RNA using reagents and conditions suitable for an in vitro transcription, as discussed above, and then subject to the cell-free protein system disclosed herein.

A nucleic acid hydrogel disclosed herein, e.g., a W-RG4 gel, can produce proteins in high quantities. In one illustrative example, the protein expression yield of W-RG4 showed a 117-fold enhancement of expressing HiBiT, an 11 amino-acid peptide tag, over the free DNA template (fDNA) and an 8-fold enhancement over the free RNA (fRNA) template. Free DNA/RNA template refers to DNA/RNA that is in solution. See FIG. 5B.

Optionally, parameters such as chaotropic treatment, reaction time, temperature, volume can be modified to maximize the protein yield of the nucleic acid hydrogel protein production system. In one approach, the translation reaction is controlled so that it lasts no more than 12 hours, no more than 10 hours, no more than 6 hours, no more than 5 hours, no more than 4 hours, no more than 3 hours, or no more than 2 hours. In one exemplary assay, the protein production is shown to peak around 2 hours from the translation initiation. See FIG. 21A. To control the reaction time, after allowing translation to proceed for a predetermined length of time (e.g., 2, 3, 12, or 48 hours from the initiation of the translation), the reaction mixture is subjected to a high temperature, e.g., around 95° C., to denature the enzymes required for the translation, thereby terminating protein production. Alternatively, one or more chaotropic agents (e.g., 8M urea) can be added to terminate the translation.

In one approach, the reaction temperature is controlled at a temperature that is in a range from 16° C. to 37° C., e.g., 25° C. See FIG. 21D. In another approach, one or more reagents that can increase protein solubility, e.g., by solubilizing aggregated peptides, is added to the translation mixture improves the protein expression Nonlimiting examples of such reagents include surfactants, such as Tween-20, Triton X-100, CHAPS, or SDS. See FIG. 21B. In yet another approach, volume of the W-RG4 hydrogel added to the cell-free synthesis system can be optimized to increase protein production. In one embodiment, the volume of the W-RG4 used is in a range of 3 to 22 µL. In yet another approach, the volume of the translation reaction mixture (including the W-RG4) is controlled in the range of 50-200 µL, e.g., 150 µL, to achieve a high protein yield. See FIG. 21E.

Proteins can be harvested and purified at the conclusion of the translation process. Methods for protein purification, chromatography, electrophoresis, centrifugation, and crystallization are described in Coligan et al. (2000) Current Protocols in Protein Science, Vol. 1, John Wiley and Sons, Inc., New York.

Lysate-Embedded Hydrogel

In some embodiments, cell lysates as described above are added to the transcription reactions that generate RG4 concatemers. The hydrogels formed by these RG4 concatemers contain cell lysates and thus they are referred to herein as lysate-embedded hydrogels (e.g., lysate-embedded W-RG4 hydrogels). In contrast, hydrogels formed by transcripts in the absence of any cell lysates are referred to as lysate-free hydrogels. Unless specifically noted otherwise, a W-RG4 hydrogel disclosed in this disclosure is a lysate-free W-RG4 hydrogel.

The volume ratio of cell lysates to the transcription mixture (excluding the cell lysate) may vary. In some cases the volume ratio is in a range from 1:1 to 1:3, e.g., about 1:2, or about 1:2.5.

Surprisingly, these lysate-embedded hydrogels are able to produce proteins at a much higher yield than the corresponding lysate-free hydrogels under the same translation conditions, and the protein yield reached the peak level within a shorter time than the corresponding lysate-free hydrogels. A lysate-embedded W-RG4 and its corresponding lysate-free W-RG4 share the same nucleic acid components. One illustrative example is shown in FIG. 5J. FIG. 5J shows that when incubated with translation mixture that contains lysates prepared from E. coli cells for 3 hours, a lysate-embedded W-RG4 ("L-L-gel") produced a significantly higher amount of protein than the lysate-free counterpart ("Raw gel").

It has also been found that it is desirable to control the duration of the transcription reaction that is used to produce lysate-embedded hydrogels. Production efficiency of the W-RG4 hydrogels may decrease if transcription proceeds for relatively a long time (e.g., 48 hours). See FIG. 5I. Accordingly, in some embodiments, when using lysate-embedded hydrogels, the duration of the transcription reaction time is 48 hours or less, for example, 40 hours or less, 30 hours or less, 20 hours or less, 10 hours or less, 5 hours or less, or about 3 hours. In some embodiments, the duration of the transcription reaction is in a range from 1 hour to 40 hours, from 2 hours to 20 hours, from 2.5 hours to 10 hours, or about 3 hours.

In some embodiments, the lysate-embedded hydrogel is combined with a translation mixture that does not contain any cell lysates. As shown in FIG. 5J, the lysate-embedded hydrogel ("L-gel") was able to produce proteins in sufficient amounts when incubated with a feed solution (also known as a protein synthesis buffer) only and without any supplement of E. coli cell lysates during the translation process. The feed solution typically comprises amino acids, and one or more buffers and salts that are suitable for translation. In some embodiments, the feed solution also comprises an energy converting enzyme (e.g., a creaine kinase). This result suggests that the lysate-embedded W-RG4 may be useful in implantable or injectable therapeutic applications, where it is preferable or required that no external lysates were provided in the translation mixture.

Additional Modifications to Further Improve Protein Production

As disclosed above, the W-RG4 hydrogel can produce proteins in high-efficiency and high-yield. In some embodiments, the hydrogel is cut to improve the translation components' approachability, thus further improving translation efficiency. Cuts can be introduced by various means, for example, by piercing the hydrogel using pipette tips. The number of cuts made to the hydrogel is referred to as the cut-out number. In some embodiments, the W-RG4 has a cut-out number in the range of 250 to 400, e.g., about 300. One illustrative example is shown in FIG. 19, which demonstrates W-RG4 gel having a cut-out number of 300 can further increase protein production.

Kits

This application also provides kits for expressing a polypeptide of interest. In some embodiments, the kit comprises a single-stranded DNA molecule capable of forming a circular DNA template by hybridizing to a splint oligonucleotide. The circular DNA comprises (i) a promoter sequence, (ii) a sequence complementary to a G-quadruplex motif, and (iii) a coding sequence for a polypeptide of interest or a spacer. The splint oligonucleotide is complementary to the promoter sequence.

In some embodiments, the kit comprises a first single-stranded DNA molecule capable of forming a first circular DNA template by hybridizing to a first splint oligonucleotide, a second single-stranded DNA molecule capable of forming a second circular DNA template by hybridizing to a second splint oligonucleotide. The first circular DNA comprises (i) a first promoter sequence, (ii) a sequence complementary to a first G-quadruplex motif, and (iii) or a spacer. The second circular DNA comprises (i) a second promoter sequence, (ii) a sequence complementary to a second G-quadruplex motif, and (iii) or a spacer. The kit may further comprise the first splint oligonucleotide having a sequence that is complementary to the first promoter sequence and/or the second splint oligonucleotide having a sequence that is complementary to the second promoter sequence. In one embodiment, the first and/or the second split oligonucleotide has a sequence of SEQ ID NO: 12.

A kit disclosed herein may further comprise one or more reagents useful for performing the circularization of the DNA template and/or rolling circle transcription. These reagents include, but are not limited to, a ligase, an RNA polymerase, one or more ribonucleotide triphosphates (rNTPs), and a buffer suitable for transcription.

In some embodiments, the kit may further comprise one or more reagents suitable for the in vitro translation, such as, a ribosome, and a mixture of amino acids.

The following examples are offered for illustrative purposes, and are not intended to limit the invention. Those of skill in the art will readily recognize a variety of non-critical parameters that can be changed or modified to yield essentially the same results.

Embodiment 1. A first circular DNA template comprising (i) a first promoter sequence and (ii) a sequence complementary to a first G-quadruplex motif.

Embodiment 2. The first circular DNA template of embodiment 1, wherein the first promoter sequence is hybridized to a complementary nucleic acid sequence to form a first partially double-stranded DNA molecule, wherein the first partially double-stranded DNA molecule comprises a double-stranded region and a single-stranded region, wherein the double-stranded region comprises the first promoter sequence hybridized to the complementary nucleic acid sequence, and wherein the single-stranded region comprises the sequence complementary to the first G-quadruplex motif.

Embodiment 3. The first circular DNA template of any of the previous embodiments, further comprising a spacer, wherein the spacer comprises poly thymines.

Embodiment 4. The first circular DNA template of any of the previous embodiments, further comprising a coding sequence of a polypeptide of interest.

Embodiment 5. The first circular DNA template of any of the previous embodiments, wherein the sequence complementary to the first G-quadruplex motif comprises a sequence of ACCCTAACCCTA (SEQ ID NO: 1).

Embodiment 6. The first circular DNA template of any of the previous embodiments, wherein the first promoter sequence is selected from the group consisting of a T7 promoter, a T3 promoter, a Lac promoter, an araBad promoter, a Trp promoter, a Tac promoter, and an SP6 promoter.

Embodiment 7. A first nucleic acid concatemer comprising a plurality of monomers, wherein each monomer comprises (i) a first G-quadruplex motif, and (ii) a spacer comprising poly thymines or a coding sequence for a polypeptide of interest.

Embodiment 8. The first nucleic acid concatemer of embodiment 7, wherein the first nucleic acid concatemer is an RNA concatemer, wherein the first G-quadruplex motif comprises UAGGGUUAGGGU (SEQ ID NO: 2).

Embodiment 9. The first nucleic acid concatemer of any of embodiment 7-8, wherein the first nucleic acid concatemer is a DNA concatemer, wherein the first G-quadruplex motif comprises TAGGGTTAGGGT (SEQ ID NO: 20).

Embodiment 10. A nucleic acid hydrogel comprising the first nucleic acid concatemer of any of the embodiments 7-9.

Embodiment 11. A protein expression system comprising the nucleic acid hydrogel of embodiment 10, a ribosome, and/or a mixture of amino acids.

Embodiment 12. A composition comprising a first circular DNA template and a second circular DNA template, wherein the first circular DNA template comprises (i) a first promoter sequence, (ii) a sequence complementary to a first G-quadruplex motif, and (iii) a spacer comprising poly thymines, wherein the second circular DNA template comprises (i) a second promoter sequence, (ii) a sequence complementary to a second G-quadruplex motif, and (iii) a coding sequence of a polypeptide of interest; and wherein the molar fraction of the first circular DNA template relative to the total amount of first and second circular DNA templates ranges from 25% to 75%.

Embodiment 13. The composition of embodiment 12, (1) wherein the first promoter sequence is hybridized to a complementary nucleic acid sequence to form a first partially double-stranded DNA molecule, wherein the first partially double-stranded DNA molecule comprises a double-stranded region and a single-stranded region, wherein the double-stranded region of the first partially double-stranded DNA molecule comprises the first promoter sequence hybridized to the complementary nucleic acid sequence, and wherein the single-stranded region of the first partially double-stranded DNA molecule comprises the sequence complementary to the first G-quadruplex motif; and (2) wherein the second promoter sequence is hybridized to a complementary nucleic acid sequence to form a second partially double-stranded DNA molecule, wherein the second partially double-stranded DNA molecule comprises a double-stranded region and a single-stranded region, wherein the double-stranded region of the second partially double-stranded DNA molecule comprises the second promoter sequence hybridized to the complementary nucleic acid sequence, and wherein the single-stranded region of the second partially double-stranded DNA molecule comprises the sequence complementary to the second G-quadruplex motif Embodiment 14. The composition of embodiment 12 or 13, wherein the first G-quadruplex motif and the second G-quadruplex motif comprise the same nucleotide sequence.

Embodiment 15. The composition of any of embodiments 12-14, wherein the first promoter sequence and the second promoter sequence comprise the same nucleotide sequence.

Embodiment 16. The composition of any of the embodiments 12-15, wherein the first promoter sequence and the second promoter sequence comprise different nucleotide sequence.

Embodiment 17. The composition of any of the embodiments 12-16, wherein spacer comprises 30-120 thymines (SEQ ID NO: 32).

Embodiment 18. The composition of any of the embodiments 12-17, wherein the coding sequence has a length that is within a range from 20 to 300 nucleotides.

Embodiment 19. The composition of any of the embodiments 12-18, wherein the length ratio of the coding sequence to the spacer is within a ranges from 1:0.2 to 1:2.

Embodiment 20. The composition of any of the embodiments 12-19, wherein the polypeptide of interest is selected from the group consisting of insulin, Trans-activating transcriptional activator (TAT), HiBiT, and a single domain antibody.

Embodiment 21. The composition of any of the embodiments 12-20, further comprising one or more RNA polymerases, a mixture of ribonucleotides, and/or a buffer.

Embodiment 22. The composition of any of embodiments 12-20, further comprising a DNA polymerase having a strand replacement activity and thus is capable of performing a rolling circle amplification.

Embodiment 23. A composition comprising a circular DNA template and a double-stranded DNA construct, wherein the circular DNA template comprises (i) a first promoter sequence, (ii) a sequence complementary to a first G-quadruplex motif, and (iii) a spacer comprising poly thymines, wherein the double-stranded DNA construct comprises (i) a second promoter sequence, (ii) a sequence complementary to a second G-quadruplex motif, and (iii) a coding sequence of a polypeptide of interest.

Embodiment 24. A nucleic acid hydrogel comprising a first nucleic acid concatemer and a second nucleic acid concatemer, wherein the first nucleic acid concatemer is produced by rolling circle transcription or amplification of the first circular DNA template of the composition of any one of embodiments 12-20, and wherein the second nucleic acid concatemer is produced by rolling circle transcription or amplification of the second circular DNA template of the composition of any one of embodiments 12-20.

Embodiment 25. A nucleic acid hydrogel comprising a first RNA molecule and a second RNA molecule, wherein the first RNA molecule comprises (i) a first G-quadruplex motif, and (ii) a spacer comprising poly adenines, and wherein the second RNA molecule comprises (i) a second G-quadruplex motif, and (ii) a coding sequence for a polypeptide of interest.

Embodiment 26. The nucleic acid hydrogel of embodiment 25, wherein the first RNA molecule is a n RNA concatemer comprising a plurality of monomers and wherein each monomer comprising the first G-quadruplex motif, and the spacer comprising poly adenines or a coding sequence for a polypeptide of interest.

Embodiment 27. A protein expression system comprising the nucleic acid hydrogel of any one of embodiment 24-26s, a ribosome, and/or a mixture of amino acids.

Embodiment 28. A kit for expressing a polypeptide of interest, wherein the kit comprises (1) a first DNA molecule capable of forming a first circular DNA template by hybridizing to a first splint oligonucleotide, wherein the first circular DNA template comprises (i) a first promoter sequence, (ii) a sequence complementary to a first G-quadruplex motif, and (iii) a spacer comprising poly thymines,
(2) the first splint oligonucleotide that is complementary to the first promoter sequence, wherein the first DNA template can hybridize to first splint oligonucleotide and be circularized to form a first circular DNA template, and/or
(3) a second DNA molecule capable of forming a second circular DNA template by hybridizing to a second splint oligonucleotide, wherein the second circular DNA template comprises (i) a second promoter sequence, (ii) a sequence complementary to a second G-quadruplex motif, and (iii) a coding sequence of the polypeptide of interest,
(4) the second splint oligonucleotide that is complementary to the second promoter sequence, wherein the second DNA template can hybridize to the second splint oligonucleotide and be circularized to form a second circular DNA template.

Embodiment 29. A kit for expressing a polypeptide of interest, wherein the kit comprises the composition of any one of embodiments 12-23.

Embodiment 30. The kit of embodiment 28 or 29, wherein the first G-quadruplex motif and the second G-quadruplex motif have the same or different sequence.

Embodiment 31. The kit of embodiment 28 or 29, wherein the first promoter sequence and the second promoter sequence are the same or different.

Embodiment 32. The kit of any one of embodiments 28-31, wherein spacer comprises 30-120 thymines (SEQ ID NO: 32).

Embodiment 33. The kit of any one of embodiments 28-32, wherein the coding sequence has a length that ranges from 20 to 300 nucleotides.

Embodiment 34. The kit of any one of embodiments 28-33, wherein the length ratio of the coding sequence to the spacer is within a range from 1:0.2 to 1:2.

Embodiment 35. The kit of any one of embodiments 28-34, wherein the polypeptide of interest is selected from the group consisting of insulin, HiBiT, a Trans-activating transcriptional activator (TAT), and a single domain antibody.

Embodiment 36. The kit of any one of embodiments 28-35, further comprising one or more DNA ligases, RNA polymerases, a mixture of ribonucleotides, and/or one or more buffers.

Embodiment 37. The kit of any one of embodiments 28-36, further comprising a DNA polymerase having a strand replacement activity and thus is capable of performing a rolling circle amplification.

Embodiment 38. A method of preparing a nucleic acid hydrogel comprising: (1) providing a first circular DNA template comprising (i) a first promoter sequence, and (ii) a sequence complementary to a first G-quadruplex motif; and (2) performing a rolling circle transcription or amplification on the first circular template to produce a first nucleic acid concatemer, wherein the first nucleic acid concatemer forms a nucleic acid hydrogel.

Embodiment 39. The method of embodiment 38, wherein the first circular DNA template further comprises a spacer comprising poly thymines, wherein the step (1) further comprises providing a second circular DNA template comprising (i) a second promoter sequence, (ii) a second G-quadruplex motif, and (iii) a coding sequence of a polypeptide of interest, and wherein the step (2) further comprises performing a rolling circle transcription or amplification of the second circular DNA template to produce a second nucleic acid concatemer, wherein the first and second nucleic acid concatemers form the nucleic acid hydrogel.

Embodiment 40. A method for producing a protein in a cell-free synthesis system, wherein the method comprises: combining the nucleic acid hydrogel of embodiments 10 or 24-26 with a cell-free synthesis system under conditions permitting translation of the polypeptide of interest.

Embodiment 41. The method of embodiment 40, wherein the cell-free synthesis system comprises a ribosome and/or a mixture of amino acids.

EXAMPLES

Example 1. Materials

Sodium chloride, potassium chloride, sodium phosphate monobasic, sodium phosphate dibasic, agarose, DMSO (dimethyl sulfoxide), hemin, ABTS, and $H_2O_2$ were purchased from Sigma Aldrich. UltraPure Dnase/Rnase-Free distilled water, SYBR green II, ThT, and FBS were purchased from Invitrogen. 30% acrylamide-bis-acrylamide solution (29:1), APS (ammonium persulfate), and 10×TBE (Tris/boric acid/EDTA) buffer were purchased from PanReac Applichem. Biotin tyramide was purchased from Iris Biotech, and streptavidin was purchased from Rockland Immunochemicals. Urea was purchased from Daejung.

UltraPure Dnase/Rnase-Free distilled water was used for all experiments unless otherwise specified. The annealing protocol in this disclosure was a gradual cooling from 95° C. to 4° C. at 0.5° C./30 s unless otherwise specified.

Example 2. Preparation of the RG4 Hydrogels

The RG4 hydrogel was fabricated through self-assembly of RNA transcribed using rolling circle transcription (RCT). The circular template for the RCT was fabricated by ligating a linear template with the G-quadruplex moiety, a coding sequence for a protein of interest, and the T7 promoter. The linear template was annealed with a short strand containing a partial complementary sequence and a T7 promoter primer to form a circular template. The concentration of each strand was 45 μM in 100 mM NaCl. The annealed circular template was ligated with T4 DNA ligase (Promega). The concentration of the annealed template was 10 μM, and the volume of the buffer and T4 DNA ligase was provided by a T4 DNA ligase kit, in which 0.1× of the total ligation solution and the mixture were incubated at 16° C. for 16 hours. The RNA was transcribed using a Hiscribe T7 High Yield RNA Synthesis Kit (New England Biolabs) with 1 μM ligated circular template followed by incubation at 37° C. Although the maximum yield of RNA was expected to be reached after 2 hours of incubation, the process was continued for 48 hours after initiation of transcription. The same mole number of starting materials was used for all the templates.

Letolizumab-G4 in pIDTBlue plasmid (Integrated DNA technologies, Coralville, IA) was digested with NdeI and SalI and cloned into pK7 plasmid to generate the pK7-Letolizumab-G4 plasmid. 20 ng of plasmid was used as a positive control for cell-free expression, and 20 ng plasmid was transcribed together with 0.125 μM, 0.25 μM, 0.5 μM, 0.75 μM, or 1 μM spacer template for 60 T RG4 to induce gelation.

Example 3. Characterization of the Hydrogel

Rheology Analysis

The rheological properties of the RCT products were characterized by an ARES-G2 (TA Instruments) with 200 μL of the RCT products prepared in cylindrical molds.

Microscopic Analysis of the RG4 Hydrogels

Confocal microscope analysis. Thinly prepared RG4 hydrogel fabricated between cover glasses was stained with SYBR green II and visualized through an LSM 710 confocal microscope (Zeiss).

Field-Emission scanning electron microscope (FE-SEM) analysis. The RG4 hydrogel and RGx were frozen at −80° C. and lyophilized for 24 hours. The lyophilized samples were coated with iridium and characterized using SEM (JEM ARM200F, Jeol) at a voltage of 15.0 kV.

AFM analysis. Force-indentation curves for the RCT products were obtained using the ScanAsyst mode with commercially available DNP-S probe cantilevers (nominal spring constant of 0.12 N/m, tip radius of 10 nm, drive frequency of 16-28 kHz) with an aluminum reflux coating. The approach curve was used to measure the Young's modulus of the hydrogel by fitting a Hertzian contact mechanics model. The surface topography of the RCT products was analyzed using a multimode scanning probe microscope with a Nanoscope V controller (Bruker Inc.) in air using peak force tapping mode. The obtained topographical images were flattened to remove the background slope and contrast. We dispensed 30 μL of transcription mix onto the mica substrate to ensure flat fabrication of the RG4 hydrogel.

Streptavidin labeling. RCT products were prepared on mica and incubated with 200 μL of 100 hemin solution (20 mM phosphate buffer at pH 7.9, 1% DMSO, 0.1% Triton-X, 100 mM NaCl, 100 mM KCl) for 3 hours. Then 50 μL of 6 mM biotin tyramide (20 mM phosphate buffer at pH 7.9, 1% DMSO, 0.1% Triton-X, 100 mM NaCl, 100 mM KCl) and 50 μL of 4.5 mM $H_2O_2$ (20 mM phosphate buffer at pH 7.9, 1% DMSO, 0.1% Triton-X, 100 mM NaCl, 100 mM KCl) were added consecutively at 5 min intervals. We added 10 μL of 10 μM streptavidin solution after removing the reaction solution. Topographic analysis was conducted after thorough washing of unbound streptavidin using 100 mM KCl.

Spectroscopic Analysis of the RG4 Hydrogels

Quantification of RNA. The quantity of transcribed RCT products was measured with a Qubit Flex Fluorometer (Invitrogen) using an RNA BR Assay Kit (Invitrogen) after annealing to ensure the required 50x dilution.

CD spectroscopy. CD spectra were recorded to identify the conformational states responsible for the quadruplex and non-quadruplex RNA-developing analogs, sG4 and sGx, respectively, with a J-815 CD spectrometer (JASCO) in the wavelength range of 220 nm to 300 nm.

Characterization of the fluorescence signal from RG4-bound ThT. We mixed 10 μl of 1 μM sG4 and sGx with 40 μL of 10 μM ThT solution in 100 mM NaCl and 100 mM KCl and measured the fluorescence spectra ($\lambda_{ex}$=440 nm, $\lambda_{em}$=460-510 nm) through a fluorometer (SpectraMax M5, Molecular Devices) after 15 min.

Enzymatic activity of RG4-bound hemin. We incubated 10 μL of transcribed RCT products with 40 μL of 100 μM hemin solution (20 mM phosphate buffer at pH 7.9, 1% DMSO, 0.1% Triton-X, 100 mM NaCl, 100 mM KCl) for 16 hours. Then 25 μL of 3.2 mM ABTS 2-(20 mM phosphate buffer, varying pH from 4.4 to 7.9, 1% DMSO, 0.1% Triton-X, 100 mM NaCl, 100 mM KCl) and 25 μL of 0.3 mM $H_2O_2$ (20 mM phosphate buffer, varying pH from 4.4 to 7.9, 1% DMSO, 0.1% Triton-X, 100 mM NaCl, 100 mM KCl) were added consecutively to the solution with thorough mixing. The colorimetric change of the solution at $\lambda$=390 nm, caused by oxidation of $ABTS^{2-}$ into $ABTS^-$, was characterized continuously with a spectrophotometer (SpectraMax M5, Molecular Devices) for 4 hours.

Diffusion of ThT into the RG4 hydrogel. ThT solution at a concentration of 10 μM was added to RG4 hydrogel fabricated on a cover glass ensuring that no ThT was absorbed onto the top or bottom of the hydrogel.

Gel Electrophoresis Analysis

Polyacrylamide gel (PAGE) electrophoresis (12%) was used to characterize the annealed and ligated circular templates, and 2% agarose gel was used to characterize the transcribed RNA after annealing. Pre-cast Mini-PROTEAN® Tris-tricine SDS-PAGE gel (16.5%) was performed for the separation of Letoluzimab protein from the total cell-free expression.

Characterization of degradation. We mixed 10 μL of the RCT products with 40 μL of 100% FBS (fetal bovine serum) to provide an Rnase-rich environment. To characterize the total amount of RNA, samples were stored at −20° C. after each time interval to minimize the further effects of serum, followed by annealing for gel electrophoresis analysis using Weibull fit model.

Protein Expression

We used 11 μL of RCT products as templates for a 50 μL batch of uncoupled translations with a NEBExpress® Cell-free E. coli Protein Synthesis system (New England Biolabs). T7 polymerase, which was provided separately in the kit, was deliberately excluded. Translation was carried out at 25° C. for 2 hours, unless otherwise specified. We pierced the protein-encoded RG4 hydrogels with pipette tips to enhance the protein expression yield, and the gel cut 300 times showed the best yield. The ligated DNA templates (1 μM), fDNA and fRNA templates, and an equalized number of starting materials were used as control templates for coupled translation. For uncoupled translation, 11 μL of the 75% W-RG4 was mixed with wheat germ extract in a total volume of 50 μL at 25° C. for 2 hours, following the manual provided by the manufacturer except for fRNA where 10 μg was used. Varying volumes of template solutions were used to estimate protein efficiency.

For uncoupled translation of Letoluzimab, 12 μL of RCT products as templates for a 50 μL batch of uncoupled translations with a NEBExpression® Cell-free E. coli Protein Synthesis system (New England Biolabs). Translation kit components were used in which T7 polymerase was deliberately excluded. It was found that optimal protein expression were reached when the translation last for 8 hours at 30° C.

Characterization of Luminescence from Expressed HiBiT-tagged Protein

We mixed 2 μL of post-treatment translation product with 8 μL of HiBiT detection reagent in a Nano-Glo® HiBiT Extracellular Detection System (Promega). The resulting luminescent signal was characterized by a luminometer (SpectraMax M5, Molecular Devices) after 4 min of orbital shaking. Then, heat-inhibition at 95° C. for 10 mins was conducted. The mixture was incubated with an equal volume of 8 M urea for 2 hours to solubilize the aggregated protein. The relative luminescence units (RLUs) were normalized with respect to the luminescence of a blank cell.

Example 4. Design and Assembly of Programmed RNA Gel

A G-quadruplex motif from the secondary structure of the telomeric RNA repeat in nature (12, 13) were selected to fabricate a programmed DNA-driven RNA gel in which RNA transcribed from a DNA template serves as building blocks, crosslinkers, and functional items. We also embedded spacer sequences as poly thymines (poly T) or functional motifs such as a protein-encoding moiety in the assemblage. A single-stranded DNA template (any one of SEQ ID NO: 4-10) and the T7 promoter primer (SEQ ID NO: 12) were annealed to form circular DNA, followed by T4 enzymatic ligation (FIG. 1A and FIG. 6A). The RG4s were self-assembled into a 3-dimensional (3-D) gel through a secondary structured association of G4. An intentionally scrambled base sequence (Gx) (SEQ ID NO: 10) that cannot form G4 was made as a comparison group termed as RGx. RG4 and RGx were characterized through PAGE analysis. The RG4 gel, being a bulk structural entity, did not traverse and remained near the well, whereas the RGx migrated through the well (FIG. 6B).

Gelation of RG4 with respect to synthesis time was evaluated using vial inversion tests. In this experiment, gelation times were 0, 48 hours for RGx and 0, 3, 6, 9, 12, 24, 48 hours for RG4 from left to right (FIG. 1B). White arrows denote the location of the RCT products (gel phase in RG4 and solution phase in RGx). Gelated RG4 appeared as a single chunk material that exhibits strong elasticity with opposing gravitational force, whereas the RGx produced a viscous, non-gel solution that slid instantly to the bottom of the container, as shown in white downward arrows in FIG. 1B.

Figures 6A, 6B:
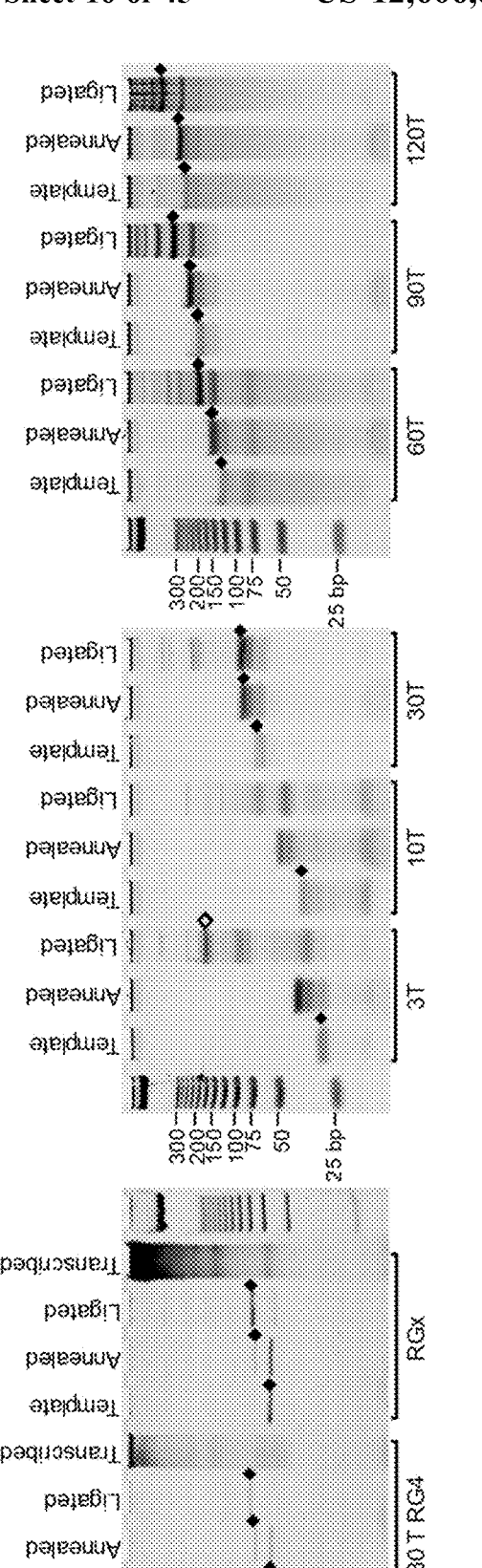
FIG. 6A-6D show the fabrication of DNA RCT template and transcription of the RNA products.
Figure 6C:
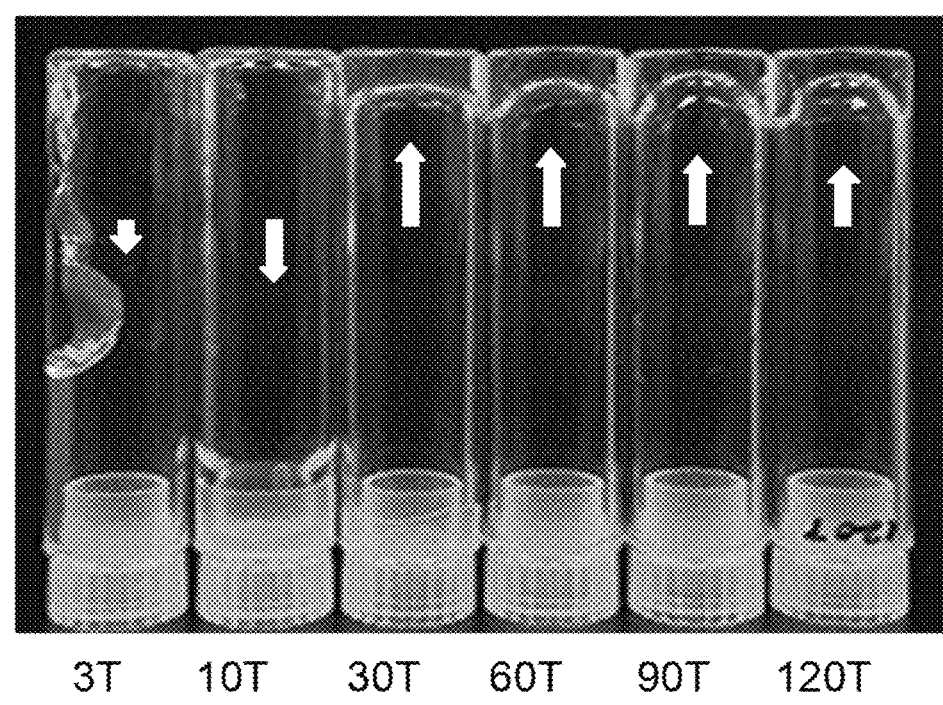
Figure 6D:
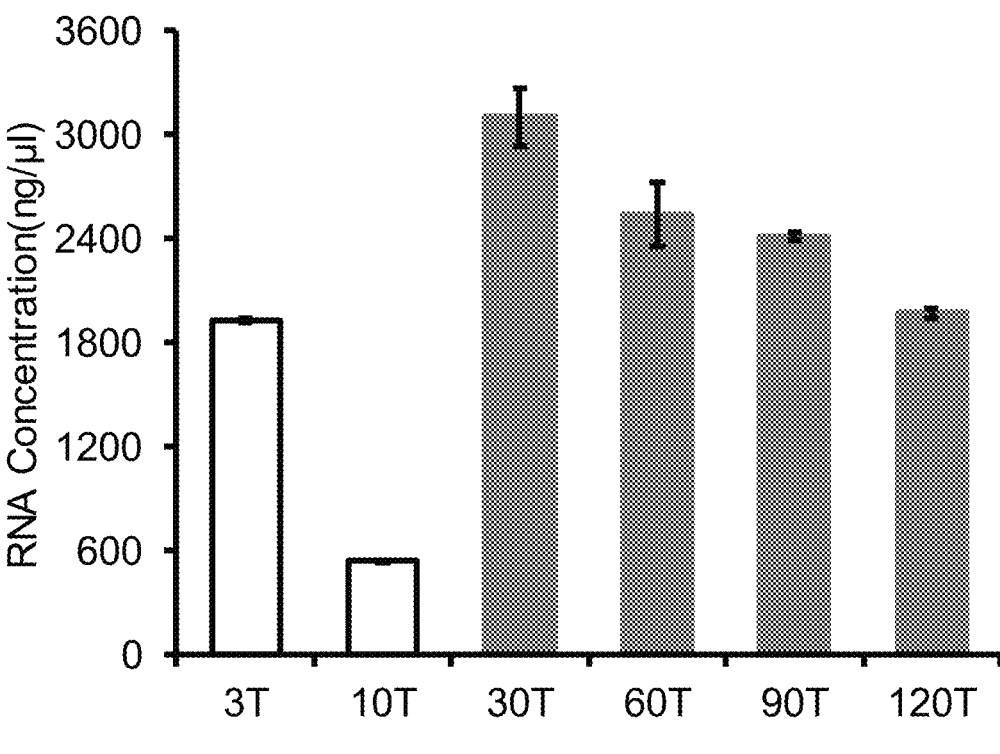
Figure 7:
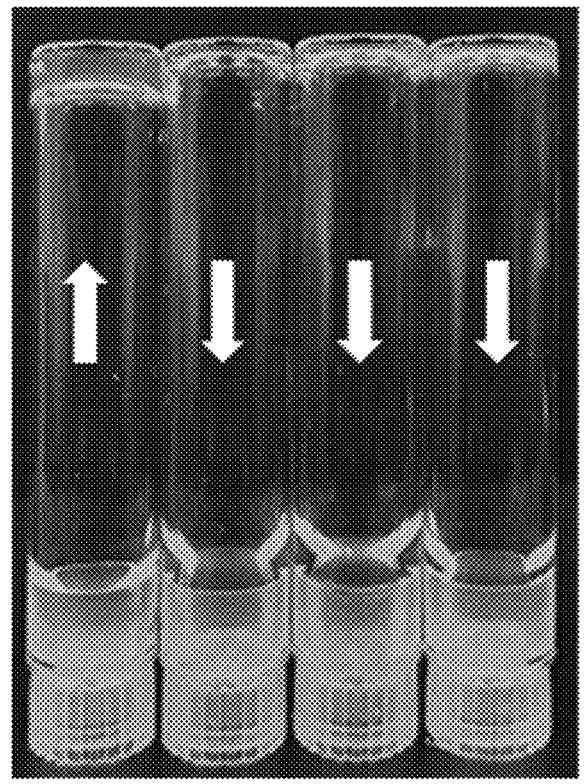
FIG. 7 shows the results of a recovery test for the RG4 gels. The recovery test was conducted to investigate whether the gelation process is reversible. The RG4 gels were first denatured at 95° C. for 2 hours. Then the denatured RG4 gel was annealed for 48 hour at 4° C., 25° C., or 37° C., the RG4 gels lost their self-assembling gel characteristics. Arrows facing up indicate a formed hydrogel, and the arrow facing down represents a liquid that failed to return to its gel state after the thermal treatment.
Figure 8A:
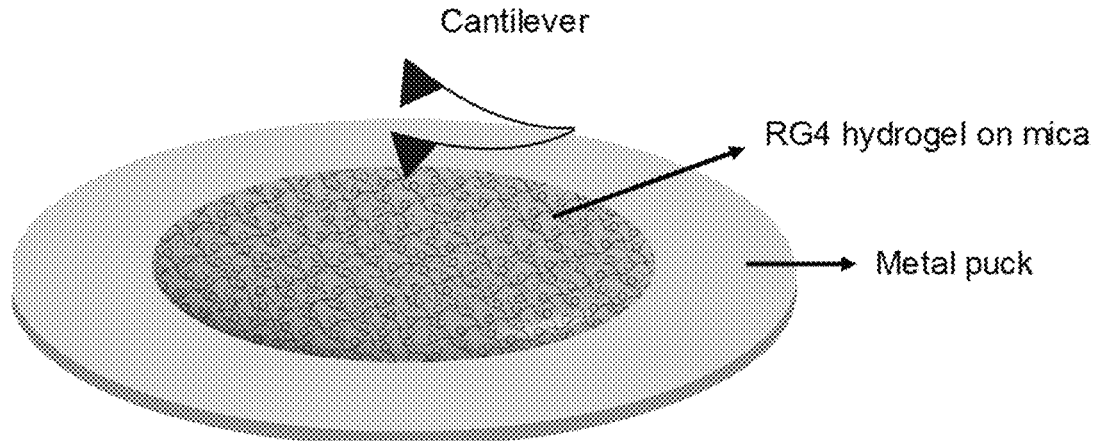
FIG. 8A-8H shows the AFM imaging of the RG4 gel for surface topology characterization.
Figures 8B, 8C, 8D, 8E:
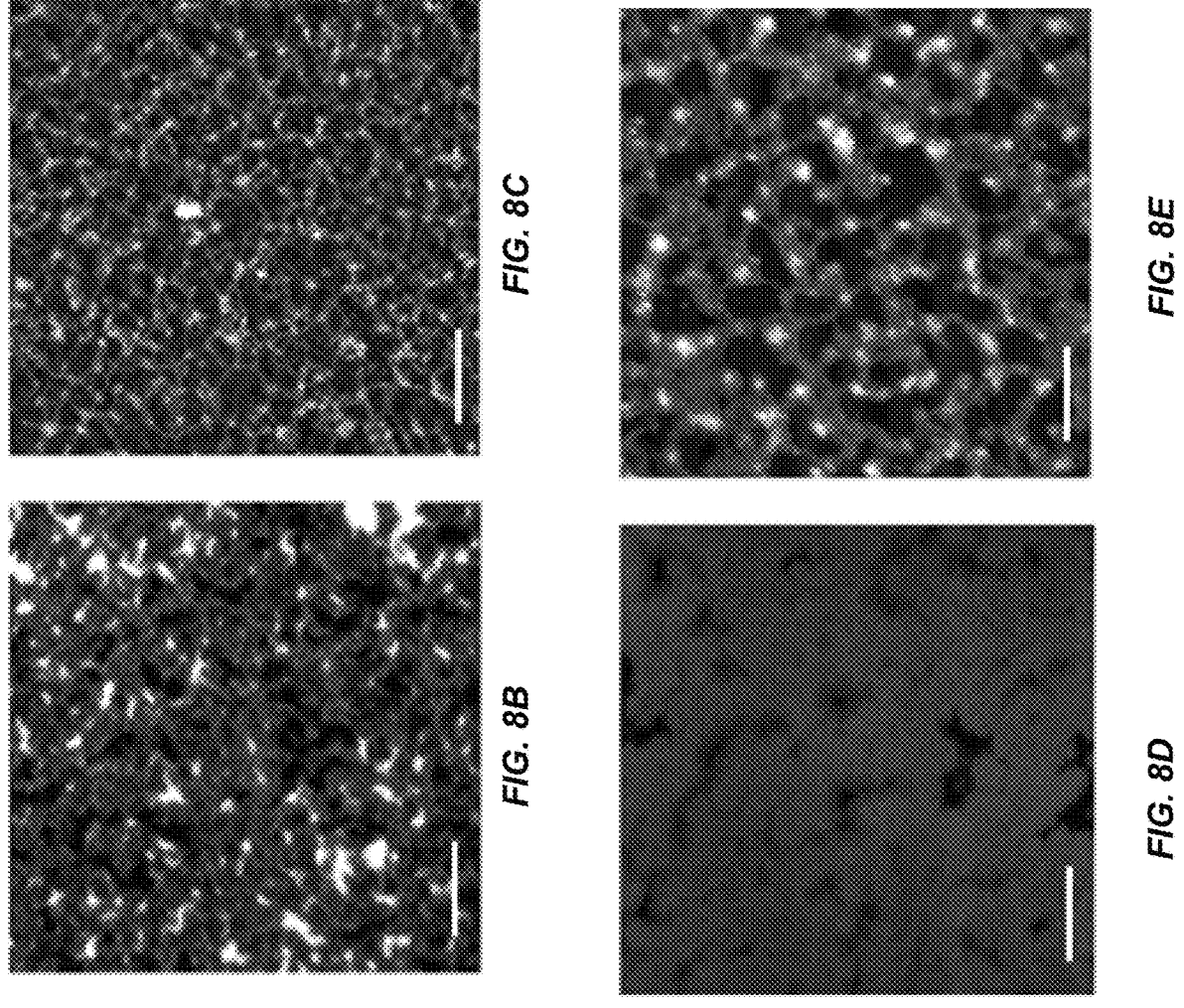
Figures 8F, 8G, 8H:
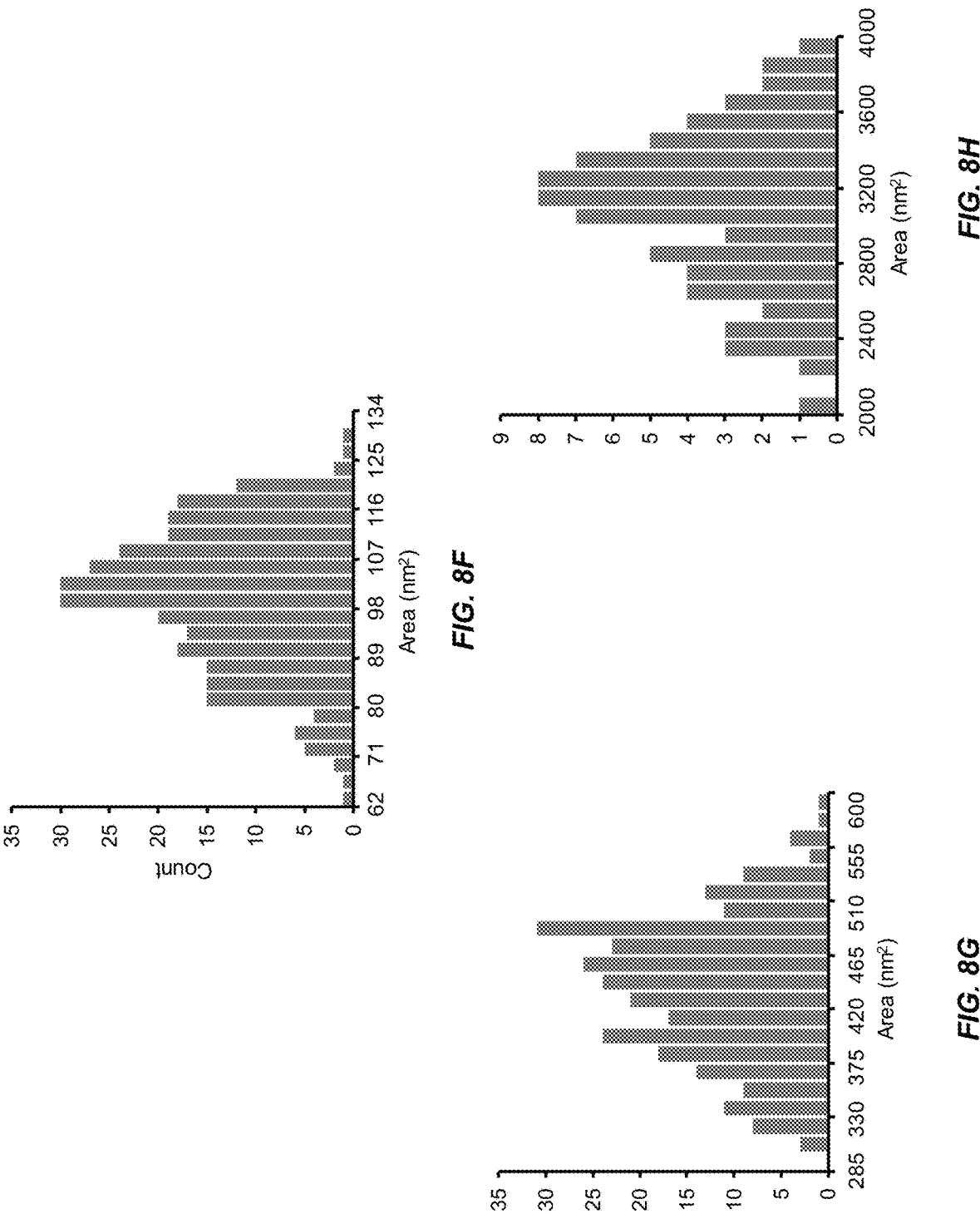
Figures 11A, 11B:
FIG. 11A-11F show the circular dichroic (CD) analysis of the synthetic sG4 and sGx under various salt conditions. Dose-dependent CD spectra from the synthetic RNA analogs with a G-quadruplex moiety (sG4) and a scrambled G-quadruplex moiety (sGx). Alterations were anticipated in the ellipticity spectra for sG4 and the stability of the RNA segments with respect to the salt concentrations (KCl, NaCl, and $MgCl_2$ as in FIGS. 11A, 11B, and 11C, respectively). Prominent peaks at 264 nm and a trough at 240 nm were observed for sG4 in the presence of KCl and NaCl, but not in the presence of $MgCl_2$. Monovalent cations, especially $K^+$ and $Na^+$, fit specifically into the cavity between the two guanine tetrads, stabilizing the G-quadruplex structure by means of their appropriate ionic radius for complex formation. By varying the concentration of the salt solution from 0.1 mM to 100 mM of KCl, NaCl, or $MgCl_2$, the peak at 260 nm increased in a concentration-dependent manner with KCl and NaCl, whereas no meaningful change was observed with $MgCl_2$ for sG4. The structure-activity relationship between the scrambled, non-gelating sGx oligonucleotides and the cations did not differ in secondary structure profiles between the mentioned salt conditions and the no-salt condition as displayed in FIGS. 11D, 11E, and 11F.
Figure 11C:
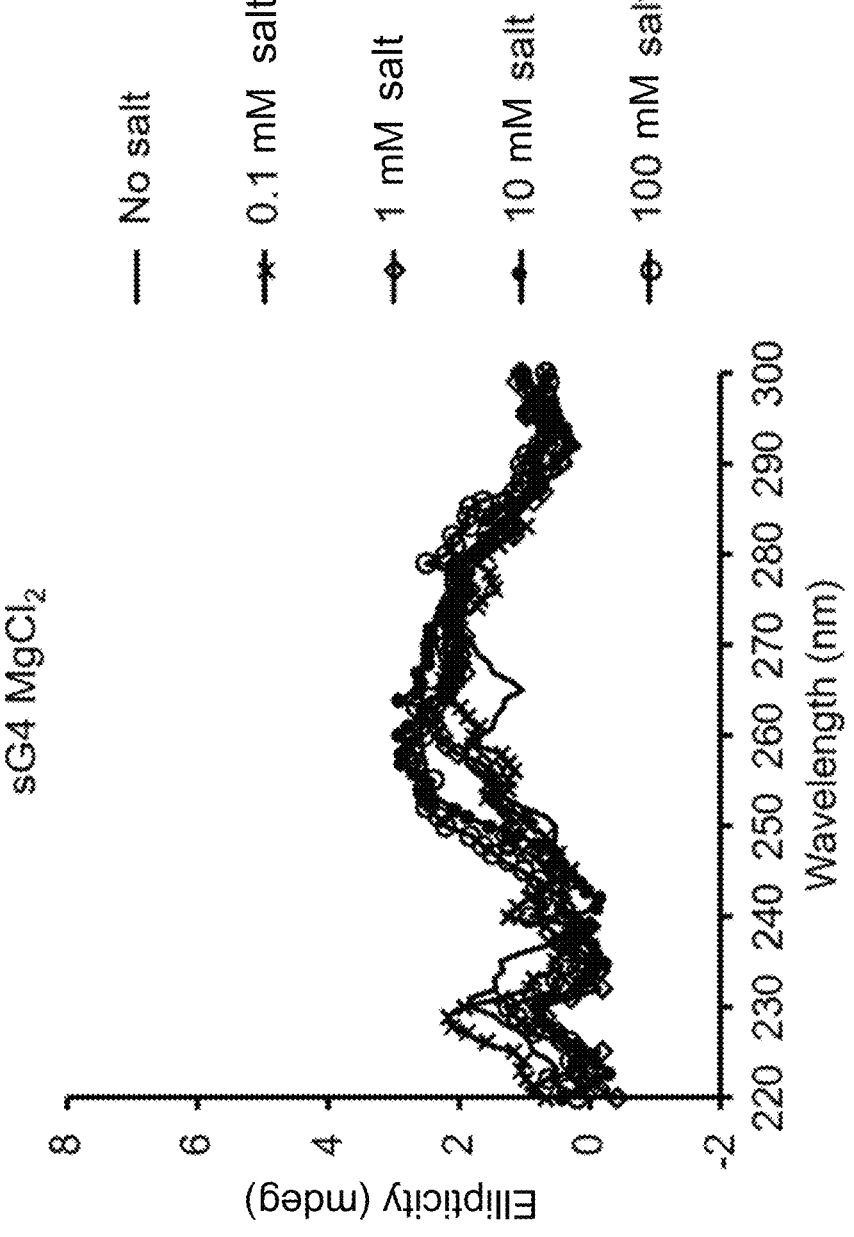
Figures 11D, 11E:
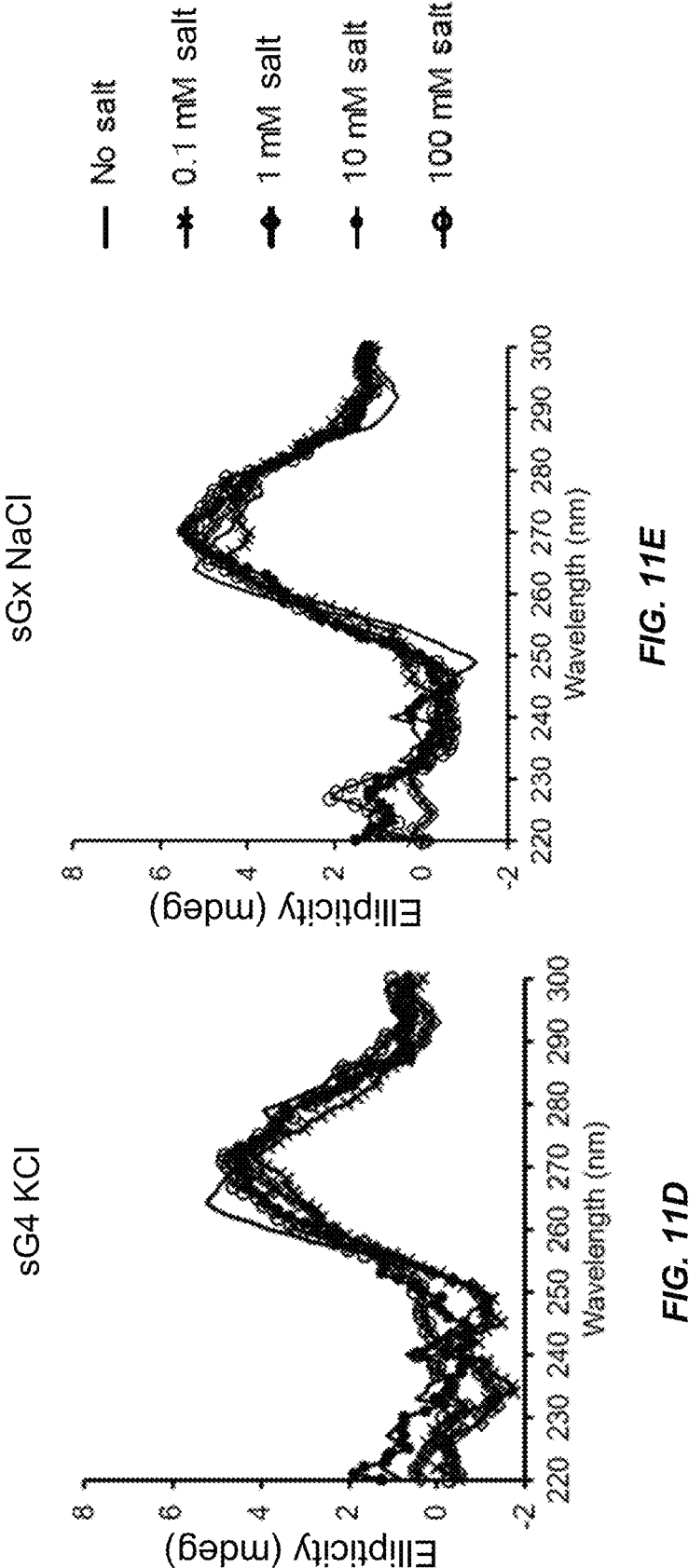
Figure 11F:
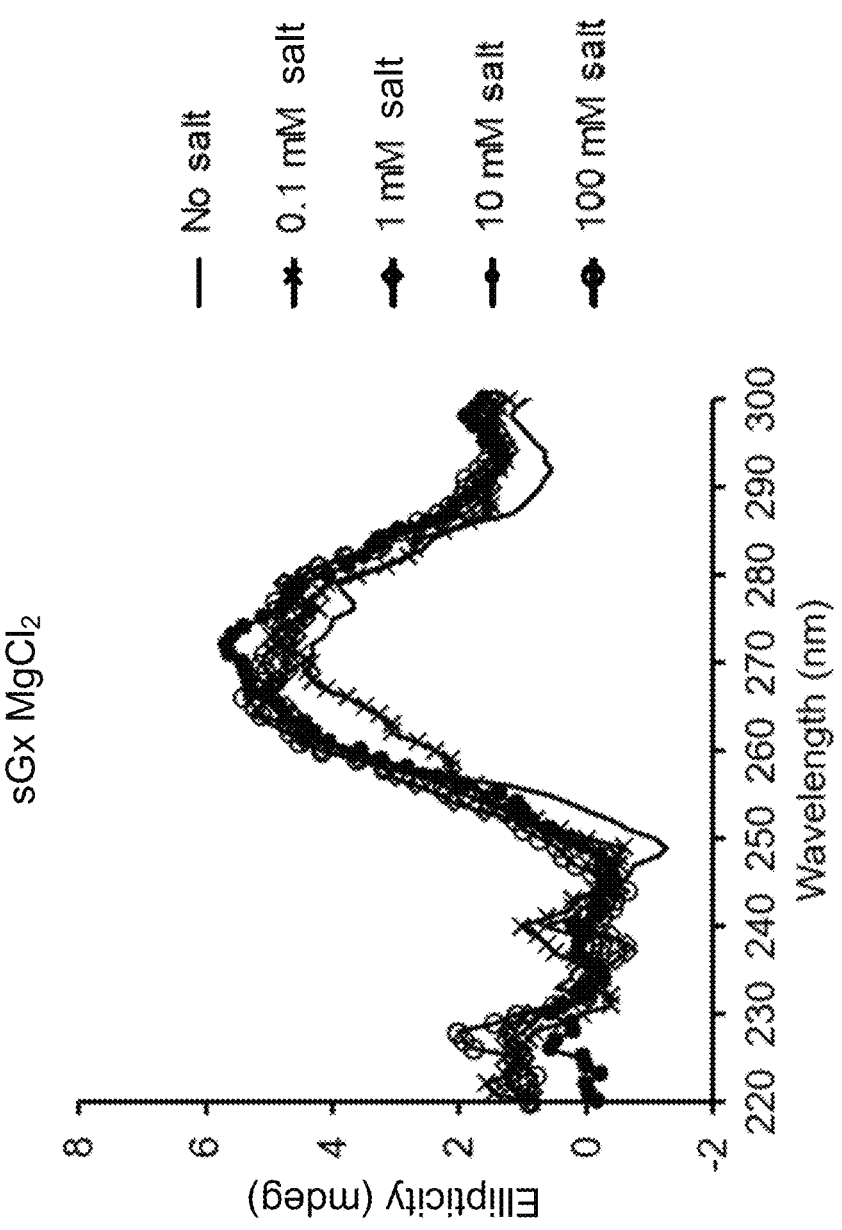
Figure 12A:
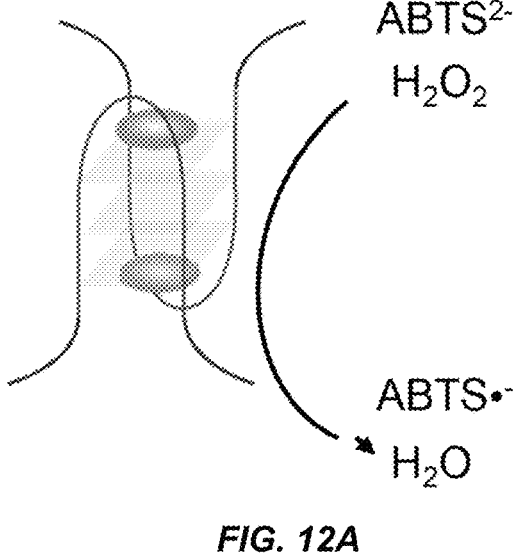
FIGS. 12A, 12B, 12C, 12D, 12E, 12F, 12G, and 12H show optimization of the peroxidase-like activity of hemin in RCT products with and without G-quadruplex. Schematic representation of the G-quadruplex interaction with hemin for oxidative catalysis of an ABTS substrate in the presence of $H_2O_2$. The time- and pH-dependent kinetics of the RCT products in the catalytic reactions were tested over a pH range of 4.4 to 7.9. The kinetic behavior between hemin and the RG4 gel complex during oxidation of $ABTS^{2-}$ to $ABTS^-$ was characterized by an absorbance increase at $\lambda=395$ nm. RG4 gels exhibited improved peroxidase activity in the pH range of 4.4 to 7.9 because the enzymatic reaction was resistant to pH, assisting in both the stability of the product formed and the enzymatic reaction. RGx products displayed a similar trend, although the increase in peroxidase activity was slower than RG4, indicating a possible minor interaction between hemin and the self-enclosed modules. RG4 and RGx exhibited valid enzymatic activity with the reaction buffer in the pH range of 5.4 to 7.9, whereas no or negligible activity was observed for free hemins because of the deprotonation of hemin in the RCT complexes and because of their vulnerability towards $H_2O_2$ in a basic environment and have low activity (43, 44). Therefore, hemin-RG4 gel displayed enhanced peroxidase activity compared with RGx, though the activity of free hemin was nullified at pH>4.9.
Figure 12B:
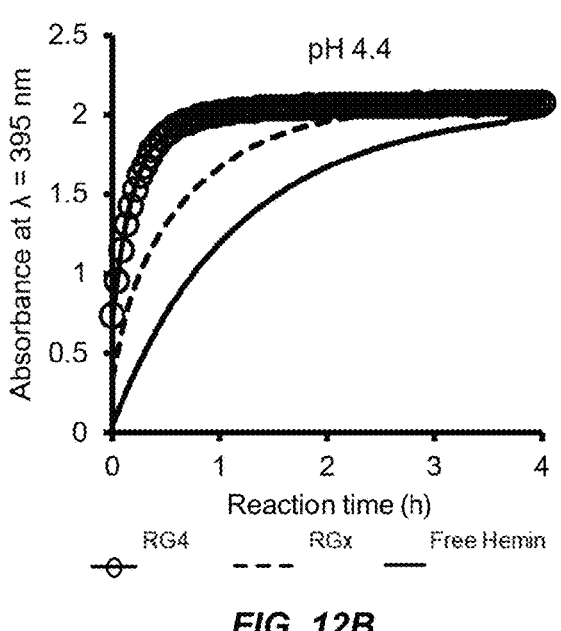
Figure 12C:
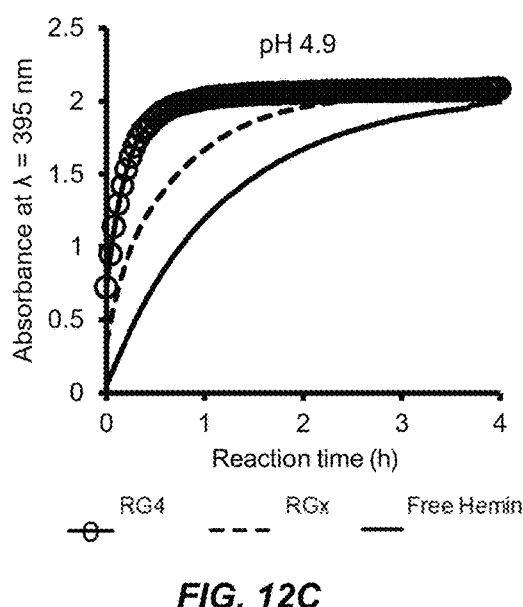
Figure 12D:
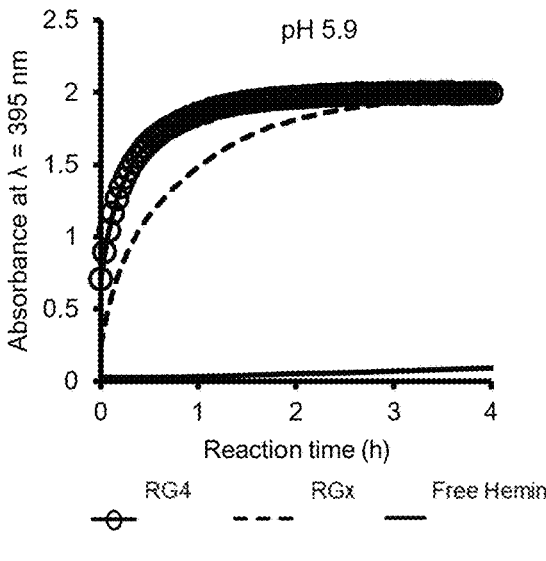
Figures 12E, 12F, 12G, 12H:
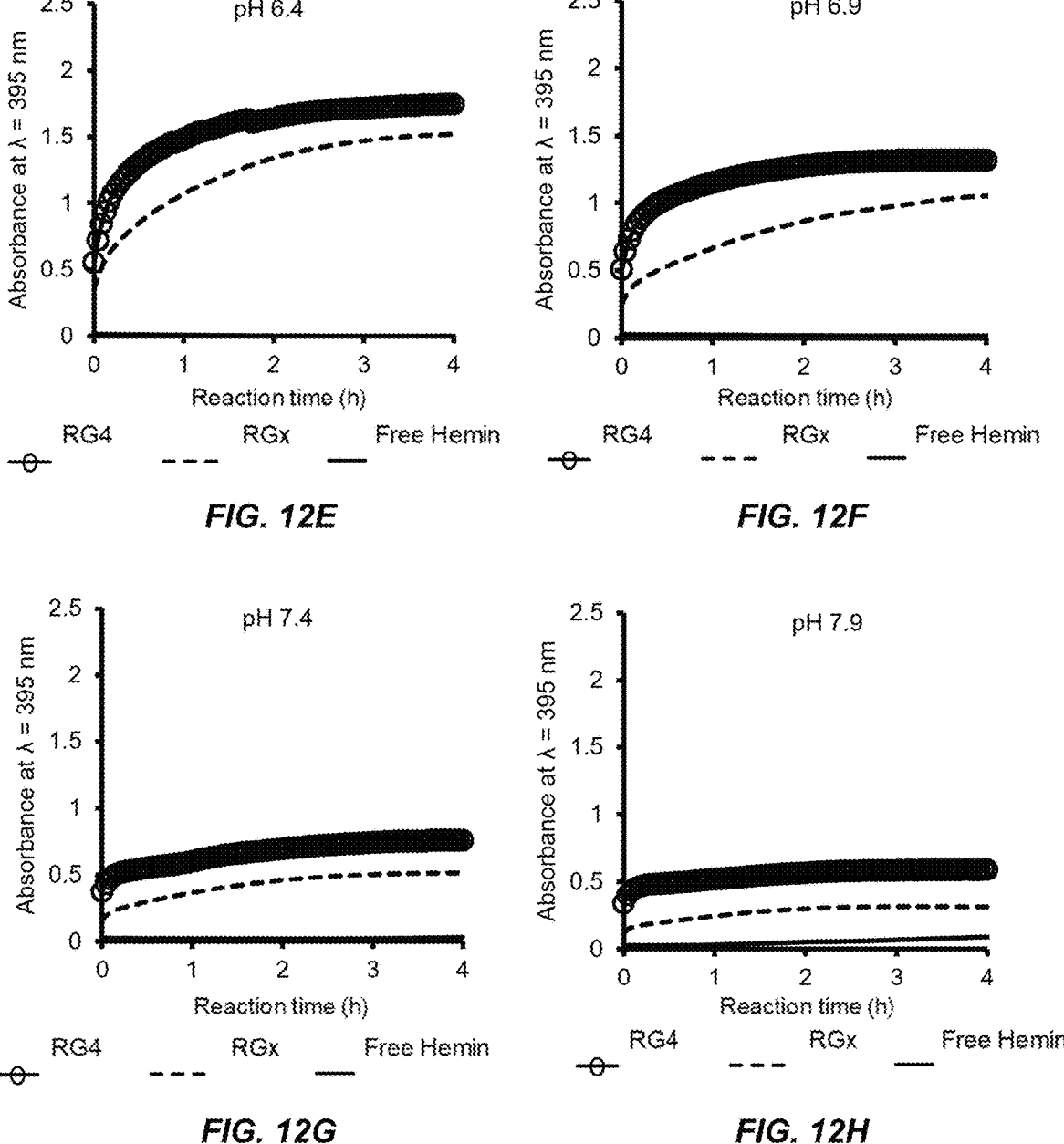

Spacer lengths with varied numbers of thymines (3T, 10T (SEQ ID NO: 38), 30T (SEQ ID NO: 33), 60T (SEQ ID NO: 34), 90T (SEQ ID NO: 35), and 120T (SEQ ID NO: 36)) were also tested to evaluate the versatile gelating behavior of RG4 (FIGS. 6B and 6C). Spacers with 30T (SEQ ID NO: 33) to 120T (SEQ ID NO: 36) gelated completely through successful construction of a circular template, and enhanced transcription yield was observed. Interestingly, RG4s with short spacers of 3T and 10T (SEQ ID NO: 38) did not gelate and remained in solution state because the steric length was insufficient for a linear DNA to circularize (14) (FIGS. 6B and 6D). Remarkably, annealed RG4 gels lost their gel characteristics and never regained them, even after incubation at various temperatures (FIG. 7). Thus, delayed formation of the G4 crosslinkers coupled with transcription was essential for successful fabrication of RG4 gel. Topological differences in pore sizes of RG4 gels with various spacer lengths were assessed using the average area under the pore from atomic force microscopy (AFM) images: 100.1 nm², 437.2 nm², and 3071.6 nm² for 30T (SEQ ID NO: 33), 60T (SEQ ID NO: 34), and 120T (SEQ ID NO: 36) spacers, respectively (FIG. 8).

We precisely patterned the RG4 gels into circular, triangular, rectangular, and star shapes (FIG. 1C) and a 3-D cylindrical shape (FIG. 1D) at the centimeter and micrometer scales (FIG. 9A). Characterization of the pores and crosslinking in the gel matrix was confirmed (FIG. 1E and FIG. 9B). The freeze-dried RG4 gel showed a wrinkled surface morphology that corresponded to the interconnected pores or scaffolded nature of the RNA gel. In comparison, RGx failed to form a gel; instead it displayed a regular, unfurrowed morphology without pores (FIG. 10)

Example 5. Verification of G-quadruplex Crosslinker in the RNA Gel Matrix

The structural features of the engineered RG4 concatemer (comprising SEQ ID NO: 2) and their specific responses to the dose of salt solution were analyzed through the ellipticity changes in their circular dichroism (CD) spectra, which exhibited a parallel fold of the G-quadruplex (15-17) (FIG. 2A and FIG. 11). To detect the ability of the RNA concatemers (sG4, comprising SEQ ID NO: 2, and sGx, comprising SEQ ID NO: 13) to form G-quadruplex structures, a fluorescent turn-on ligand, thioflavin T (ThT), was used (18, 19). Significant enhancement in fluorescence intensity was observed at 488 nm (FIG. 2B), demonstrating the specific binding of ThT probe to the RG4s.

The ability of the RG4 gel to perform peroxidase activity when complexed with hemin was investigated to validate the existence and intrinsic function of the G4s in the RG4 gel in a pH range from 4.4 to 7.9 (FIG. 2C and FIG. 12). Interaction of the G4 domains with hemin caused a significant enhancement in peroxidase activity, characterized by colorimetric change of 2,2'-azino-bis-3-ethylbenzothiazoline-6-sulfonic acid (ABTS). The improved peroxidase activity and overall efficiency across a wide pH range indicated that the G4 crosslinking in the gel directed the enzymatic activity, in addition to being a scaffold (20, 21). The intrinsic activity of the G4 module with hemin was also used to visualize G4 by means of self-biotinylation and streptavidin binding in AFM images (22). A difference in height profile was observed through brightened spots, for RG4 (before and after treatment), while RGx lacked such brightened spots, confirming the absence of G4 and self-biotinylated sites (FIG. 13).

Example 6. Changes in Physico-Chemical and Mechanical Behavior of the RG4 Gel The Young's modulus of the RG4 gels was tested to assess the gels' mechanical properties. The Young's modulus determined through a compression test on the centimeter scale was 38.4 kPa, obtained from the slope of the curve (23) (FIG. 3A). The modulus was notably in the range for previously reported soft gels (24, 25). In addition, an AFM-based indentation test method on the nanometer scale was used to analyze the elastic modulus of soft and hydrated samples using force curves (26, 27). Time-dependent increase in modulus that corresponded closely with the vial inversion tests (FIG. 1B) was observed and it was ~10.93 kPa at 48 hours (FIG. 14A and FIG. 14B), which was significantly higher than that reported for DNA-based gels (28). The storage modulus was invariably higher than the loss modulus at 24 hours (FIG. 14C and FIG. 14D), suggesting that the solid-like nature was dominant, due to the crosslinked regions in the RG4 gel (29, 30) (FIG. 3B).

The water retention and absorption capacity of the RG4 gel were analyzed by measuring the volumetric dehydration and rehydration ratio of the gel (31) (FIG. 3C and Equation (1), discussed above). Our pristine RG4 hydrogel exhibited an excellent water retention capacity, with a swelling degree of 1164.1%, and it held 1064.1% of its original volume owing to the strong interaction between water and the hydrogel network (28). Additionally, the RG4 hydrogel was capable of undergoing swelling-deswelling cycles, exhibiting a re-swelling degree up to 734.2% (FIG. 3C). These properties are responsible for the enhanced transcription yield (FIG. 6D), by resisting the reaction lag caused by a viscous environment.

We analyzed the behavior of ThT and ribosome diffusion into the porous hydrogel both experimentally and theoretically. The distance traveled by the ThT was captured on confocal microscope which was 573.4 μm in 1550 s (FIG. 3D). We chose a model to corroborate our theoretical assumptions, which defined the diffusivity of molecules transported in a porous medium (32) (Equations (2)-(6), discussed above). The time required for a ribosome to completely diffuse into a 20-μm deep hydrogel (33) using theoretical estimations 1 and 2 were 1.8 seconds and 2.2 seconds, respectively (FIG. 3D and Table 2 below).

TABLE 2

| | | Diffusion velocity (m/s) | Time required for diffusion (s) |
|---|---|---|---|
| Thioflavin T (573.3 μm, 20° C.) | Experimental measurement | $3.70 \times 10^{-7}$ | 1550 |
| | Theoretical estimation 1 | $5.31 \times 10^{-7}$ | 958.6 |
| | Theoretical estimation 2 | $5.16 \times 10^{-7}$ | 987.4 |
| Ribosome (20 μm, 37° C.) | Theoretical estimation 1 | $5.58 \times 10^{-6}$ | 1.8 |
| | Theoretical estimation 2 | $4.59 \times 10^{-6}$ | 2.2 |

The diffusion velocities of the ligands indicate that they are not only able to move freely within the hydrogel network, but also permits ingress and egress of reagents through its controllable pore size. Pore size was estimated based on the average distance calculated between the G4 structures in the RG4 hydrogel and the pore size estimation from the AFM image (FIG. 3E and FIG. 15).

Figures 4A, 4B, 4C:
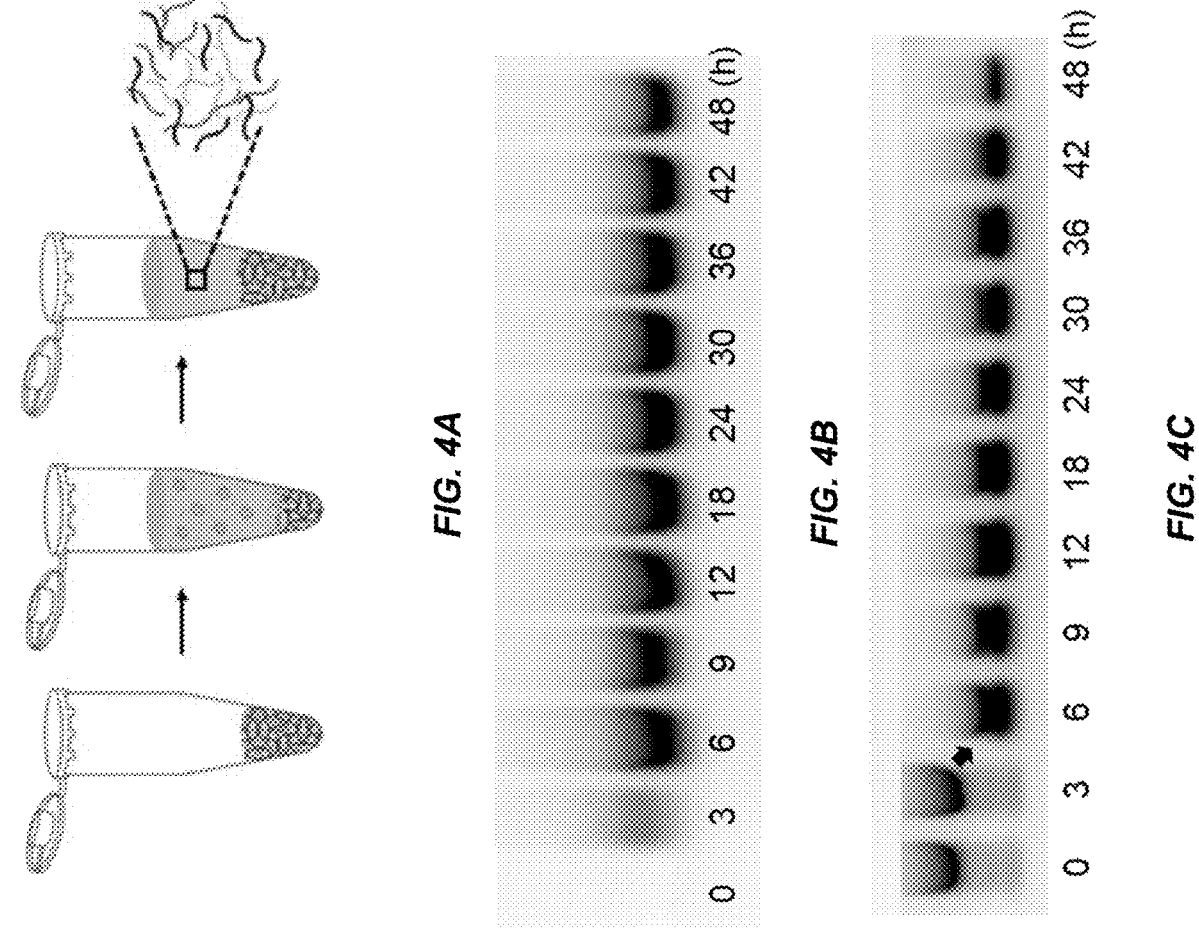
FIG. 4A-4F show the stability of the RG4 hydrogel in RNAse-rich FBS serum.
Figure 4D:
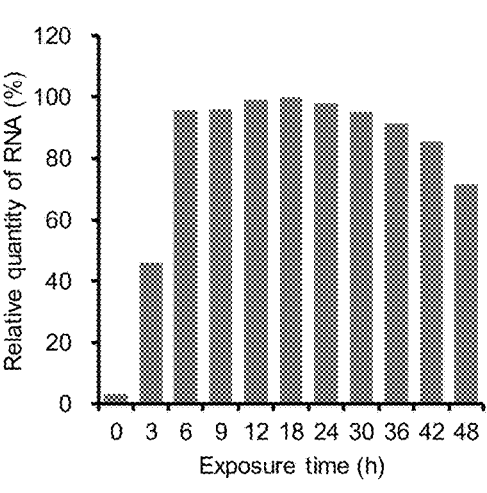
Figure 4E:
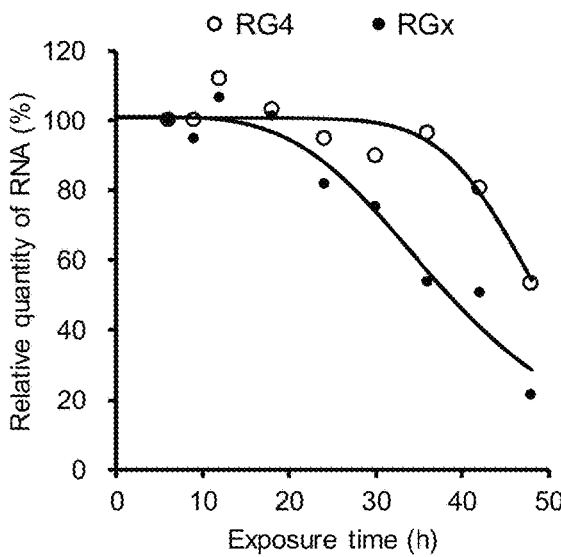
Figure 4F:
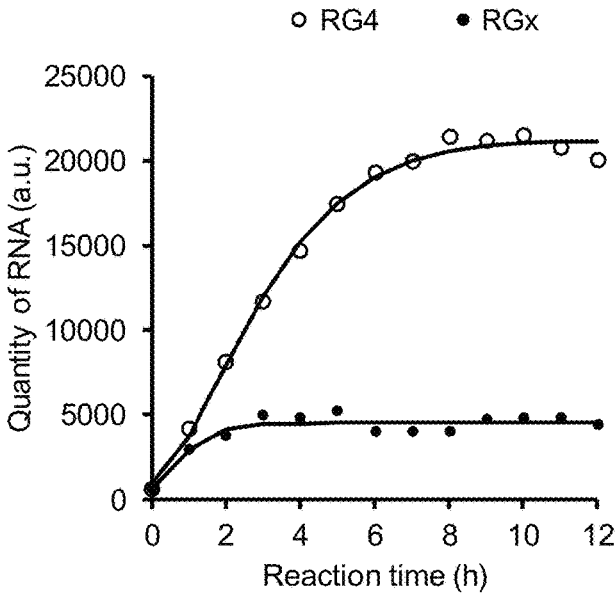
Figure 16A:
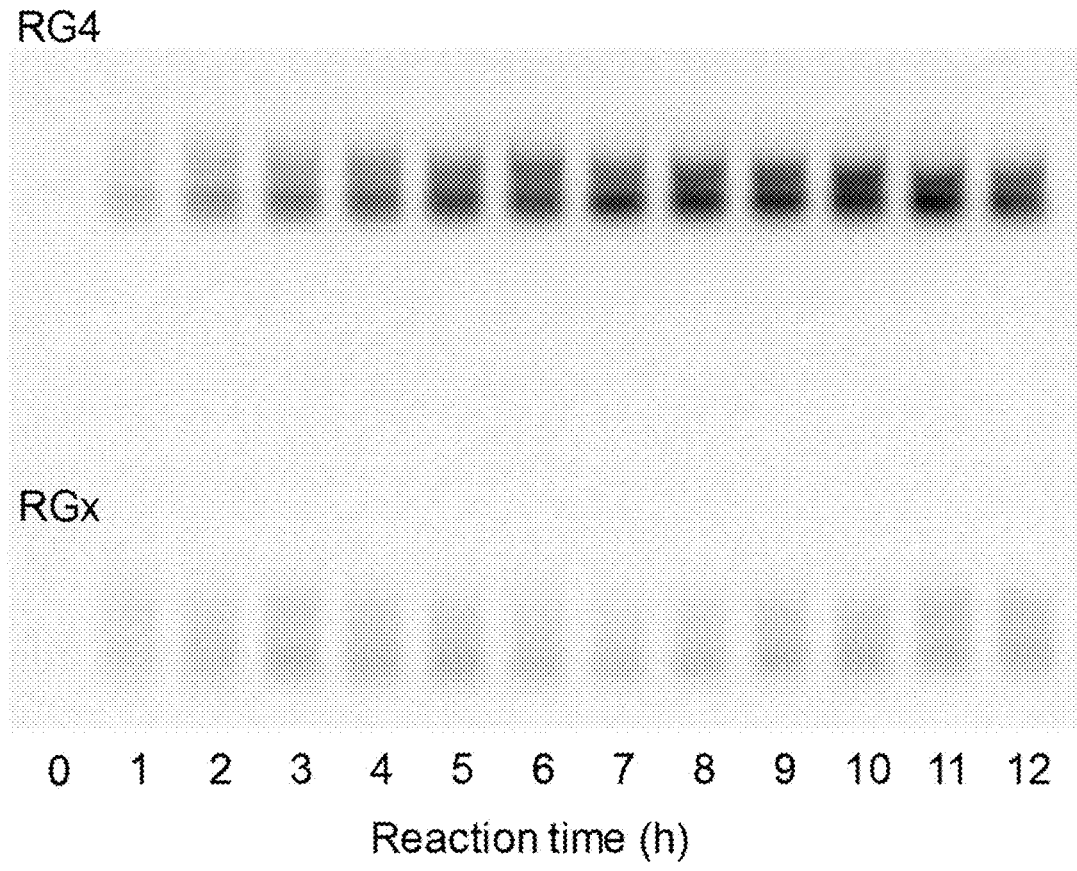
FIGS. 16A and 16B show the representative electropherograms envisioning the stability of RCT products in the serum. The responsiveness (existence or degradation) of the RNA hydrogel towards RNase-rich fetal bovine serum (FBS) at different exposure times was demonstrated using gel electrophoresis to evaluate the stability of the RG4 hydrogel.
Figure 16B:
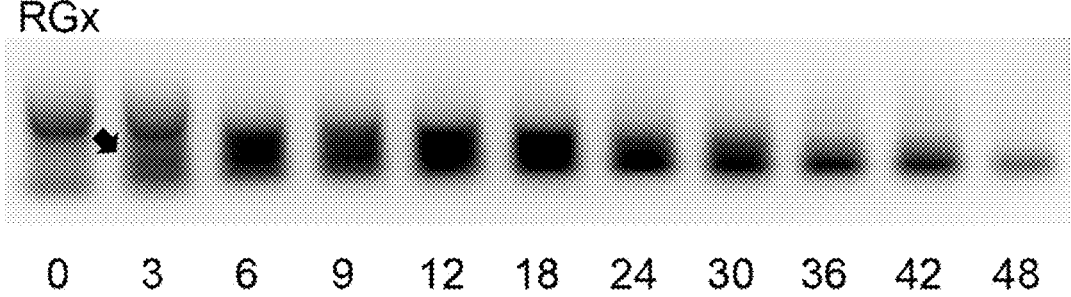

Degradation study (FIG. 4A) was evaluated chronologically for the amount of RNA in the RG4 and RGx (the RG4 gel and the supernatant) was performed using agarose gel electrophoresis (FIG. 4B, FIG. 16). Negligible quantity of RNA was present in the RG4 supernatant until 3 hours, whereas up to 74% of RNA was observed at 48 hours (FIG. 4C and FIG. 4D). RG4 was able to withstand its RNA for a longer period (i.e., 48.9 hours) than the RGx (i.e., 38.3 hours), with respective quantities of 53.4% and 21.6%. The RGx degraded faster than the RG4 under the same conditions because of the highly integrated nature of the RG4 hydrogel and enriched RNA quantity in gel form compared with solution phase (11) (FIG. 4E). The amount of RNA in the RG4 continued to increase which had higher yield at 12 hours, unlike the RGx (FIG. 4F). The increased amount of RNA observed from the enhanced transcription yield and low degradation rate will also contribute to the improved protein yield resulted from translating these RNAs.

Example 7. Enhancement of the Expression of Various Proteins by the RG4 Hydrogel

1. HiBiT

Figure 5A:
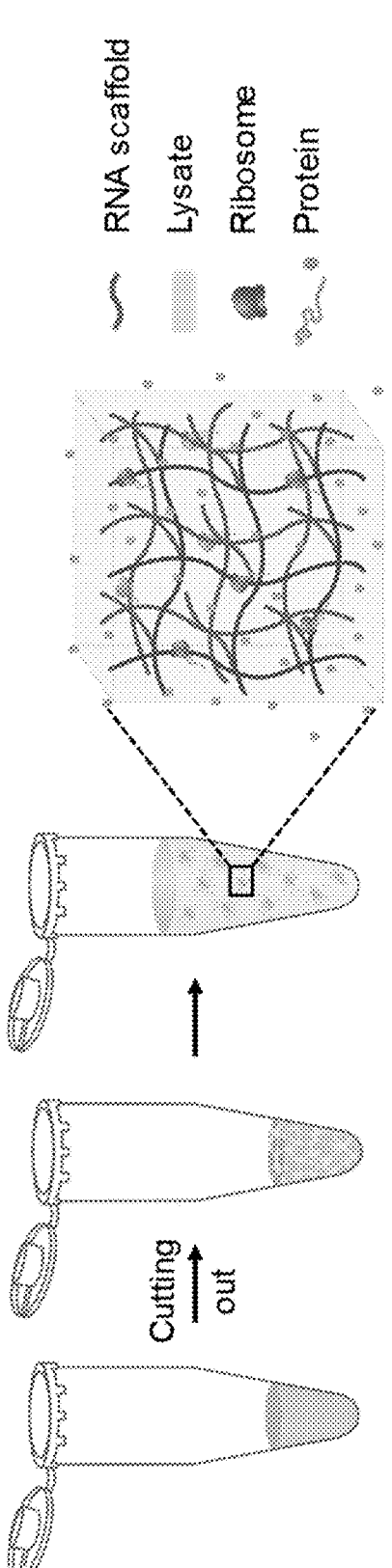
Figure 5E:
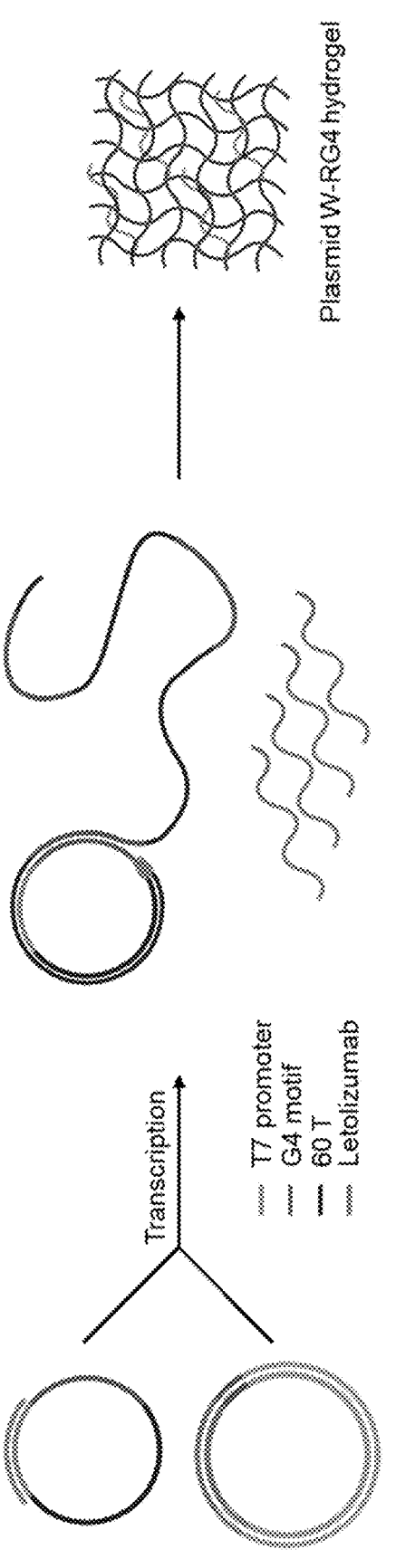
FIG. 5E is a schematic representation of the wideband RG4 hydrogel (W-RG4) using plasmid cloning technique. A W-RG4 hydrogel is produced by integration of 60T RG4 transcribed from the spacer template comprising the sequence of SEQ ID NO: 7 with the RNA transcripts from the vector pK7-Letolizumab.
Figure 5F:
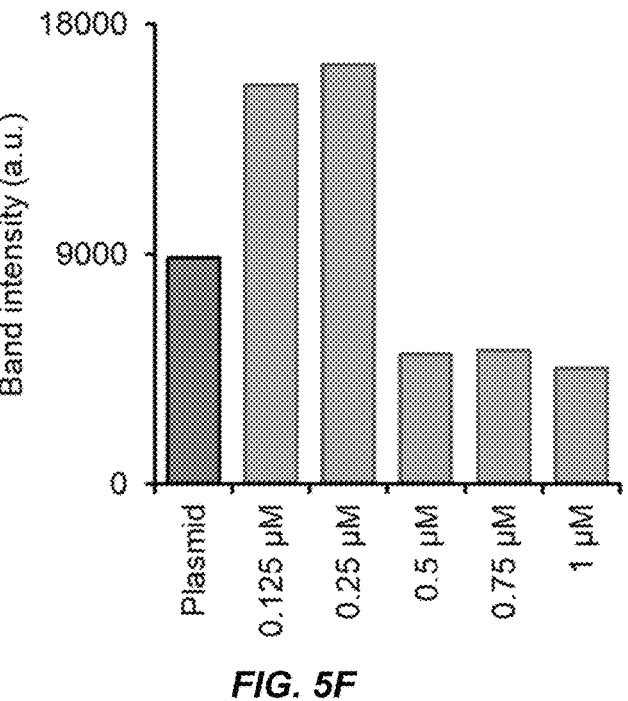
FIG. 5F shows the results of quantifying the intensity of the detected bands corresponding to Letolizumab.
Figure 5G:
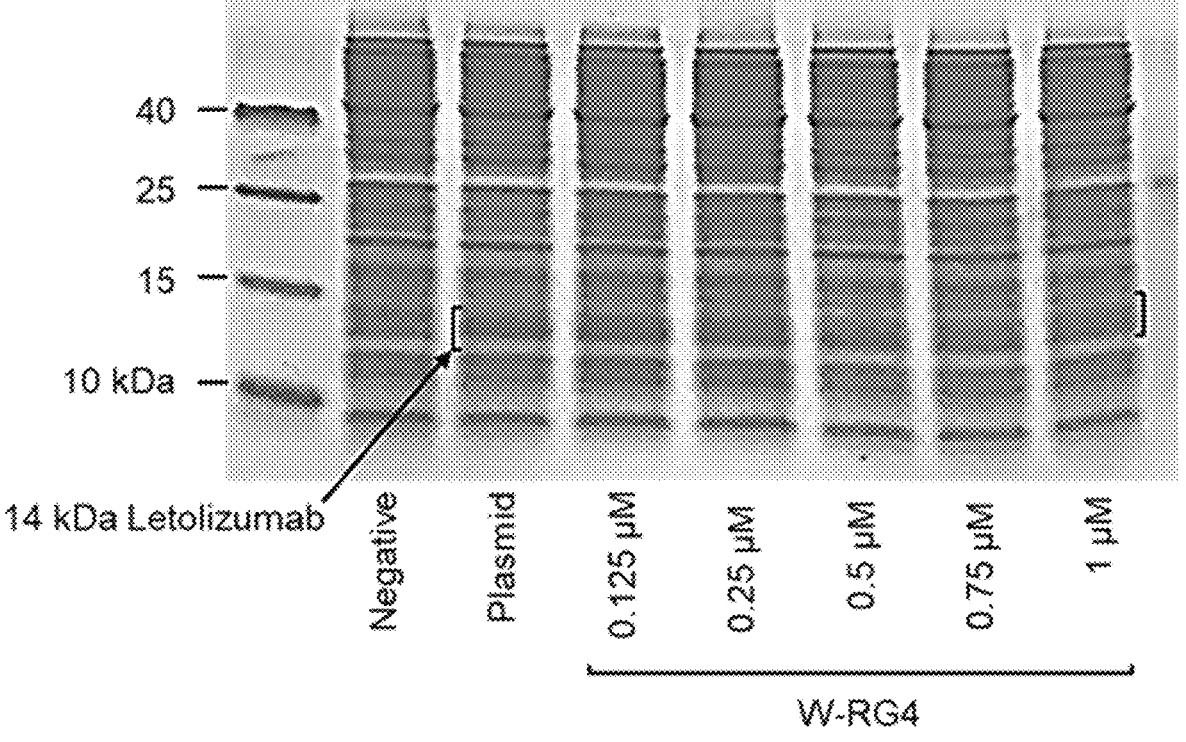
FIG. 5G shows results of analyzing Letolizumab protein expression by SDS-PAGE indicated by square brackets with various concentrations of the spacer template for 60T RG4.
Figure 17B:
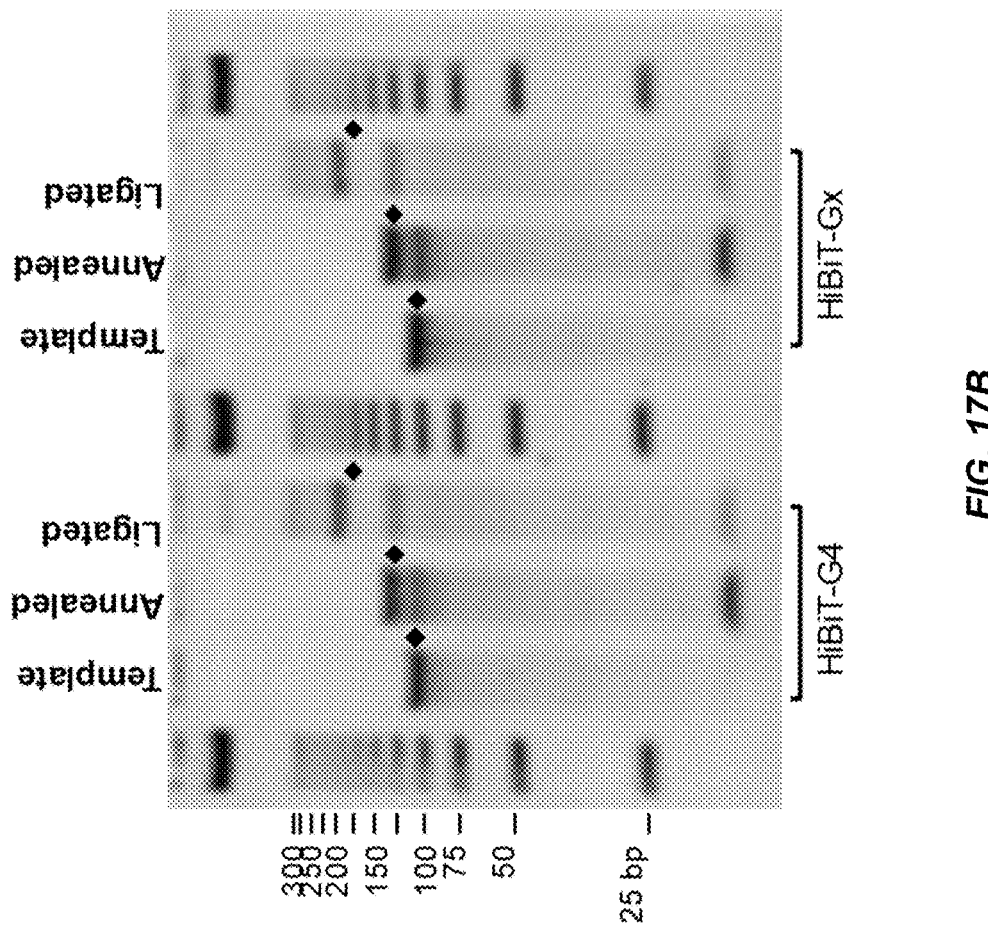
FIG. 17A-17D show the results of fabrication of HiBiT-encoding RCT products.
Figure 17A:
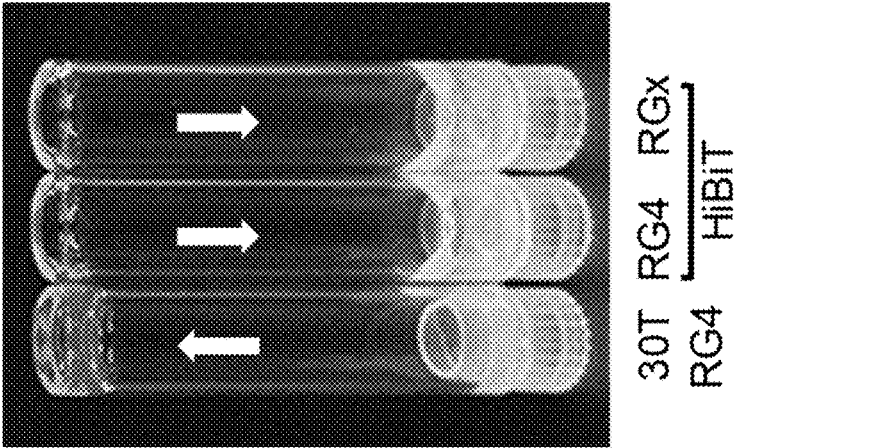
Figure 17D:
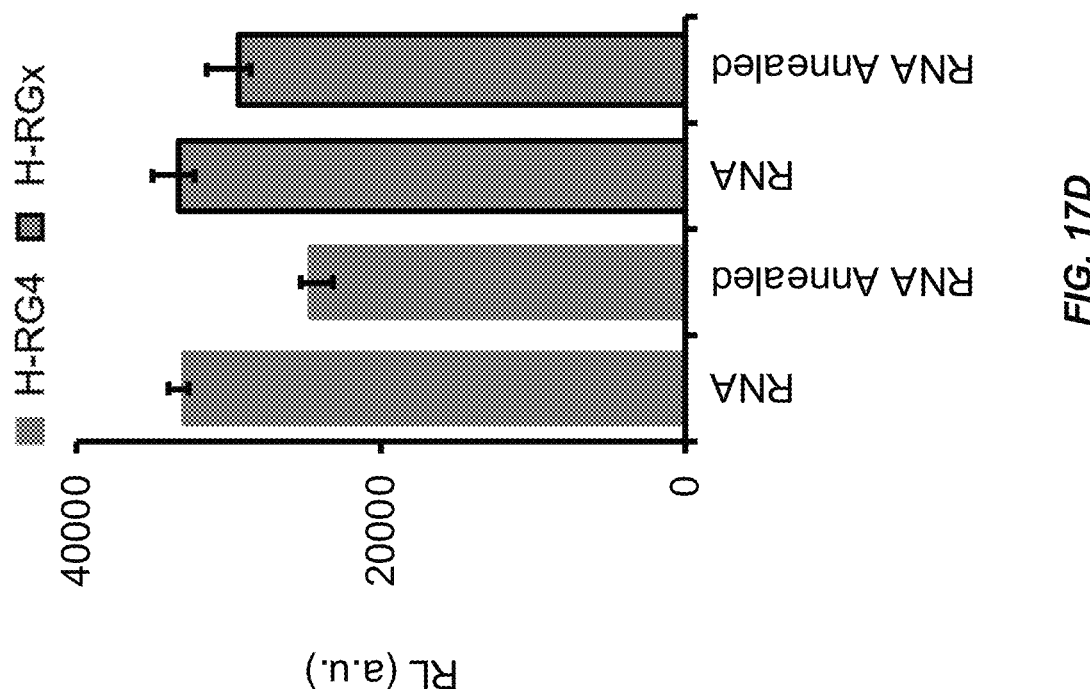
Figure 17C:
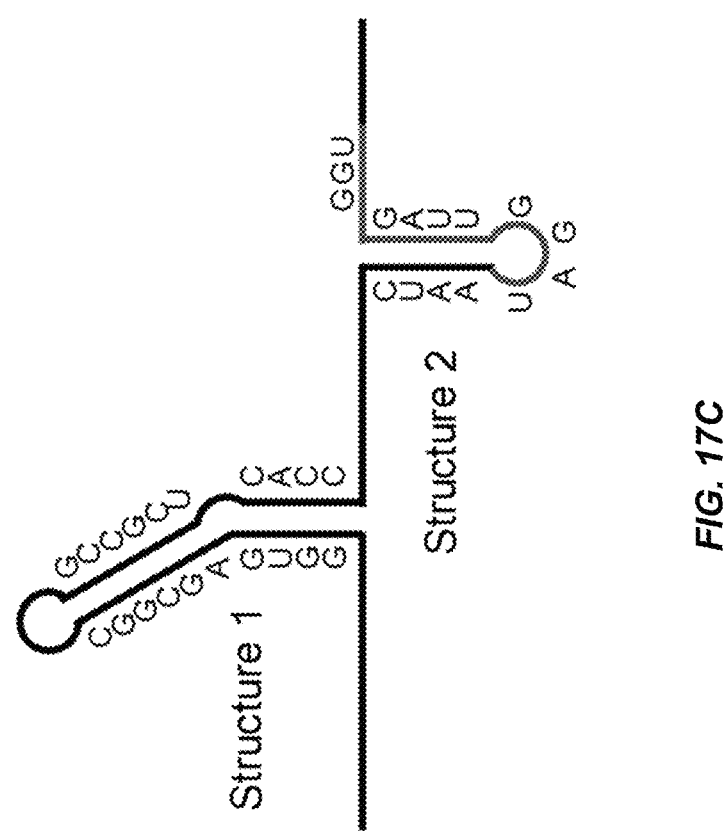

Influenced by those properties of the RG4 hydrogel, we evaluated its protein production ability as sketched (FIG. 5A). We replaced the poly T spacer region with a protein-encoding sequence (SEQ ID NO: 21) and then fabricated the RG4 hydrogel followed by uncoupled translation of proteins. HiBiT, an 11 amino-acid peptide tag, widely used to study the dynamics of endogenously expressed proteins and short protein molecules that are hard to be expressed in the in vitro system (34). The high-affinity of HiBiT for the large subunit LgBiT® generates a bright luminescent signal and simplifies the detection of expressed proteins. HiBiT-encoding RG4 (H-RG4) (the RCT product of a circular DNA template having the sequence of SEQ ID NO: 14 fabricated in a similar fashion seemed viscous exhibiting non-sturdiness though it possessed inherent G4s, while their 30T RG4 hydrogel (the RCT product of a corresponding circular DNA template having the sequence of SEQ ID NO: 6) was successfully formed (FIG. 17A). To achieve the best practice with our system, we used a method that enables hydrogelation of H-RG4 by supplementing it with 30T RG4 (the RCT product of a circular DNA template having the sequence of SEQ ID NO: 6) to make wideband RG4 (W-RG4). Fusing these templates produced a firm hydrogel by virtue of their multivalent interactions upon mixing (11) (FIG. 18A-18C). W-RG4 had elevated protein efficiency at a mixing ratio of 75% (FIG. 18D) with an elastic strength of 9.71 kPa (FIG. 18E). The W-RG4 was then cut 300 times (FIG. 19). The protein expression yield of W-RG4 was compared with that of the free templates, where 117-fold enhancement over the free DNA template (fDNA) and an 8-fold enhancement over the free RNA (fRNA) template were observed (FIG. 5B). Furthermore, enhanced in vitro protein expression was achieved by varying parameters of chaotropic treatment, reaction time, type, volume, and temperature (FIG. 21).

2. TAT and Insulin

With this confidence, we further explored the aspect of therapeutic protein production which is a pressing need in the health care system. Trans-activating transcriptional activator (TAT) and insulin proteins were chosen due to their significance in therapy where a rational formulation of protein therapeutics can be delivered with the use of RNA hydrogel. The TAT encoding sequence used in this study includes a partial 10-amino acid functional basic region of the HIV (human immunodeficiency virus) TAT protein SEQ ID NO:24 (35). The insulin encoding sequence used in this study includes a 30-amino acid B-chain of human insulin SEQ ID NO: 23 (36).

Figure 5H:
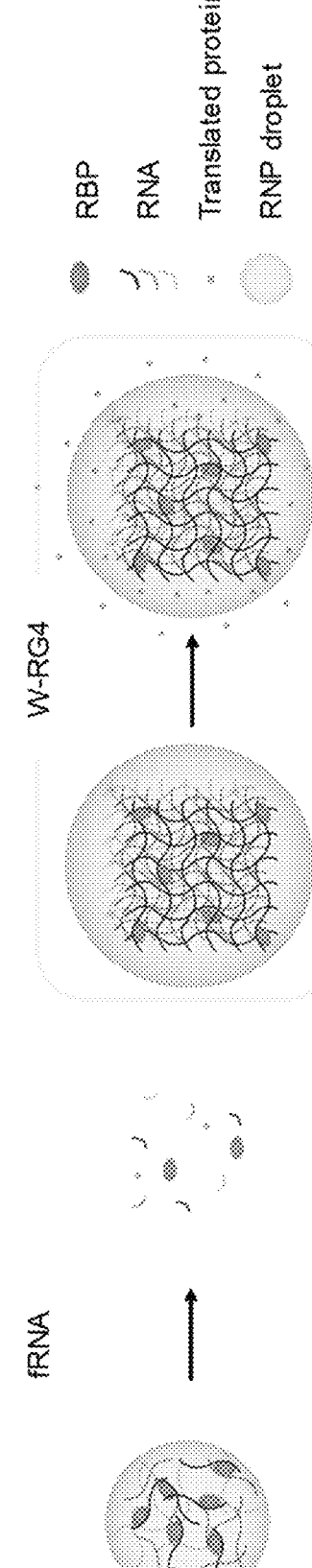
FIG. 5H is a schematic illustration of phase-separated RNA droplet in the in vitro translation process. RNA and RNA binding proteins (RBPs) are a key component in vivo that make up the ribonucleoprotein (RNPs) droplets. These RNPs mimic how the cell can organize itself in a spatiotemporally and functionally regulated manner. RNA hydrogel resembling the intracellular RNP system can facilitate diffusion of protein components thus enhancing the protein efficiency.
Figure 5J:
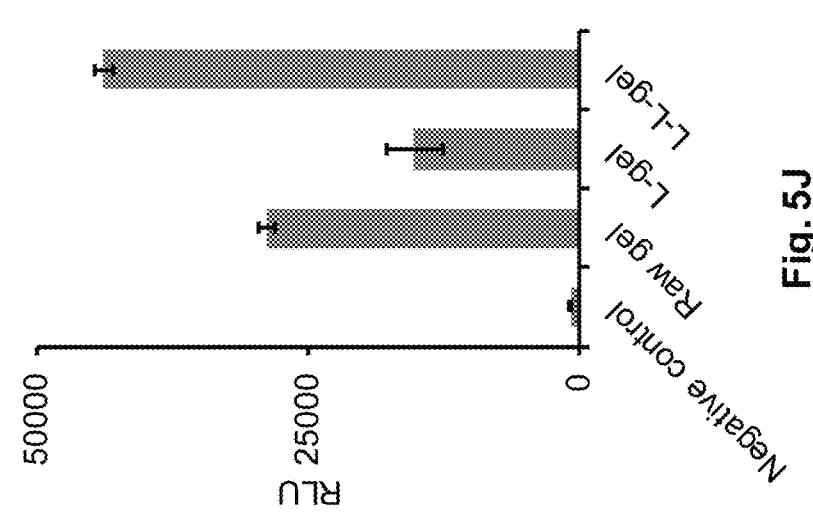
FIGS. 5I and 5J show the results of cell-free expression yield of HiBiT from lysate-embedded W-RG4 gels.

TAT and insulin templates (SEQ ID NOs: 16 and 18, respectively) embedded with a HiBiT tag possessed 10- and 18-fold increase in W-RG4 compared with the fDNA templates, respectively (FIG. 5C and FIG. 22). Uncoupled translation expressing HiBiT was also performed using the wheat germ system, a well-established and a cap independent translation system and we observed 8-fold increase in the yield (FIG. 5D). RNA binding proteins (RBPs) and associated RNA molecules condense to form membrane-less organelles called ribonucleoproteins (RNPs) promoting phase separation. Since we lack organelles like cytoskeletons in the cell-free system, we developed a RNA hydrogel in which the RNAs seed, nucleate and phase separate (FIG. 5H). In addition, cell-free system is not suitable for production of short peptides. With the structurally long RNA in confined space which enables miRNA localization and hence increases the expression yield. The efficiency varied greatly with length and type of sequences involved in protein expression (39). Accommodations of RBPs (ribosomes in our case) on the transcribed RNAs are in close proximity within the scaffold facilitating easy accessibility of translation components. The efficiency can be further improved by outpacing the spatial impediments (40) and addressing the global challenges through cell-free assessment of cellular functions (41) (FIG. 23).

3. A Single Domain Antibody Letolizumab

We also tested the protein production of 14 kDa single-domain antibody Letolizumab using the W-RG4 approach (FIG. 5E) via mRNAs originating from the expression cassette of the pK7-Letolizumab-G4 plasmid. Letolizumab, Fc-modified Human IgG1 fusion protein construct developed for an immunomodulatory purpose that targets CD40L (37, 38). For this assay, Letolizumab-G4 in pIDTBlue plasmid (Integrated DNA technologies, Coralville, IA) was digested with NdeI and SalI and cloned into pK7 plasmid to generate the pK7-Letolizumab-G4 plasmid. 20 ng of the pK7-Letolizumab-G4 plasmid was used as a positive control for cell-free expression, and 20 ng of the pK7-Letolizumab-G4 plasmid was transcribed together with 0.125 μM, 0.25 μM, 0.5 μM, 0.75 μM, or 1 μM spacer template (the molar ratios between the plasmid and the spacer template were 1:12.76, 1:25.51, 1:51.02, 1:76.53, and 1:102.04, for 60 T RG4, respectively) to induce gelation.

The RCT products from the 60T RG4 template and mRNA transcripts from the plasmid together form a W-RG4 hydrogel. Translation was performed at 30° C. for 8 hours. FIGS. 5F and 5G show that the expression was enhanced up to 2-fold when the 60T-RG4 template was used.

4. Protein Production Using Lysate-Embedded W-RG4 Gel

Figure 5I:
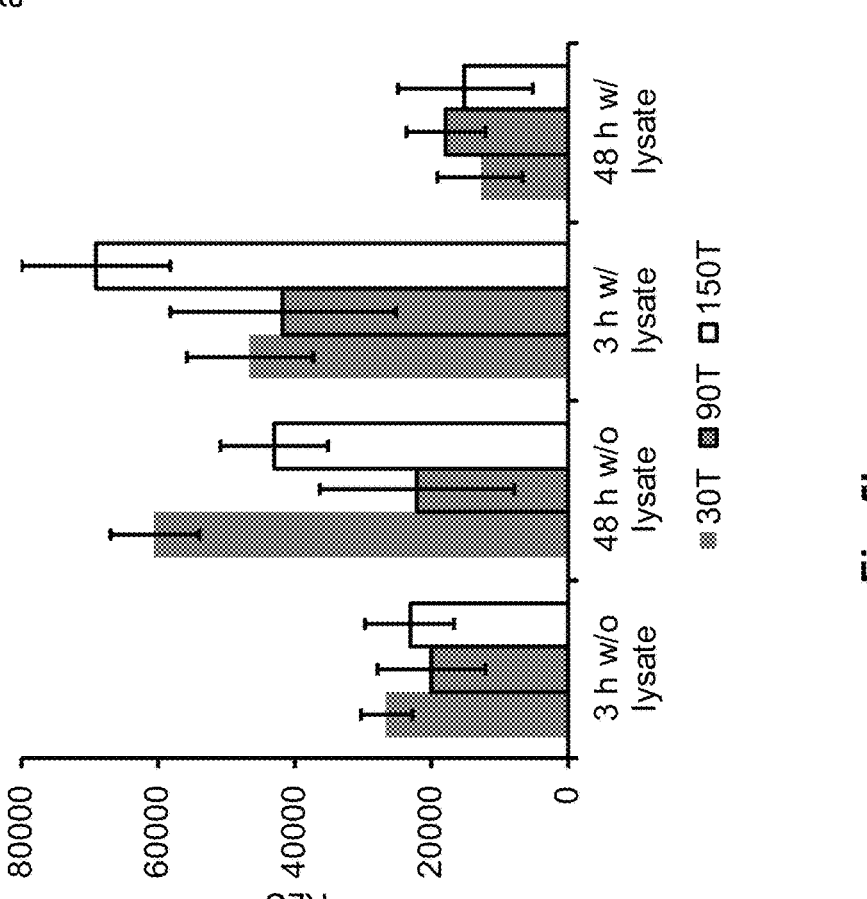

FIG. 5I shows the results of protein production using lysate-embedded W-RG4 versus protein production from W-RG4 produced in the absence of any cell lysate (lysate-free W-RG4). Unless specifically noted otherwise, a W-RG4 disclosed in this disclosure is a lystate-free W-RG4

Lystate embedding W-RG4 gel were produced by mixing the following ingredients, shown in Table 3, below.

TABLE 3

| Ingredients | Source |
| --- | --- |
| 3 μl of lysate/Rnase Inhibitor mixture, in which the volume ratio of the lysate to the Rnase inhibitor was 12:1 | NEBExpress Cell-free E. coli Protein Synthesis System, Catalog #E5360, New England Biolabs (Ipswich, MA). |
| 1.1 μl of Buffer | Hiscribe T7 High Yield RNA Synthesis Kit, New England Biolabs E2040S |
| 4.4 μl of rNTP mix (which includes equal amount of rATP, rUTP, rCTP, and rGTP) | New England Biolabs E2040S |
| 1.1 μl of T7 polymerase | New England Biolabs E2040S |
| 0.3 μl of Dnase-free, Rnase-free water | |

1.1 μL of a template mixture containing 75% HiBiT-RG4 template (SEQ ID NO: 14) and 25% of the spacer template for 30T-RG4 (SEQ ID NO: 6), the spacer template for 90T-RG4 (SEQ ID NO: 8), or the spacer template for 150T-RG4 (SEQ ID NO: 11), were added to the transcription reaction mixture above. 75% and 25% refer to the respective molar fraction of the HiBiT-RG4 template and the spacer template in the total template mixture. The transcription reaction mixture was incubated at 37° C. for 3 hours or 48 hours, during which the RNA transcripts were produced from these templates and form a hydrogel.

Lysate-free W-RG4s expressing HiBiT were produced using the same protocol as above except no lysate/Rnase Inhibitor mixture was added. In addition, 3.3 μl Dnase-free, Rnase-free water was used in producing lysate-free W-RG4s as opposed to 0.3 μL for producing the lysate-embedded W-RG4.

After hydrogels were formed, translation reactions were carried out using the NEBExpress Cell-free E. coli Protein Synthesis System (NEB #E5360). 11 μL of lysate-free W-RG4 or lysate-embedded W-RG4 was incubated with 25 μL protein synthesis buffer, 10 μL lysate/Rnase inhibitor mixture (a volume ratio of the lysate to the Rnase inhibitor was 12 to 1), and 104 μL Dnase free Rnase free water to initiate protein translation. Translation reactions were kept at 25° C. and terminated after two hours.

As shown in FIG. 5I, lysate-embedded W-RG4 that was formed from a 3-hour transcription reaction ("3h w/lystate") produced a higher amount of HiBiT, as compared to the lysate-free counterpart ("3 h w/o lysate"). The amount of HiBiT produced from W-RG4 formed after a 48-hour transcription reaction (gel preparation time) was lower than the amount of HiBiT produced from W-RG4 formed after a 3-hour transcription reaction, which is possibly due to RNA degradation associated with embedding the cell lysate embedded in the hydrogel.

Effects of cell lysates in the translation reaction mixtures on protein production were tested, and the results are shown in FIG. 5J. The lysate-free W-RG4 ("raw W-RG4") and lysate embedding W-RG4 gels were produced by performing rolling circle transcription of the spacer template comprising 150 poly thymines (SEQ ID NO: 11) and HiBiT-RG4 template (SEQ ID NO: 14) using the methods described above. The lysate-free W-RG4 was incubated with a translation mixture containing 12 μL lysate (NEB #E5360) ("Raw gel"); the lysate-embedded W-RG4 was incubated with a translation mixture containing no lysates ("L-gel"); and the lysate-embedded W-RG4 was incubated with a translation mixture containing 10 μL lysate ("L-L-gel"). All three translation mixtures contain a feed solution (also known as a protein synthesis buffer). Relative protein production levels from these reactions were indicated by the RLU values. The translation from a template for 30T RG4 (SEQ ID NO: 6) was used as a negative control. All translation reactions were terminated after 3 hours.

FIG. 5J shows that the lysate-embedded W-RG4 with additional lysate introduced during the translation step showed the highest expression yield ("L-L-gel"). Surprisingly, the lysate-embedded W-RG4 was able to produce sufficient proteins even when no cell lysates were added to the translation reaction mixture ("L-gel"), albeit at a lower yield. The successful expression from the lysate-embedded W-RG4 indicates that these lysate-embedded W-RG4 gels can potentially act as a self-sufficient protein expression system. Thus, these lysate-embedded W-RG4 gels can be useful for implantable or injectable therapeutic applications where it is preferable or even required that no external lysates were used in translation.

REFERENCES

1. N. C. Seeman, H. F. Sleiman, DNA nanotechnology. Nat. Rev. Mater. 3 (2017).
2. H. Ramezani, H. Dietz, Building machines with DNA molecules. Nat. Rev. Genet. 21, 5-26 (2020).
3. K. A. Afonin, E. Bindewald, A. J. Yaghoubian, N. Voss, E. Jacovetty, B. A. Shapiro, L. Jaeger, In vitro assembly of cubic RNA-based scaffolds designed in silico. Nat. Nanotechnol. 5, 676-682 (2010).
4. S. E. Butcher, A. M. Pyle, The molecular interactions that stabilize RNA tertiary structure: RNA motifs, patterns, and networks. Acc. Chem. Res. 44, 1302-1311 (2011).
5. D. W. Staple, S. E. Butcher, Pseudoknots: RNA structures with diverse functions. PLoS Biol. 3, 0956-0959 (2005).

6. H. Shin, S.-J. Park, Y. Yim, J. Kim, C. Choi, C. Won, D.-H. Min, Recent Advances in RNA Therapeutics and RNA Delivery Systems Based on Nanoparticles. Adv. Ther. 1, 1800065 (2018).

7. N. V. Hud, B. J. Cafferty, R. Krishnamurthy, L. D. Williams, The origin of RNA and "my grandfather's axe." Chem. Biol. 20, 466-474 (2013).

8. J. C. Nshogozabahizi, K. L. Aubrey, J. A. Ross, N. Thakor, Applications and limitations of regulatory RNA elements in synthetic biology and biotechnology. J. Appl. Microbiol. 127, 968-984 (2019).

9. J. Conde, N. Oliva, M. Atilano, H. S. Song, N. Artzi, Self-assembled RNA-triple-helix hydrogel scaffold for microRNA modulation in the tumour microenvironment. Nat. Mater. 15, 353-363 (2016).

10. Z. Huang, G. N. Kangovi, W. Wen, S. Lee, L. Niu, An RNA Aptamer Capable of Forming a Hydrogel by Self-Assembly. Biomacromolecules. 18, 2056-2063 (2017).

11. A. Jain, R. D. Vale, RNA phase transitions in repeat expansion disorders. Nature. 546, 243-247 (2017).

12. A. T. Phan, Human telomeric G-quadruplex: Structures of DNA and RNA sequences. FEBS J. 277, 1107-1117 (2010).

13. H. L. Bao, Y. Xu, Investigation of higher-order RNA G-quadruplex structures in vitro and in living cells by 19 F NMR spectroscopy. Nat. Protoc. 13, 652-665 (2018).

14. W. Zhao, M. M. Ali, M. A. Brook, Y. Li, Rolling circle amplification: Applications in nanotechnology and biodetection with functional nucleic acids. Angew. Chemie-Int. Ed. 47, 6330-6337 (2008).

15. C. C. Hardin, T. Watson, M. Corregan, C. Bailey, Cation-Dependent Transition between the Quadruplex and Watson-Crick Hairpin Forms of d(CGCG3GCG). Biochemistry. 31, 833-841 (1992).

16. M. Vorlíčková, I. Kejnovská, J. Sagi, D. Renčiuk, K. Bednářová, J. Motlová, J. Kypr, Circular dichroism and guanine quadruplexes. Methods. 57, 64-75 (2012).

17. M. M. Fay, S. M. Lyons, P. Ivanov, RNA G-Quadruplexes in Biology: Principles and Molecular Mechanisms. J. Mol. Biol. 429, 2127-2147 (2017).

18. J. Mohanty, N. Barooah, V. Dhamodharan, S. Harikrishna, P. I. Pradeepkumar, A. C. Bhasikuttan, Thioflavin T as an efficient inducer and selective fluorescent sensor for the human telomeric G-quadruplex DNA. J. Am. Chem. Soc. 135, 367-376 (2013).

19. M. I. Umar, D. Ji, C. Y. Chan, C. K. Kwok, G-quadruplex-based fluorescent turn-on ligands and aptamers: From development to applications. Molecules. 24, (2019).

20. M. Liu, T. Kagahara, H. Abe, Y. Ito, In vitro selection of hemin-binding catalytic RNA. Bioorganic Med. Chem. Lett. 19, 1484-1487 (2009).

21. P. Travascio, D. Sen, A. J. Bennet, DNA and RNA enzymes with peroxidase activity—An investigation into the mechanism of action. Can. J. Chem. 84, 613-619 (2006).

22. W. Li, W. Zeng, Y. Chen, F. Wang, F. Wu, X. Weng, X. Zhou, Biotinylation and isolation of an RNA G-quadruplex based on its peroxidase-mimicking activity. Analyst. 144, 4472-4476 (2019).

23. W. Hermann, H.-G. Sockel, Elastic Modulus Measurement. Encycl. Mater. Sci. Technol., 2427-2429 (2001).

24. R. Kocen, M. Gasik, A. Gantar, S. Novak, Viscoelastic behaviour of hydrogel-based composites for tissue engineering under mechanical load. Biomed. Mater. 12 (2017).

25. C. Ceccaldi, S. G. Fullana, C. Alfarano, O. Lairez, D. Calise, D. Cussac, A. Parini, B. Sallerin, Alginate scaffolds for mesenchymal stem cell cardiac therapy: Influence of alginate composition. Cell Transplant. 21, 1969-1984 (2012).

26. M. Lekka, Discrimination between normal and cancerous cells using AFM. Bionanoscience. 6, 65-80 (2016).

27. S. Huth, S. Sindt, C. Selhuber-Unkel, Automated analysis of soft hydrogel microindentation: Impact of various indentation parameters on the measurement of Young's modulus. PLoS One. 14, 1-17 (2019).

28. P. Karacan, H. Cakmak, O. Okay, Swelling behavior of physical and chemical DNA hydrogels. J. Appl. Polym. Sci. 128, 3330-3337 (2013).

29. L. Weng, X. Chen, W. Chen, Rheological characterization of in situ crosslinkable hydrogels formulated from oxidized dextran and N-carboxyethyl chitosan. Biomacromolecules. 8, 1109-1115 (2007).

30. J. B. Lee, S. Peng, D. Yang, Y. H. Roh, H. Funabashi, N. Park, E. J. Rice, L. Chen, R. Long, M. Wu, D. Luo, A mechanical metamaterial made from a DNA hydrogel. Nat. Nanotechnol. 7, 816-820 (2012).

31. S. H. Um, J. B. Lee, N. Park, S. Y. Kwon, C. C. Umbach, D. Luo, Enzyme-catalysed assembly of DNA hydrogel. Nat. Mater. 5, 797-801 (2006).

32. B. Amsden, Solute diffusion within hydrogels. Mechanisms and models. Macromolecules. 31, 8382-8395 (1998).

33. N. Park, S. H. Um, H. Funabashi, J. Xu, D. Luo, A cell-free protein-producing gel. Nat. Mater. 8, 432-437 (2009).

34. M. K. Schwinn, T. Machleidt, K. Zimmerman, C. T. Eggers, A. S. Dixon, R. Hurst, M. P. Hall, L. P. Encell, B. F. Binkowski, K. V. Wood, CRISPR-Mediated Tagging of Endogenous Proteins with a Luminescent Peptide. ACS Chem. Biol. 13, 467-474 (2018).

35. Shojania, S. & O'Neil, J. D. Intrinsic disorder and function of the HIV-1 tat protein. Protein Pept. Lett. 17, 999-1011 (2010).

36. Ladisch, M. R. & Kohlmann, K. L. Recombinant human insulin. Biotechnol. Prog. 8, 469-478 (1992).

37. W. H. O. D. Information, P. International Nonproprietary Names for Pharmaceutical Substances (INN) Substances pharmaceutiques (DCI) Denominaciones Comunes Internacionales para. 28, 485-563 (2014).

38. Karnell, J. L., Rieder, S. A., Etinger, R., Kolbeck, R. Targeting the CD40-CD40L pathway in autoimmune diseases: Humoral immunity and beyond. Adv. Drug Deliv. Rev. 141, 92-103 (2019).

39. K. Rhine, V. Vidaurre, S. Myong, RNA Droplets. Annu. Rev. Biophys. 49, 247-265 (2020).

40. C. J. Whitfield, A. M. Banks, G. Dura, J. Love, J. E. Fieldsend, S. A. Goodchild, A. Fulton, T. P. Howard, Cell-free protein synthesis in hydrogel materials, 1-4 (2020).

41. A. D. Silverman, A. S. Karim, M. C. Jewett, Cell-free gene expression: an expanded repertoire of applications. Nat. Rev. Genet. 21, 151-170 (2020).

42. M. M. K. Hansen, S. Paffenholz, D. Foschepoth, H. A. Heus, J. Thiele, W. T. S. Huck, Cell-Like Nanostructured Environments Alter Diffusion and Reaction Kinetics in Cell-Free Gene Expression. ChemBioChem. 17, 228-232 (2016).

43. Li, W. et al. Insight into G-quadruplex-hemin DNAzyme/RNAzyme: Adjacent adenine as the intramolecular species for remarkable enhancement of enzymatic activity. Nucleic Acids Res. 44, 7373-7384 (2016).

44. Travascio, P., Sen, D. & Bennet, A. J. DNA and RNA enzymes with peroxidase activity—An investigation into the mechanism of action. Can. J. Chem. 84, 613-619 (2006).

45. Einarson, O. J. & Sen, D. Self-biotinylation of DNA G-quadruplexes via intrinsic peroxidase activity. Nucleic Acids Res. 45, 9813-9822 (2017).

46. Taki, A., John, B., Arakawa, S. & Okamoto, M. Structure and rheology of nanocomposite hydrogels composed of DNA and clay. Eur. Polym. J. 49, 923-931 (2013).

47. Groenning, M. Binding mode of Thioflavin T and other molecular probes in the context of amyloid fibrils-current status. J. Chem. Biol. 3, 1-18 (2010).

48. Voss, N. R., Gerstein, M., Steitz, T. A. & Moore, P. B. The geometry of the ribosomal polypeptide exit tunnel. J. Mol. Biol. 360, 893-906 (2006).

49. Miller, C. C. The Stokes-Einstein law for diffusion in solution. P. Roy. Soc. A-Math. Phy. 106, 724-749 (1924).

50. Watson, J. T. R., Basu, R. S. & Sengers, J. V. An improved representative equation for the dynamic viscosity of water substance. J. Phys. Chem. Ref. Data 9, 1255-1290 (1980).

51. Phillips, R. J., Deen, W. M. & Brady, J. F. Hindered transport of spherical macromolecules in fibrous membranes and gels. AIChE J. 35, 1761-1769 (1989).

52. Atkins, P. & de Paula, J. Physical chemistry for the life science. Oxford University Press (2006).

53. Aris, R. Vectors, Tensors, and the basic equations of fluid mechanics. Dover Publications (1989).

54. Vineeth Thachappilly Mukundan and Anh Tuân Phan. Bulges in G-Quadruplexes: Broadening the Definition of G-Quadruplex-Forming Sequences. J. of the American Chemical Society (2013).

INCORPORATION BY REFERENCE

For all purposes in the United States of America, each and every publication and patent document referred to in this disclosure is incorporated herein by reference in its entirety for all purposes to the same extent as if each such publication or document was specifically and individually indicated to be incorporated herein by reference.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed and their equivalents.

ILLUSTRATIVE SEQUENCES

In this listing of illustrative sequences, the underlined represent the G-quadruplex motif. The double underlined represent the scrambled G-quadruplex motifs. All sequences are listed in the direction of 5'→3'.

```
SEQ ID NO: 1:
the G quadruplex moiety
ACCCTAACCCTA

SEQ ID NO: 2:
G-quarduplex motif (RNA)
UAGGGUUAGGGU

SEQ ID NO: 3
(the part of the g-quadruplex template preceding the spacer)
ATAGTGAGTCGTATTAACCCTAACCCTA SEQ ID NO: 4
(3 T G-quadruplex template)
ATAGTGAGTCGTATTAACCCTAACCCTATTTATCCCT SEQ ID NO: 5
(10 T G-quadruplex template)
ATAGTGAGTCGTATTAACCCTAACCCTATTTTTTTTTTATCCCT SEQ ID NO: 6
(30 T G-quadruplex template)
ATAGTGAGTCGTATTAACCCTAACCCTATTTTTTTTTTTTTTTTTTTTTTTTTTTTTT ATCCCT SEQ ID NO: 7
(60 T G-quadruplex template)
ATAGTGAGTCGTATTAACCCTAACCCTATTTTTTTTTTTTTTTTTTTTTTTTTTTTTTTTTTTTT

TTTTTTTTTTTTTTTTTTTTTATCCCT

SEQ ID NO: 8
(90 T G-quadruplex template)
ATAGTGAGTCGTATTAACCCTAACCCTATTTTTTTTTTTTTTTTTTTTTTTTTTTTTTTTTTTTT

TTTTTTTTTTTTTTTTTTTTTTTTTTTTTTTTTTTTTTTTTTTTTTTTTATCCCT

SEQ ID NO: 9
(120 T G-quadruplex template)
ATAGTGAGTCGTATTAACCCTAACCCTATTTTTTTTTTTTTTTTTTTTTTTTTTTTTTTTTTTTT

TTTTTTTTTTTTTTTTTTTTTTTTTTTTTTTTTTTTTTTTTTTTTTTTTTTTTTTTTTTTTTTTT

TTTTTTTTTTTTATCCCT
```

-continued

SEQ ID NO: 10
(Scrambled 30 T G-quadruplex template)
ATAGTGAGTCGTATTAACAGTAACAGTATTTTTTTTTTTTTTTTTTTTTTTTTTTTT ATCCCT SEQ ID NO: 11
(150 T G-quadruplex template)
ATAGTGAGTCGTATTAACCCTAACCCTATTTTTTTTTTTTTTTTTTTTTTTTTTTTTTTTTTTTTTT

TTTTTTTTTTTTTTTTTTTTTTTTTTTTTTTTTTTTTTTTTTTTTTTTTTTTTTTTTTTTTTTTTTTTT

TTTTTTTTTTTTTTTTTTTTTTTTTTTTTTTTTTTTTTTTATCCCT

SEQ ID NO: 12
(T7 promoter primer)
TAATACGACTCACTATAGGGAT

SEQ ID NO: 13
(Short scrambled G-quadruplex RNA)
UACUGUUACUGU

SEQ ID NO: 14
(HiBiT G-quadruplex template)
ATAGTGAGTCGTATTAACCCTAACCCTATTAGCTAATCTTCTTGAACAGCCGCCAGCCGC

TCACCATATTTTTTCCTCCTTATACTTAATCCCT

SEQ ID NO: 15
(Scrambled linear HiBiT G-quadruplex template)
ACAGTAACAGTATTAGCTAATCTTCTTGAACAGCCGCCAGCCGCTCACCATATTTTTTCC

TCCTTATACTTAATCCCTTATAGTGAGTCGTATTA

SEQ ID NO: 16
(TAT-HiBiT tag G-quadruplex template; the italicized portion
is the TAT coding sequence, the anti-sense strand)
ATAGTGAGTCGTATTAACCCTAACCCTATTAGCTAATCTTCTTGAACAGCCGCCAGCCGC

TCACTCTTCGTCGCTGTCTCCGCTTCTTCCTGCCCATATTTTTTCCTCCTTATACTTAATCCCT

SEQ ID NO: 17
(Scrambled linear TAT-HiBiT tag G-quadruplex template;
the italicized portion is the TAT coding sequence)
ACAGTAACAGTATTAGCTAATCTTCTTGAACAGCCGCCAGCCGCTCACTCTTCGTCGCTGT

CTCCGCTTCTTCCTGCCCATATTTTTTCCTCCTTATACTTAATCCCTATAGTGAGTCGTATTA

SEQ ID NO: 18
(Insulin-HiBiT tag G-quadruplex template; the italicized portion
is the insulin coding sequence, the antisense strand)
ATAGTGAGTCGTATTAACCCTAACCCTATTAGCTAATCTTCTTGAACAGCCGCCAGCCGC

TCACGGTGTTGGGTGTGTAGAAGAAGCCTCGTTCCCCGCACACTAGGTAGAGAGCTTCCACCAGG

TGTGAGCCGCACAGGTGTTGGTTCACAAACATATTTTTTCCTCCTTATACTTAATCCCT

SEQ ID NO: 19
(Scrambled linear Insulin-HiBiT tag G-quadruplex
template; the italicized portion is the insulin coding
sequence, the antisense strand)
ACAGTAACAGTATTAGCTAATCTTCTTGAACAGCCGCCAGCCGCTC

ACGGTGTTGGGTGTGTAGAAGAAGCCTCGTTCCCCGCACACTAGGTAGAGAGCTTCCACCAGGTG

TGAGCCGCACAGGTGTTGGTTCACAAACATATTTTTTCCTCCTTATACTTAATCCCTATAGTG

AGTCGTATTA

SEQ ID NO: 20:
G-quarduplex motif (DNA)
TAGGGTTAGGGT

SEQ ID NO: 21
(HiBiT coding sequence, the anti-sense strand)
TTAGCTAATCTTCTTGAACAGCCGCCAGCCGCTCAC

SEQ ID NO: 22
GGGUUAGGGU

SEQ ID NO: 23
(the amino acid sequence of insulin)
FVNQHLCGSHLVEALYLVCGERGFFYTPNT SEQ ID NO: 24
(the amino acid sequence of TAT
GRKKRRQRRR SEQ ID NO: 25
(the amino acid sequence of HiBiT)
VSGWRLIKKIS SEQ ID NO: 26
(coding sequence sequence for single domain antibody Letolizumab;
the sense strand, the underlined is the G-quadruplex motif)
CATATGATGGAGGTACAGTTACTGGAGAGTGGGGGCGGGTTGGTCCAACCAGGTGGGTCCC

TGCGTTTGTCCTGTGCCGCATCTGGGTTCACATTCAACTGGGAATTGATGGGCTGGGCACGC

CAAGCACCCGGCAAGGGACTTGAGTGGGTCTCGGGAATTGAAGGGCCGGGGGATGTCACCT

ATTATGCAGATTCAGTAAAGGGCCGGTTCACAATTTCGCGTGACAATTCGAAAAACACTCTT

TACTTGCAGATGAACTCACTTCGGGCGGAAGACACAGCTGTGTATTACTGCGTAAAGGTCGG

TAAGGACGCCAAGTCGGATTACAGAGGCCAAGGAACGCTTGTGACAGTATCAAGTGCCTCA

ACGTATCCATATGACGTACCCGATTATGCATGATAGGGTTAGGGTGTCGAC

SEQ ID NO: 27
(the amino acid sequence for the single domain antibody Letolizumab)
EVQLLESGGGLVQPGGSLRLSCAASGFTFNWELMGWARQAPGKGLEWVSGIEGPGDVTYYADS

VKGRFTISRDNSKNTLYLQMNSLRAEDTAVYYCVKVGKDAKSDYRGQGTLVTVSSAST

SEQ ID NO: 28
(HiBiT coding sequence, the sense strand)
GTGAGCGGCTGGCGGCTGTTCAAGAAGATTAGCTAA

SEQ ID NO: 29
GGUGAGCGGC

SEQ ID NO 30
GCCGCUCACC

SEQ ID NO: 31:
CUAAUAGGUUAGGGU

SEQ ID NO: 32:
TTTTTTTTTT TTTTTTTTTT TTTTTTTTTT TTTTTTTTTT TTTTTTTTTT TTTTTTTTTT

TTTTTTTTTT TTTTTTTTTT TTTTTTTTTT TTTTTTTTTT TTTTTTTTTT TTTTTTTTTT

SEQ ID NO: 33:
TTTTTTTTTT TTTTTTTTTT TTTTTTTTTT

SEQ ID NO: 34:
TTTTTTTTTT TTTTTTTTTT TTTTTTTTTT TTTTTTTTTT TTTTTTTTTT TTTTTTTTTT

SE0 ID NO: 35:
TTTTTTTTTT TTTTTTTTTT TTTTTTTTTT TTTTTTTTTT TTTTTTTTTT TTTTTTTTTT

TTTTTTTTTT TTTTTTTTTT TTTTTTTTTT

SEQ ID NO: 36:
TTTTTTTTTT TTTTTTTTTT TTTTTTTTTT TTTTTTTTTT TTTTTTTTTT TTTTTTTTTT

TTTTTTTTTT TTTTTTTTTT TTTTTTTTTT TTTTTTTTTT TTTTTTTTTT TTTTTTTTTT

SEQ ID NO: 37:
TTTTTTTTTT TTTTTTTTTT TTTTTTTTTT TTTTTTTTTT TTTTTTTTTT TTTTTTTTTT

TTTTTTTTTT TTTTTTTTTT TTTTTTTTTT TTTTTTTTTT TTTTTTTTTT TTTTTTTTTT

TTTTTTTTTT TTTTTTTTTT TTTTTTTTTT

SEQ ID NO: 38:
TTTTTTTTTT

SEQ ID NO: 39:
TTTTTTTTTT

SEQ ID NO: 40:
TTTTTTTTTT TT

-continued

SEQ ID NO: 41:
TTTTTTTTTT TTT

SEQ ID NO: 42:
TTTTTTTTTT TTTT

SEQ ID NO: 43:
TTTTTTTTTT TTTTT

SEQ ID NO: 44:
TTTTTTTTTT TTTTTT

SEQ ID NO: 45:
TTTTTTTTTT TTTTTTTTTT

SEQ ID NO: 46
$G_{3+}N_{1-7}G_{3+}N_{1-7}G_{3+}N_{1-7}G_{3+}$

SEQ ID NO: 47
AG GGT AAG GGT A

SEQ ID NO: 48
AG GGT AAG GGT AAG GGT AAG GGT A

SEQ ID NO: 49
AG GGT TAG GGT TAG GGT TAG GGT T

SEQ ID NO: 50
GGUCAUGGGAAAGGGCAGG

SEQ ID NO: 51
GGAGGAGGAGG

SEQ ID NO: 52
GGGGGGGGCGGGGGAGGCCGGGG

SEQ ID NO: 53
GGTGGTGGTGG

SEQ ID NO: 54
GGACGAGGGGUUGUUGGGACGUGGG

SEQ ID NO: 55
GGTGGTGGGGG

SEQ ID NO: 56
GGTTGGGTAGGGTGG

SEQ ID NO: 57
GGCGGUGGUGG

SEQ ID NO: 58
GGGGCGGGUGGGGAGGGG

SEQ ID NO: 59
GGATCCTGGGAAACAGGCAGAACTTCGG

SEQ ID NO: 60
GGGCAAAUAUUGGCAAUUAGUUGGCAGUGG

SEQ ID NO: 61
GGUUGGGAUUGGUGGGG

---

What is claimed is:

1. A first circular DNA template comprising (i) a first promoter sequence and (ii) a sequence complementary to a first G-quadruplex motif, wherein the first G-quadruplex motif comprises one or more sequence as set forth in SEQ ID NOs: 29-31, 48, 50, 52, 54-57 and/or 59-61.

2. The first circular DNA template of claim 1, wherein the first promoter sequence is hybridized to a complementary nucleic acid sequence to form a first partially double-stranded DNA molecule, wherein the first partially double-stranded DNA molecule comprises a double-stranded region and a single-stranded region, wherein the double-stranded region comprises the first promoter sequence hybridized to the complementary nucleic acid sequence, and wherein the single-stranded region comprises the sequence complementary to the first G-quadruplex motif.

3. The first circular DNA template of claim 1, further comprising a spacer, wherein the spacer comprises poly thymines, and/or further comprising a coding sequence of a polypeptide of interest.

4. A first nucleic acid concatemer comprising a plurality of monomers, wherein each monomer comprises a sequence complementary to the first circular DNA template of claim 1, wherein the monomer further comprises a spacer or a coding sequence for a polypeptide of interest.

5. A nucleic acid hydrogel comprising the first nucleic acid concatemer of claim 4.

6. A composition comprising the first circular DNA template of claim 1 and a second circular DNA template, wherein the first circular DNA template further comprises (iii) a spacer comprising poly thymines, wherein the second circular DNA template comprises (i) a second promoter sequence, (ii) a sequence complementary to a second G-quadruplex motif, and (iii) a coding sequence of a polypeptide of interest; and

US 12,606,857 B2

69
70 wherein the molar fraction of the first circular DNA template relative to the total amount of first and second circular DNA templates ranges from 25% to 75%.

7. The composition of claim 6, (1) wherein the first promoter sequence is hybridized to a complementary nucleic acid sequence to form a first partially double-stranded DNA molecule, wherein the first partially double-stranded DNA molecule comprises a double-stranded region and a single-stranded region, wherein the double-stranded region of the first partially double-stranded DNA molecule comprises the first promoter sequence hybridized to the complementary nucleic acid sequence, and wherein the single-stranded region of the first partially double-stranded DNA molecule comprises the sequence complementary to the first G-quadruplex motif; and (2) wherein the second promoter sequence is hybridized to a complementary nucleic acid sequence to form a second partially double-stranded DNA molecule, wherein the second partially double-stranded DNA molecule comprises a double-stranded region and a single-stranded region, wherein the double-stranded region of the second partially double-stranded DNA molecule comprises the second promoter sequence hybridized to the complementary nucleic acid sequence, and wherein the single-stranded region of the second partially double-stranded DNA molecule comprises the sequence complementary to the second G-quadruplex motif.

8. The composition of claim 7, wherein the polypeptide of interest is selected from the group consisting of insulin, Trans-activating transcriptional activator (TAT), HiBiT, and a single domain antibody.

9. A composition comprising the first circular DNA template of claim 1, and a double-stranded DNA construct, wherein the first circular DNA template further comprises (iii) a spacer comprising poly thymines, wherein the double-stranded DNA construct comprises (i) a second promoter sequence, (ii) a sequence complementary to a second G-quadruplex motif, and (iii) a coding sequence of a polypeptide of interest.

10. A nucleic acid hydrogel comprising a first nucleic acid concatemer and a second nucleic acid concatemer, wherein the first nucleic acid concatemer is produced by rolling circle transcription or amplification of the first circular DNA template of the composition of claim 6, and wherein the second nucleic acid concatemer is produced by rolling circle transcription or amplification of the second circular DNA template of the composition of claim 9.

11. A nucleic acid hydrogel comprising a first RNA molecule and a second RNA molecule, wherein the first RNA molecule comprises the first nucleic acid concatemer of claim 5, wherein the monomer further comprises the spacer, and wherein the second RNA molecule comprises the first nucleic acid concatemer of claim 3, wherein the monomer further comprises the coding sequence for a polypeptide of interest.

12. The nucleic acid hydrogel of claim 11, wherein the first RNA molecule is an RNA concatemer comprising a plurality of monomers and wherein each monomer comprises the first G-quadruplex motif, and the spacer or a coding sequence for a polypeptide of interest.

13. A protein expression system comprising the nucleic acid hydrogel of claim 10, a ribosome, and/or a mixture of amino acids.

14. A kit for expressing a polypeptide of interest, wherein the kit comprises (1) a first DNA molecule capable of forming a first circular DNA template by hybridizing to a first splint oligonucleotide, wherein the first circular DNA template comprises (i) a first promoter sequence, (ii) a DNA sequence complementary to a first G-quadruplex motif, wherein the first G-quadruplex motif comprises one or more sequence as set forth in SEQ ID NOs: 29-31, 48, 50, 52, 54-57 and/or 59-61, and (iii) a spacer comprising poly thymines, (2) a first splint oligonucleotide that is complementary to the first promoter sequence, wherein the first DNA molecule can hybridize to the first splint oligonucleotide and be circularized to form a first circular DNA template, and/or (3) a second DNA molecule capable of forming a second circular DNA template by hybridizing to a second splint oligonucleotide, wherein the second circular DNA molecule comprises (i) a second promoter sequence, (ii) a sequence complementary to a second G-quadruplex motif, and (iii) a coding sequence of the polypeptide of interest, (4) a second splint oligonucleotide that is complementary to the second promoter sequence, wherein the second DNA molecule can hybridize to the second splint oligonucleotide and be circularized to form a second circular DNA template.

15. The kit of claim 14, wherein the coding sequence has a length that ranges from 20 to 300 nucleotides.

16. A method of preparing a nucleic acid hydrogel comprising:

(1) providing the first circular DNA template of claim 1; and (2) performing a rolling circle transcription or amplification on the first circular template to produce a first nucleic acid concatemer, wherein the first nucleic acid concatemer forms a nucleic acid hydrogel.

17. The method of claim 16, wherein the first circular DNA template further comprises a spacer comprising poly thymines, wherein the step (1) further comprises providing a second circular DNA template comprising (i) a second promoter sequence, (ii) a second G-quadruplex motif, and (iii) a coding sequence of a polypeptide of interest, and wherein the step (2) further comprises performing a rolling circle transcription or amplification of the second circular DNA template to produce a second nucleic acid concatemer, wherein the first and second nucleic acid concatemers form the nucleic acid hydrogel.

18. A method for producing a protein in a cell-free synthesis system, wherein the method comprises:

(i) combining the nucleic acid hydrogel of claim 5 with a cell-free synthesis system under conditions permitting translation of the polypeptide of interest.

* * * * *